(12) United States Patent
Yokoyama et al.

(10) Patent No.: US 7,514,240 B2
(45) Date of Patent: Apr. 7, 2009

(54) EGR-EGFR COMPLEX

(75) Inventors: Shigeyuki Yokoyama, Kanagawa (JP); Hideo Ogiso, Kanagawa (JP); Mikako Shirouzu, Kanagawa (JP); Osamu Nureki, Kanagawa (JP); Ryuichiro Ishitani, Kanagawa (JP); Kazuki Saito, Chiba (JP)

(73) Assignees: Japan Science and Technology Agency, Saitama (JP); Riken, Saitama (JP); Mochida Pharmaceutical Co., Ltd., Tokyo (JP)

( * ) Notice: Subject to any disclaimer, the term of this patent is extended or adjusted under 35 U.S.C. 154(b) by 398 days.

(21) Appl. No.: 10/503,486

(22) PCT Filed: Sep. 12, 2002

(86) PCT No.: PCT/JP02/09332

§ 371 (c)(1),
(2), (4) Date: Aug. 5, 2004

(87) PCT Pub. No.: WO03/066677

PCT Pub. Date: Aug. 14, 2003

(65) Prior Publication Data

US 2007/0032637 A1    Feb. 8, 2007

(30) Foreign Application Priority Data

Feb. 5, 2002    (JP) .............................. 2002-028780

(51) Int. Cl.
C12P 1/00        (2006.01)
C12P 21/04       (2006.01)
C07K 14/00       (2006.01)
A61K 38/27       (2006.01)
G06F 19/00       (2006.01)

(52) U.S. Cl. ....................... 435/70.1; 703/11; 530/350; 530/395; 530/397; 530/399; 702/27

(58) Field of Classification Search .................. None
See application file for complete search history.

(56) References Cited

FOREIGN PATENT DOCUMENTS

WO        WO 01/36659 A2    5/2001

OTHER PUBLICATIONS

Betzel et al., Microgravity Sci. Technol., 1994, 7(3):242-245.*
Branden et al., "Introduction to Protein Structure Second Edition", Garland Publishing Inc., New York, 1999.*
Deutscher et al., A Chinese hamster ovary cell mutant deficient in translocation of UDP-galactose across Golgi vesicle membranes, 1986, J. Biol. Chem. 261:96-100.*
Mroczkowski et al., Recombinant Human Epidermal Growth Factor Precursor Is a Glycosylated Membrane Protein with Biological Activity, Molecular and Cellular Biology, 1989. p. 2771-2778.*
Grueninger-Leitch et al., Deglycosylation of proteins for crystallization using recombinant fusion protein glycosidase, Protein Science, 1996, 5: 2617-2622.*
Drenth, "Principles of X-ray Crystallography," Springer, New York, 1995.*
Kierzek et al., Biophys Chem 91:1-20, 2001.*
Farrow et al., Synthesis of a gene for the protein kinase domain of the epidermal growth factor receptor and its expression in *Escherichia coli*, Eur. J. Biochem., 1989, 184(2): 361-5.*
International Preliminary Examination Report for PCT Application No. PCT/JP02/09332, report completed Sep. 11, 2003.
Das et al., "Receptor modulating properties of an antibody directed against the epidermal growth factor receptor," *Eur. J. Biochem.*, 141:429-434 (1984).
Klingbeil et al., "A basic residue, Lys 782, composes part of the ATP-binding site on the epidermal growth factor receptor tyrosine kinase," *Archive of Biochemistry and Biophysics*, 363:27-32 (1999).
Rewcastle et al., "Tyrosine kinase Inhibitors. 12. Synthesis and structure-activity relationships for 6-substituted 4-(phenylamino)pyrimido[5,4-*d*]pyrimidines designed as inhibitors of the epidermal growth factor receptor," *J. Med. Chem.*, 40:1820-1826 (1997).
Traxler et al., "Use of a pharmacophore model for the design of EGFR tyrosine kinase inhibitors: isoflavones and 3-phenyl-4(1-*H*)-qulnolones," *J. Med. Chem.*, 42:1018-1026 (1999).
Supplementary Partial European-Search Report in European Patent Application No. 02 77 2848, dated Jun. 13, 2005.
Yokoyama; "Construction of Artificial Genetic and Cellular Information Processing System"; Japan Science and Technology Corporation, Exploration Research for Advanced Technology (ERATO), pp. 1-24, (Sep. 12, 2001).
Aritomi et al., "Atomic structure of the GCSF-receptor complex showing a new cytokine-receptor recognition scheme," *Nature*, vol. 401, No. 6754, pp. 713-717 (1999).
Degenhardt et al., "Crystallization and preliminary X-ray crystallographic analysis of the EGF receptor ectodomain," *Acta Cryst.*, vol. D54, pp. 999-1001 (1998).

(Continued)

*Primary Examiner*—Kathleen Bragdon
*Assistant Examiner*—Jae W Lee
(74) *Attorney, Agent, or Firm*—Finnegan, Henderson, Farabow, Garrett & Dunner, LLP

(57) ABSTRACT

The present invention relates to a crystal of a complex of an epidermal growth factor (EGF) and an epidermal growth factor receptor (EGFR), a crystal of a complex of EGFR and a substance regulating EGFR activity, structure coordinates of these crystals, a method for screening for the substance regulating EGFR activity, a method for designing the substance regulating EGFR activity, a method for designing an EGFR variant or an EGF variant, a method for producing an EGFR variant or an EGF variant and an EGF variant or an EGFR variant obtainable by such method, a method for designing an epitope using the structure coordinates of the EGF-EGFR complex, a method for producing an anti-EGFR antibody or an anti-EGF antibody and an antibody obtainable by such method, a polypeptide or a salt thereof comprising a region that forms an EGFR dimerization site, and the like.

7 Claims, 30 Drawing Sheets
(18 of 30 Drawing Sheet(s) Filed in Color)

OTHER PUBLICATIONS

Gunther et al., "The secreted form of the epidermal growth factor receptor," *J. Biol. Chem.*, vol. 265, No. 36, pp. 22082-22085 (1990).

Lemmon et al., "Two EGF molecules contribute additively to stabilization of the EGFR dimer," *The EMBP Journal*, vol. 16, No. 2, pp. 281-294 (1997).

Lu et al., "Crystal structure of human epidermal growth factor and its dimerization," *The Journal of Biological Chemistry*, vol. 276, No. 37, pp. 34913-34917 (2001).

Odaka et al., "Ligand-binding enhances the affinity of dimerization of the extracellular domain of the epidermal growth factor receptor," *J. Biochem.*, vol. 122, pp. 116-121 (1997).

Ogiso et al., "Crystal structure of the complex of human epidermal growth factor and receptor extracellular domains," *Cell*, vol. 110, No. 6, pp. 775-787 (2002).

Wiesmann et al., "Crystal structure of nerve growth factor in complex with the ligand-binding domain of the TrkA receptor," *Nature*, vol. 401, No. 6749, pp. 184-188 (1999).

* cited by examiner (Site1)

Fig.9

| Amino acid of Human EGF | Amino acid of Human EGFR | Interaction manner | Contribution to binding (utility value as a pharmacophore) |
|---|---|---|---|
| His10 | Phe357 | | With contribution |
| Asp11 | Ser356 | possible involvement of water molecule | With contribution |
| Tyr13 | Phe357 | π π interaction | With particularly high contribution |
| Leu15 | Leu325<br>Val350 | hydrophobic interaction | With contribution |
| His16 | Gln384 | possible involvement of water molecule | With contribution |
| Ile23 | Leu14<br>Tyr45<br>Ala68<br>Leu69<br>Leu98 | hydrophobic interaction | With high contribution |
| Ala25 | Ala68<br>Leu69<br>Leu98<br>Tyr101 | hydrophobic interaction | With high contribution |
| Leu26 | Leu69<br>Leu98<br>Ala68 | hydrophobic interaction | With high contribution |
| Lys28 | Glu90 | salt linkage | With high contribution |
| Ala30 | | | With contribution |
| Cys31 | Gln16 | hydrogen bond between main chains | With high contribution |
| Asn32 | Gln16 | hydrogen bond between side chains | With high contribution |
| Cys33 | Gly18 | hydrogen bond between main chains | With high contribution |
| Ile38 | Leu17<br>His409 | hydrophobic interaction | With contribution |
| Glu40 | Lys13 | salt linkage | With particularly high contribution |
| Arg41 | Asp355 | salt linkage | With particularly high contribution |
| Gln43 | Leu325 | | With contribution |
| Tyr44 | His346 | possible involvement of water molecule and the like | With contribution |
| Arg45 | Gln384 | hydrogen bond between main chain and side chain | With high contribution |
| Asp46 | Arg29 | salt linkage | With particularly high contribution |
| Leu47 | Leu382<br>Ala415<br>Val417 | hydrophobic interaction | With particularly high contribution |
| Lys48 | Gln411 | possible involvement of water molecule and the like | With contribution |

Fig.10

| Amino acid of Human EGFR | Amino acid of Human EGFR | Interaction manner | Contribution to binding (utility value as a pharmacophore) |
|---|---|---|---|
| Thr249 | Asn86 | hydrogen bond between side chains | with high contribution |
| Tyr246 | Cys283 | hydrogen bond between side chain and main chain | with high contribution |
| Ala286 | Gln252 | hydrogen bond between side chain and main chain | with high contribution |

Fig.11

| Amino acid of Human EGF | Interaction manner | Contribution to binding (utility value as a pharmacophore) | Residues corresponding to the IGF1R modeling structure | Residues corresponding to IR modeling structure | Residues corresponding to ErbB2 modeling structure | Residues corresponding to ErbB3 modeling structure | Residues corresponding to ErbB4 modeling structure |
|---|---|---|---|---|---|---|---|
| Tyr13 | π π interaction | particularly high | Ile340 | Leu377 | Ala386 | Trp373 | Tyr378 |
| Ile23 | hydrophobic interaction | high | Ile9<br>Leu33<br>Phe58<br>Val60<br>Phe90 | Ile40<br>Leu64<br>Phe91<br>Val93<br>Phe123 | Leu33<br>Tyr64<br>Ala87<br>His88<br>Leu117 | Leu36<br>Leu67<br>Ala90<br>Met91<br>Met120 | Leu36<br>Ser67<br>Ala90<br>Leu91<br>Phe120 |
| Ala25 | hydrophobic interaction | high | Phe58<br>Val60<br>Phe90<br>Thr93 | Phe91<br>Val93<br>Phe123<br>Val126 | Ala87<br>His88<br>Leu117<br>Gly120 | Ala90<br>Met91<br>Met120<br>Tyr123 | Ala90<br>Leu91<br>Phe120<br>Tyr123 |
| Leu26 | hydrophobic interaction | high | Phe58<br>Val60<br>Phe90 | Phe91<br>Val93<br>Phe123 | Ala87<br>His88<br>Leu117 | Ala90<br>Met91<br>Met120 | Ala90<br>Leu91<br>Phe120 |
| Lys28 | salt linkage | high | Phe82 | Phe116 | Glu109 | Asp112 | Glu112 |
| Cys31 | hydrogen bond between main chains | high | Asn11 | Asn42 | Leu35 | Val38 | Ser38 |
| Asn32 | hydrogen bond between side chains | high | Asn11 | Asn42 | Leu35 | Val38 | Ser38 |
| Cys33 | hydrogen bond between main chains | high | Asp12 | Asn43 | Ala37 | Gly40 | Ser40 |
| Glu40 | salt linkage | particularly high | Asp8 | Asp39 | Lys32 | Gly35 | Lys35 |
| Arg41 | salt linkage | particularly high | Asn339 | Asn375 | Asp384 | Asp371 | Asp376 |
| Gln43 | | with contribution | | | Arg354 | Val343 | Gln346 |
| Tyr44 | possible involvement of water molecule and the like | with contribution | | | Ala375 | Asp362 | Ile367 |
| Asp46 | salt linkage | particularly high | Arg18 | Glu49 | His48 | Lys51 | Lys51 |
| Leu47 | hydrophobic interaction | particularly high | Ala365<br>Tyr391<br>Leu393 | Ala402<br>Tyr428<br>Leu430 | Tyr411<br>Thr444<br>Gln446 | Asn398<br>Leu431<br>Met433 | Asn403<br>Ile436<br>Lys438 |

EGR-EGFR COMPLEX

CROSS REFERENCE TO RELATED APPLICATIONS

This application is a National Phase Application based on PCT/JP02/09332, filed Sep. 12, 2002, the content of which is incorporated herein by reference, and claims the priority of Japanese Patent Application No. 2002-28780, filed Feb. 5, 2002.

TECHNICAL FIELD

The present invention relates to a crystal of the complex of epidermal growth factor (hereinafter, it may be referred to as "EGF" or "EGF ligand") and epidermal growth factor receptor (hereinafter, it may be referred to as "EGFR" or "EGF receptor") and a crystal of the complex of EGFR and a substance regulating EGFR activity; a method for crystallizing the complex of EGFR and the substance regulating EGFR activity (particularly, EGF) that can be subjected to X-ray crystal structure analysis; structure coordinates of the complex of EGFR and the substance regulating EGFR activity (particularly, EGF) that is obtainable by structurally analyzing the crystal; a method for screening for and a method for designing the substance regulating EGFR activity using the structure coordinates; a method for identifying an EGF-EGFR binding site or an EGFR dimerization site in the EGF-EGFR complex; a method for designing a pharmacophore of the substance regulating EGFR activity; a method for screening for and a method for designing the substance regulating EGFR activity using the pharmacophore of the substance regulating EGFR activity and an EGFR antagonist that fits pharmacophores; a method for inhibiting EGFR activity using an EGFR antagonist; a method for designing and a method for producing an EGFR variant using the structure coordinates of the EGF-EGFR complex, an EGFR variant obtainable by the production method; a method for designing and a method for producing an EGF variant using the structure coordinates of the EGF-EGFR complex and the EGF variant obtainable by the production method; a method for obtaining structure coordinates of a protein with an unknown structure using the structure coordinates of the EGF-EGFR complex and the structure coordinates obtainable by such method; a method for designing an epitope using the structure coordinates of the EGF-EGFR complex; a method for producing an anti-EGFR antibody and an anti-EGFR antibody obtainable by such method; a method for producing an anti-EGF antibody and an anti-EGF antibody obtainable by such method; a polypeptide containing a region that forms an EGFR dimerization site or a salt thereof; and the like.

BACKGROUND ART

Epidermal growth factor receptor (EGFR) is a member of the receptor tyrosine kinase superfamily. EGFR is known to be involved in regulation of cell proliferation, maturation, and differentiation (Carpenter, G. & Cohen, S. J. Biol. Chem. 265, 7709-7712 (1990)).

Binding epidermal growth factor (EGF) to the extracellular domain of EGFR is thought to induce receptor dimerization, which brings the cytoplasmic tyrosine kinase domain of the two receptors into close proximity, resulting in the activation of intrinsic tyrosine kinase receptors in the intracellular domain, followed by the activation of numerous downstream signal pathways (Schlessinger, J. Cell 103, 211-225 (2000)). Besides this activation mechanism, it has been recently demonstrated that a portion of EGFR activated by EGF is translocated to a nucleus so that it might function as a transcription factor to activate genes required for high-level proliferation activities (Lin, S. Y. et al., Nat. Cell Biol. 3, 802-808 (2001)). In the meantime, spontaneous oligomerization accompanied by tyrosine phosphorylation has been reported for oncogenic mutants lacking either a portion or most of the extracellular domain (Haley, J. D. et al., Oncogene 4, 273-283 (1989); Huang, H. S. et al., J. Biol. Chem. 272, 2927-2935 (1997)). The extracellular domain also likely plays a critical role in suppression of ligand-dependent spontaneous oligomerization.

Three homologues of EGFR (ErbB-2, ErbB-3, and ErbB-4) have been identified in humans. Numerous studies have demonstrated that, in addition to homo-dimerization, these EGF ligands also induce a combinational hetero-oligomerization of different pairs of the EGFR family members (Olayioye, M. A. et al., Embo J. 19, 3159-3167 (2000)).

The three-dimensional structure of a human EGF monomer has been analyzed using high-resolution NMR (J. Mol. Biol. (1992) 227, 271-282). As a result, 2 helical segments (Leu8-Tyr13 and Leu47-Glu51) have been discovered. The first segment has been reported to form a major β-sheet via disulfide bridges (Cys6-Cys20 and Cys14-Cyh31), and the second segment has been reported to form a type II turn on the C-terminus of the protein. This helix has been reported to show amphipathic features with Leu47, Trp50, Trp49, and Leu52 on the hydrophobic surface, and Lys48 and Glu51 on the hydrophilic surface. This helix is thought to participate in the formation of a hydrophobic core (Val34, Arg45, and Trp50) in the periphery of Tyr37, which is a conserved residue. In recent years, analytical results achieved using NMR on EGF dimerization have been reported (J. Biol. Chem (2001) 276, 34913-34917). As a result, 3 disulfide bridges (Cys6-Cys20, Cys14-Cys31, and Cys33-Cys42) have been confirmed, and it has been revealed that it consists of an N-domain (residues 1-32) and a C-domain (residues 33-53). The N-domain has been reported to have an irregular N-terminal peptide segment (residues 1-12) and an anti-parallel β-sheet (residues 19-23 and residues 28-32). In addition, the C-domain has been reported to contain a short anti-parallel β-sheet (residues 36-38 and residues 44-46) and a C-terminal segment (residues 48-53).

Furthermore, research has been conducted on mutation of Arg41 and Leu47. As a result, it is known that these residues are essential for the binding of EGF with its receptor, and substitution of arginine with lysine is not allowed (Mol. Cell. Biol (1989) 9, 4083-4086; FEBS Letters (1990) 261, 392-396; FEBS Letters (1990) 271, 47-50; Biochemistry (1991) 30, 8891-8898; Proc. Nat. Acad. Sci., USA (1989) 86, 9836-9840). This indicates that the arginine side chain of EGF (guanidino group) participates in specific interaction with EGFR. In addition, research has been conducted with point mutation, where altered amino acids have been prepared for Ile23, Ala25, Leu26, Ala30, and Asn32, and experiments and studies have been conducted using them, suggesting that each residue may be an amino acid directly interacting with EGFR. However, though amino acid residues important for the interaction are increasingly presumed by point mutation experiments, information needed for industrial application has not yet been obtained in the current situation because the active conformation of the amino acid side chains, the mode of interaction with EGFR, and the active conformation of the EGFR amino acid side chains are unknown.

Regarding EGFR, although efforts have been made to elucidate the crystal structure, such elucidation has not yet been achieved (J. Biol. Chem (1990), 265, 22082-22085; Acta Crystallogr D Biol Crystallogr (1998) 54, 999-1001), and the three-dimensional structure has been merely modeled by homology modeling (Biochim. Biophys. Acta (2001) 1550, 144-152). In this report, the model structure of EGFR has been built using an insulin receptor and a lymphocyte protein-tyrosine kinase as templates. Moreover, there is a report in which IGF-1R (insulin-like growth factor-1 receptor) has been used as a template (Jorissen R. N. et al., Protein Sci. 2000, 9(2), 310-324; WO 99/62955).

The point mutation experiment conducted by causing mutation of Glu367, Gly441, and Glu472 to result in Lys has revealed that mutations of Glu367Lys and Glu472Lys do not affect the binding with ligands. On the other hand, the mutation of Gly441Lys has been reported to significantly reduce the affinity with EGF (Biochemistry (2001) 40, 8930-8939).

Currently, the development of drug candidate compounds targeting EGFR is in progress (Drugs 2000; Vol. 60 Suppl. 1: 15-23, Clinical Cancer Research 2001; Vol. 7: 2958-2970). Furthermore, many low molecular inhibitors suppressing the kinase activity in the intracellular domain of EGFR have been reported (Drugs 2000; Vol. 60 Suppl. 1: 25-32). However, among low molecular weight compounds, neither medicaments that selectively promote activation by binding to EGFR extracellular domain, nor medicaments that selectively inhibit activation have been marketed as drugs. In general, compared with antibodies and recombinant protein pharmaceutical preparations, the agonists and the antagonists of the low molecular weight compounds can be orally administered in many cases, so that they are more useful as drugs. Therefore, lowering the molecular weight of a protein pharmaceutical preparation has been attempted for many diseases. However, the development of such a preparation generally necessitates further trial and error, so that the development of a drug useful for patients always requires a long time and a high cost. Furthermore, regarding an antagonist targeting an intracellular kinase domain, it is predicted that the backbone is limited because the antagonist needs to permeate a cell membrane, and an excessive dose thereof is required. In addition, there are no experimental three-dimensional structures (crystal structures or NMR structures) of EGFR kinase domains, so that many inductions and syntheses on a trial-and-error basis are required for the provision of selectivity. Moreover, antagonists acting on an ATP binding region intramolecularly contain a pharmacophore having ATP-like chemical properties in many cases. Thus, such an antagonist will often be a nucleic acid analogue in terms of the properties of a compound, and future side effects pose difficulties.

SUMMARY OF THE INVENTION

Under such circumstances, technology for mimicking interaction sites between EGF and EGFR has been eagerly desired in order to discover a low molecular weight compound that inhibits the interaction between EGF and EGFR or a low molecular weight compound that selectively binds with and activates an EGFR extracellular domain and transduces an EGF signal. Construction and design of EGFR agonists and EGFR antagonists or agonist antibodies and antagonist antibodies by molecular design techniques enable preparation of drugs selective against EGF/EGFR far more reasonably than conventional techniques. For such molecular design based on structure information or computer screening based on structure information, the experimental structure and the analytical results regarding the EGF-EGFR complex have a very important meaning.

However as described above, regarding EGF ligands, although the structures of monomers or homodimers have been obtained based on NMR structures, the active conformation of the amino acid side chains or the main chain upon binding with EGFR is unknown. In the case of EGFR, the EGFR structure in an unliganded state has been merely predicted by modeling. Furthermore, the structure of the EGF-EGFR complex has been completely unknown. It has been impossible to infer active conformation when the two bind to each other and are activated based on the receptor structure in an unliganded state and the ligand structure of a simple substance. Hence, inventions relating to the specification of pharmacophores obtained by analysis of the crystal structure of the EGF-EGFR complex and the interaction site thereof and techniques for molecular designing have been extremely desired.

As a result of intensive studies to solve the above problems and to provide a good EGFR agonist or a good EGFR antagonist, we have succeeded in establishing a technique for crystallizing EGF-EGFR complexes whose three-dimensional structure can be specified by X-ray crystal structure analysis. We have revealed the structure coordinates of the complex using such crystal, which many researchers have attempted but none of them have achieved. Through further analysis thereof, we have completed the present invention by providing a method for screening for and a method for designing the substance regulating EGFR activity; a method for identifying an EGF-EGFR binding site or an EGFR dimerization site in the EGF-EGFR complex; a method for designing a pharmacophore of the substance regulating EGFR activity (particularly, EGF); a method for screening for and a method for designing the substance regulating EGFR activity using the pharmacophore of the substance regulating EGFR activity and an EGFR antagonist that fits pharmacophores; a method for inhibiting EGFR activity using an EGFR antagonist; a method for designing and a method for producing an EGFR variant using the structure coordinates of the EGF-EGFR complex, an EGFR variant obtainable by the production method; a method for designing and a method for producing an EGF variant using the structure coordinates of the EGF-EGFR complex and the EGF variant obtainable by the production method; a method for obtaining structure coordinates of a protein with an unknown structure using the structure coordinates of the EGF-EGFR complex and the structure coordinates obtainable by such method; a method for designing an epitope using the structure coordinates of the EGF-EGFR complex; a method for producing an anti-EGFR antibody and an anti-EGFR antibody obtainable by such method; a method for producing an anti-EGF antibody and an anti-EGF antibody obtainable by such method; a polypeptide containing a region that forms an EGFR dimerization site or a salt thereof; and the like.

The present invention is explained in detail as follows.

1. Crystal and Method for Producing Crystal

The present invention provides a crystal of the EGF-EGFR complex. The crystal is characterized in that EGF binds to EGFR at a 1:1 ratio, and the EGF-bound EGFRs (wherein each EGFR protein is in a state of being bound with each EGF protein) form a dimer. More specifically, the EGF-bound EGFR is dimerized by receptor-to-receptor binding not via EGF. The EGF-bound EGFR is, as shown in FIG. 1a, dimerized via domain II of EGFR, and more specifically, via each region consisting of $240^{th}$ to $267^{th}$ amino acids of the amino acid sequence of human EGFR shown in SEQ ID NO: 1. Moreover, EGF interacts with domains I and III of EGFR. Domains I and III of each EGFR curve to the other side of a dimerization site while holding EGF between domains. Any crystals of EGF-EGFR complexes having such a feature are encompassed in the scope of the present invention. In the EGF-EGFR complex, the interaction site of EGF and EGFR is referred to as an "EGF-EGFR binding site" and a site where EGF-bound EGFR interacts with EGF-bound EGFR to be dimerized is referred as a "dimerization site" or an "EGFR dimerization site." Moreover, in the case a ligand-receptor complex that is formed in a mechanism similar to that of EGF/EGFR, an interaction site of the ligand with the receptor is similarly referred to as a "ligand-receptor binding site" and a site where the ligand-bound receptors interact with each other to be dimerized is referred to as a "dimerization site" or a "receptor dimerization site."

EGF and EGFR used in the present invention are derived from a mammal, preferably a mouse or a human, and particularly preferably a human. The amino acid sequences of EGF and EGFR are known. Human EGF (mature peptide) has been registered with the NCBI Protein DB under the accession number AAA72173 (SEQ ID NO: 2). Mouse EGF has been registered with the NCBI Protein DB under accession number NP_034243. Rat EGF has been registered with the NCBI Protein DB under accession number NP_036974. Human EGFR has been registered with the NCBI Protein DB under the accession number NP_005219 (SEQ ID NO: 15). Mouse EGFR has been registered with the NCBI Protein DB under the accession number CAA55587. Rat EGFR has been registered with the NCBI Protein DB under the accession number AAF14008. For EGF and EGFR derived from other species, sequence information can be obtained from known databases.

Furthermore, under conditions where the function is maintained, a protein consisting of an amino acid sequence derived from a native amino acid sequence by deletion, substitution and/or insertion of 1 or more, preferably 1 or several amino acids, or a protein to which an amino acid(s) is added to the N-terminus and/or the C-terminus is also encompassed. Generally, it is considered that such a slight difference in the primary structure will not largely affect the entire three-dimensional structure, and the function is maintained. The full-length amino acid sequence of human EGFR is shown in SEQ ID NO: 15. Since a region consisting of the 1st to the 24th amino acids of the amino acid sequence shown in SEQ ID NO: 15 is removed as a signal sequence, native mature human EGFR is composed of the 25th to the 1210th amino acids of the amino acid sequence shown in SEQ ID NO: 15.

As EGFR, extracellular domain of EGFR are preferably used. EGFR has a structure penetrating one time a cell membrane, and is composed of, from the N-terminus, the extracellular domain, a transmembrane region, and an intracellular domain having tyrosine kinase region and autophosphorylation sites. Furthermore, the extracellular domain is composed of 4 domains (from the N-terminus, referred to as domain I, domain II, domain III, and domain IV, or also referred to as L1, S1, L2, and S2 domains, respectively) (Bajaj, M. et. al. Biochim. Biophys. Acta 916, 220-226 (1987)). Domain I of human EGFR is composed of the 1st to the 165th amino acids of the amino acid sequence of mature human EGFR, domain II is composed of the 166th to the 312nd amino acids of the same, domain III is composed of the 313rd to the 512nd amino acids of the same, and domain IV is composed of the 513rd to the 619th amino acids of the same. It has been revealed according to the present invention, domains I, II, and III of EGFR participate in the formation of EGF-EGFR complex. Hence, as EGFR, extracellular domain including at least domain I, domain II, and domain III are preferably used.

1-1 Protein Purification

Collection sources of EGF to be used for crystal structure analysis in the present invention are not specifically limited, but the liver, the spleen, or the kidney of pigs, rats, bulls, and the like can be used. In addition, EGF can also be collected from an extracted human liver or the like. EGF is collected by homogenizing the above collection sources, and then purifying soluble components by several types of column chromatography. Furthermore, through the use of genetic engineering techniques, it is also possible to cause a gene encoding EGF to be expressed by bacteria, animal cells or the like, and thus to produce the EGF in large quantities. For example, EGF can be obtained by introducing a recombinant DNA having an EGF gene incorporated therein into a host such as *Escherichia coli*, yeast, a Chinese hamster ovary (CHO) cell, and the like in a manner that enables the expression of the EGF gene to obtain a transformant, and then culturing the transformant.

When a bacterium such as *Escherichia coli* is used as a host, the recombinant DNA containing an EGF gene is required to be able to replicate autonomously in the cell. Moreover, a transcription promoter, an SD sequence as a ribosome RNA-binding region, or the like may be ligated. A transcription terminator or the like can also be inserted appropriately. A recombinant vector can be easily transferred into a host by, for example, a method using a commercially available kit.

EGF can be obtained by culturing the above transformant and then collecting the EGF from the culture. The "culture" means the culture supernatant as well as any of cultured cells or cultured microorganisms, or the crushed product of cells or microorganisms. The culture method is conducted according to a general method used in culturing hosts. For example, when CHO cells are used as a host, the cells are cultured in media that are generally used for animal cells under conditions of 5% $CO_2$ and 37° C. Upon culture, bovine serum and antibiotics may be added to the media if necessary.

After culture, when EGF is produced within microorganisms or within cells, target EGF is collected by disrupting the microorganisms or the cells by homogenizer treatment or the like. Subsequently, EGF is isolated and purified from the above culture using various types of chromatography, or the like, preparing a sample.

EGFR can also be obtained according to the isolation and purification methods employed for EGF. In addition, a commercially available gene recombinant EGF or EGFR can also be used.

To prepare the complex of EGF and EGFR, purified EGF is dissolved in a solution of purified EGFR. Dimers are prepared by binding the complexes of EGF and EGFR in a reaction system where EGF and EGFR are mixed.

An amino acid sequence of EGFR suitable for use in preparing the crystal of the present invention is shown in SEQ ID NO: 1, and an amino acid sequence of EGF suitable for use in the same is shown in SEQ ID NO: 2. A region consisting of the 1st to the 619th amino acids of the amino acid sequence of SEQ ID NO: 1 corresponds to a region consisting of the 1st to the 619th amino acids of native mature human EGFR (corresponding to the 25th to the 643rd amino acids of the amino acid sequence shown in SEQ ID NO: 15). A region consisting of the 620th to the 633rd amino acids of the amino acid sequence of SEQ ID NO: 1 contains a FLAG tag for purification. However, examples of the amino acid sequence are not limited to these amino acid sequences. An amino acid sequence that is derived from any one of the above amino acid sequences by mutation such as deletion, substitution, addition, or the like of 1 or more (e.g., 2 to 10) amino acids and has EGFR activity or EGF activity can also be used in the present invention. "EGFR activity" means activity capable of at least binding to EGF, and more preferably means activity of binding to EGF whereby dimerization is then induced. "EGF activity" means activity capable of at least binding to EGFR, and more preferably means activity of binding to EGFR and inducing EGFR dimerization by such binding. For example, an amino acid sequence of EGFR that can be used herein has an amino acid sequence composed of the region consisting of the 25th to the 643rd amino acids of the amino acid sequence shown in SEQ ID NO: 15 extended by the addition of 1 or more amino acids to the N-terminus and/or the C-terminus.

In addition, the above amino acid can be mutated by a site-directed mutagenesis method known by persons skilled in the art, and a kit therefor can be used (e.g., Mutan-G and Mutan-K (both produced by TAKARA SHUZO CO., LTD.)).

The present invention also provides a method for producing crystallizable EGFR. The production method comprises:
(A) a step of producing an EGFR protein using Lec8 cells; and
(B) a step of deglycosylating the EGFR protein using glycosidase.

The method may further comprise (C) a step of roughly purifying the EGFR protein by salting out. We have revealed that 10 N-type sugar chains bind to the extracellular domain of EGFR, and one of these sugar chains is difficult to remove by glycosidase treatment. Based on this finding, we have discovered that the use of Lec8 cells (ATCC CRL-1737), which are cells producing proteins having terminal sialic-acid and galactose-residue-deficient N-binding oligosaccharides, is efficient for producing crystallizable EGFR. Furthermore, we have discovered that rough purification using salting out is efficient when the EGFR protein produced using the Lec8 cells is purified. It is preferable to use ammonium sulfate precipitation for salting out. Specific examples of glycosidase include endoglycosidase D and endoglycosidase H. The present invention also provides crystallizable EGFR that is obtainable by the above production method. Such EGFR is characterized by possessing at least activity of binding to EGF. As long as EGFR possesses at least the activity of binding to EGF, examples of such EGFR include a protein consisting of an amino acid sequence derived from the native amino acid sequence by deletion, substitution, and/or insertion of 1 or more, and preferably 1 or several amino acids, or a protein comprising an amino acid sequence derived from the native amino acid sequence by addition of an amino acid(s) to the N-terminus and/or the C-terminus. Moreover, the crystallizable EGFR of the present invention preferably has quality that is sufficient to give a resolution of at least 10 Å, preferably 4.0 Å or less, and more preferably 3.5 Å or less when crystals obtained using the EGFR proteins (may be crystals of EGFR alone, or crystals of the complex of EGFR and a substance regulating EGFR activity) are subjected to X-ray crystal structure analysis.

EGFR obtainable by the above method can be used in the method of the present invention for crystallizing an EGF-EGFR complex or the complex of EGFR and a substance regulating EGFR activity. By the use of EGFR, crystals can be easily obtained.

1-2 Preparation of Protein Crystals

Subsequently, a crystal of the EGF-EGFR complex is prepared. As a method for crystallizing proteins, general protein crystallization techniques such as a vapor diffusion method, a batch method, a dialysis method, or the like can be used. Determination of physical and chemical factors such as protein concentration, salt concentration, pH, types of a precipitating agent, and temperature is important in protein crystallization, and the determination of these factors is generally known by persons skilled in the art. Hence, to efficiently examine a plurality of parameters (e.g., precipitating agent, pH, and salt concentration), it is preferred to produce phase diagrams. Once crystals have been precipitated, the parameters are further minutely varied so as to refine conditions where the best crystals can appear.

(1) The "vapor diffusion method" involves placing a droplet of a protein solution containing a precipitating agent in a container that contains a buffer (external solution) containing a precipitating agent with a higher concentration, sealing the container, and then allowing to stand. Depending on how the droplet is placed, the hanging drop method and the sitting drop method may be used. In the present invention, either of these methods can be employed. The hanging drop method involves spotting a small droplet of a protein solution onto a cover glass and inverting the cover glass over a reservoir so as to seal the reservoir. The sitting drop method involves placing an appropriate droplet stand within a reservoir, spotting a small drop of a protein solution on the droplet stand, and then sealing the reservoir using a cover glass or the like. In this case, it is preferred that the solution in the reservoir contains a precipitating agent, and the precipitating agent is contained in a small drop of protein in a small quantity.

Any appropriate solutions of precipitating agents to be used in the vapor diffusion method can be prepared by persons skilled in the art. For example, a precipitating agent may be prepared so as to contain the following components (a) to (c).
(a) Precipitating agent: molecular weight between 400 and 2000, polyethylene glycol (PEG) at a concentration between 0% and 50% by weight or ammonium sulfate, MPD (methylpentane diol), or the like
(b) Addition salt: NaCl, lithium chloride, magnesium chloride, or the like at a concentration between 0.1 M and 0.3 M
(c) Buffer agent: sodium phosphate, potassium phosphate, tris-HCl, or the like In addition, components used herein are not limited to the above components, and components generally used by persons skilled in the art can be used appropriately.

(2) The "batch method" involves adding the solution of a precipitating agent to a protein solution in driblets so as to make the solution slightly muddy, removing insoluble matters by centrifugation, putting the supernatant in a small test tube, sealing the tube, and then allowing the resultant to stand.

(3) The "dialysis method" involves dialyzing a protein solution against a buffer (external solution) containing a precipitating agent using a semipermeable membrane.

In protein crystallization, it is essential to conduct crystallization under conditions where complexes or dimers are maintained. In the present invention, the EGF/EGFR crystals can be precipitated by adding a precipitating agent to a solution (protein solution) containing EGF and EGFR dissolved therein. Examples of solvents for the above protein solution are water, a buffer, and the like. As a buffer, for example, 0.2 M Tris-HCl (pH 8.0), approximately 0.1 M NaCl, or the like can be used. "By adding" also means by bringing a protein solution into contact with a buffering agent solution. For example, in the case of the EGF-EGFR complex, crystals appropriate for X-ray crystal analysis can be obtained by the vapor diffusion method under conditions of pH=7.0-9.0, protein concentration between 3 and 15 mg/ml, and temperature at 20° C. using polyethylene glycol as a precipitating agent. However, examples of conditions are not limited to the above conditions. The method for producing crystals of the present invention preferably comprises a step of sugar chain treatment in a purification process for EGFR.

Furthermore, the present invention provides a method for producing a crystal of a complex of EGFR and a substance regulating EGFR activity. The production method comprises the following steps of: (A) producing crystallizable EGFR; and (B) bringing EGFR into contact with a substance regulating EGFR activity. A typical example of the substance regulating EGFR activity is EGF, but is not limited thereto. The substance regulating EGFR activity may be any of a peptide, an oligonucleotide, a synthetic compound, or a compound derived from nature, as long as it is an EGFR agonist or an EGFR antagonist (described later). The substance regulating EGFR activity can be prepared by a technique known in the art. The crystal production method can further comprise (C) a step of crystallizing a complex of EGFR and the substance regulating EGFR activity. The complex can be crystallized by employing a general protein crystallization technique such as the above vapor diffusion method, the batch method, or the dialysis method.

The step (C) can further comprise: (C-1) a step of bringing a solution containing EGFR and the substance regulating EGFR activity into contact with a solution containing a precipitating agent; (C-2) a step of generating a crystal; and (C-3) a step of isolating the crystal. The step of bringing a solution containing EGFR and the substance regulating EGFR activity into contact with a solution containing a precipitating agent can be conducted by contact via a dialysis membrane, contact via a sealed space in the hanging drop method, mixing of solutions, or the like. The step of generating a crystal can be realized by creating a supersaturation state of a protein due to slowly increased concentrations of the protein or the precipitating agent in the solution containing EGFR and the substance regulating EGFR activity. Furthermore, the step can also be realized by introducing a seed crystal into a protein solution.

1-3 X-Ray Crystal Diffraction

The X-ray crystal structure analysis technique is most commonly used as a technique for elucidating the three-dimensional structure of a protein. Specifically X-ray structure analysis involves crystallizing a protein, exposing the crystal to monochromatized X-rays, and then, based on the thus obtained diffraction images obtained with X-rays, elucidating the three-dimensional structure of the protein. The present invention provides a method for determining structure coordinates of a complex of EGFR and a substance regulating EGFR activity. The method comprises the following steps of:

(A) producing a crystal of a complex of EGFR and a substance regulating EGFR activity; and
(B) obtaining structure coordinates of the complex of EGFR and the substance regulating EGFR activity by X-ray crystal structure analysis using the crystal obtained by (A).

The step (A) is as explained in "1-2" above. The step (B) can further comprise: (b-1) a step of obtaining diffraction data by irradiating the crystal obtained by (A) with X-rays; (b-2) a step of obtaining an electron density map of the complex by the analysis of the diffraction data obtained by (b-1); and (b-3) a step of obtaining the structure coordinates of the complex by the analysis of the electron density map obtained by (b-2). The crystal structure of the complex can be analyzed using an X-ray diffractometer in a laboratory or a large-scale synchrotron radiation facility (e.g., ESRF, APS, SPring-8, PF, ALS, CHESS, SRS, LLNL, SSRL, or Brookhaven), and collecting diffraction data using a two-dimensional detector such as an imaging plate or a CCD camera by an oscillation photography method or a Laue method, so that the three-dimensional structure of the complex can be revealed from the data by X-ray crystal structure analysis. Specifically, the diffraction images collected by X-ray diffraction experiments are processed with data-processing software, so as to be able to calculate the diffraction intensity obtained using indices of individual diffraction spots and integration. By conducting inverse Fourier transform using the diffraction intensities and the phase information of these diffraction spots, electron density in a three-dimensional space is obtained. However, in diffraction experiments, it is impossible in principle to measure information of the phase of each diffraction spot required for the calculation of electron density. Hence, to obtain electron density, the phase which is missing information is inferred by a molecular replacement method, a multiple isomorphous replacement method, a multiple wavelength anomalous dispersion method (MAD method), or modified methods thereof. In accordance with the thus obtained electron density map, a three-dimensional model is built using software that runs on a graphics workstation. After building the model, the structure is refined by a least squares method, a maximum likelihood method, a Simulated Annealing method, or the like, thereby obtaining the final three-dimensional structure of the complex.

In the MAD method, synchrotron radiation is used, and the diffraction data of crystals are measured by varying incident X-ray wavelengths. Synchrotron radiation that can be used in the MAD method can be generated by, for example, structural biological beam line I (BL41XU) of SPring-8 large-scale synchrotron radiation facility.

Protein crystals are often damaged by X-ray irradiation, and diffraction ability becomes deteriorated. Thus, it is preferred to conduct high-resolution X-ray diffraction by low-temperature measurement. The low-temperature measurement is a method that involves rapidly cooling and freezing crystals at approximately −173° C., and then collecting diffraction data under such state. Generally when protein crystals are frozen, treatment or the like with a solution containing a protectant such as glycerol is devised for the purpose of preventing crystal decay by freezing. Frozen crystals can be prepared by, for example, immersing crystals in a stock solution supplemented with a protectant, and then directly immersing the crystals in liquid nitrogen so as to freeze the crystals instantly.

In the present invention, the crystal of the complex of EGFR and the substance regulating EGFR activity, such as a dimer formed of EGF-EGFR complexes bound to each other, are X-ray diffracted using an appropriate X-ray source.

X-ray diffraction data are collected with crystals that diffract to at least resolutions of 10 Å or less, preferably 4.0 Å or less, and more preferably 3.5 Å or less so as to be able to analyze in detail the three-dimensional structure of the complex.

We have analyzed the crystal structure of the complex of EGF and EGFR using a crystal structure analysis technique using X-rays. The crystal of a complex of EGF having the amino acid sequence shown in SEQ ID NO: 2 and EGFR having the amino acid sequence shown in SEQ ID NO: 1 belongs to space group $P3_121$ and has a size in terms of unit cell parameters: a=220.2±1.5 Å, b=220.2±1.5 Å, and c=113.1±1.5 Å in the directions of the a, b, and c axes, respectively. Specifically, the crystal of the EGF-EGFR complex of the present invention is characterized in that the unit cell parameters are a=220.2±1.5 Å, b=220.2±1.5 Å, and c=113.1±1.5 Å. Furthermore, using the technique of crystal structure analysis by X-ray diffraction using the crystal of the complex, the three-dimensional structure coordinates (values indicating the spatial and positional relationship of respective atoms) of the complex of EGF and EGFR are obtained. The thus obtained structure coordinates are represented according to a notation method that is generally employed by persons skilled in the art for the three-dimensional structure coordinates of a protein and are shown in Table 1 and Table 2. Table 1 shows structure coordinates as determined with 3.5 Å resolution, and Table 2 shows structure coordinates as determined with 3.3 Å resolution.

Data in Table 1 and Table 2 are presented according to the format of the protein data bank (PDB). The PDB format contains, for example, coordinates of each atom composing a relevant protein molecule, and is a standard format for handling the coordinates of biological molecules. Among symbols or numerals used in Table 1 or Table 2, "ATOM" as recorded in the column on the left-most side (the first column) indicates each atom represented by atomic coordinates. "HETATM" in Table 2 indicates the same, except for indicating that an atom denoted in the line does not belong to an amino acid (e.g., NAG or water molecule). "TER" indicates the C-terminus of a peptide chain. Numerals in the column (the second column) to the right of this column are atom serial numbers (1-8767 or 1-8896), and Roman letter recorded in the column (the third column) to the right side of this column indicate types of atom (see below).

C: a carbon atom of an amino acid residue
N: a nitrogen atom of an amino acid residue
O: an oxygen atom of an amino acid residue
S: a sulfur atom of an amino acid residue Roman letters (e.g., A, B, D, and G) recorded together to the right side of the above atoms indicate the positional relationship of the atoms. For example, the Roman letters are recorded as CA, CB, NE, NZ, OE, SG, and the like.

Furthermore, Roman letters recorded in the column (the fourth column) to the right side of the Roman letters indicating types of the above atoms indicate amino acid residues to which the atoms belong, and are denoted by a three letter code (e.g., "GLU," "LYS," and "VAL"). "NAG" of atom serial number 8614 and the following atom serial numbers indicate N-acetylglucosamine. "TIP" indicates a water molecule. Roman letters (A, B, C, and D) in the column (the fifth column) to the right side of this column are identification symbols for protein chains, each of which represents EGFR1, EGFR2, EGF1, and EGF2. Numerals recorded in the column (the sixth column) to the right side of this column indicate amino acid residue numbers numbered from the N-terminus. Amino acid residue numbers of EGFR correspond to those of the amino acid sequence described in SEQ ID NO: 1. Amino acid residue numbers of EGF correspond to those of the amino acid sequence described in SEQ ID NO: 2. Furthermore, columns ranging from the column (the seventh column) to the right side of these numerals to the ninth column indicate in turn X-coordinates ("a" coordinates) (Angstrom units), Y-coordinates ("b" coordinates) (Angstrom units), and Z-coordinates ("c" coordinates) (Angstrom units). Columns ranging from the column (the tenth column) to the right side of the ninth column to the right-most column (the twelfth column) indicate in turn occupancy (e.g., "1.00"), isotropic temperature factor (for example, 120.73 in the case of atom serial number 1, and 131.35 in the case of atom serial number 2) in Table 1, and atom number or atom symbol (e.g., 6:C, 7:N, 8:O, and 16:S).

Lengthy table referenced here

US07514240-20090407-T00001

Please refer to the end of the specification for access instructions.

Lengthy table referenced here

US07514240-20090407-T00002

Please refer to the end of the specification for access instructions.

2. Structure Coordinates of EGF-EGFR Complex

The present invention provides structure coordinates of an EGF-EGFR complex, and specifically, structure coordinates of a crystal of the EGF-EGFR complex, which are obtained by X-ray crystal structure analysis using the crystal of the EGF-EGFR complex having the following characteristics (A) and (B):
(A) EGF binds to EGFR at a 1:1 ratio; and
(B) the EGF-bound EGFRs form a dimer.

In the present invention, "structure coordinates" are mathematical coordinates deduced by numerically expressing the diffraction intensity at individual diffraction spots obtained by X-ray diffraction resulting from electrons contained in the atoms of crystallized proteins, and then analyzing the numerical data. The structure is represented by three-dimensional coordinates of the positions of the atoms of the above proteins. Specifically, the structure coordinates actually indicate spatial arrangement defined by each distance between molecules (atoms) composing a chemical structure. To process the spatial arrangement data as information on a computer, relative arrangement data are processed into numerical information (generation of coordinates) as specific coordinates in a coordinate system. This process is required for convenient computer processing. The real nature of the structure coordinates is, as shown above, arrangement defined by the distance between respective molecules (atoms), and should not be understood as coordinate values that are temporally specified upon computer processing. Furthermore, in this specification, atomic coordinates indicate coordinates of individual atoms composing a substance (e.g., a protein or an amino acid).

We have crystallized the extracellular domains of EGFR forming complexes with EGF and analyzed such crystal by X-ray crystallography, so as to elucidate the mechanism whereby the binding of EGF ligands induces dimerization and activation of the receptors. Thus, we have succeeded in analyzing the crystal structures of domains I, II, and III among the extracellular domains of human EGFR complexed to human EGF at 3.5 Å resolution and 3.3 Å resolution. According to the analytical results, it has been revealed that 2 receptors (EGFR) separately form complexes with ligands (EGF). The complexes are in a form wherein each ligand is captured between the surfaces of domains I and III of each receptor. Moreover, a dimer is formed by interaction between 2 loops extruding from domain II of each receptor, and is stabilized. The formation of the above dimer shows the structural mechanism for EGF-induced receptor dimerization.

The background history of the crystal structure analysis of the EGF-EGFR complex in the present invention and matters deduced from detailed studies on the analytical results will be described as follows.

2-1 Structure Determination

The patent or application file contains at least one drawing executed in color. Copies of this patent or patent application publication with drawings will be provided by the Office upon request and payment of the necessary fee.

In the present invention, the extracellular domain of human EGFR was expressed in Chinese hamster ovary Lec8 cells producing a protein with N-linked oligosaccharides lacking the terminal sialic acid and galactose residues, and then purified. The thus obtained proteins were deglycosylated by digestion with endoglycosidases D and H and crystallized with human EGF (hEGF). We also expressed, purified, deglycosylated, and crystallized selenomethionine-substituted recombinant proteins from Lec8 cells as the native crystals. All diffraction data were collected in Spring-8. Therefore, the native crystal structure was determined to 3.5 Å by the MAD method and the molecular replacement analysis method (FIGS. 1a and 1b). The resulting electron density map could be sufficiently used for building a model for the complex (FIG. 1c). After the final stages of refinement, $R_{cryst}$ and $R_{free}$ resulted in 28% and 34% respectively, due to the relatively large solvent content of 75% and the relatively large missing regions corresponding to 18% of the amino acid residues composing the complex. Data collection and refinement statistics are shown in Table 3.

structure is stabilized by receptor-receptor interaction. First, EGF binds to EGFR, so that domains I and III of EGFR curve to EGF side so as to hold the EGF protein within the pocket. The curved portions of domains are bound back-to-back via domain II (also referred to as S1 domain) so as to form a dimer. At this time, the EGFR proteins are in a form resembling sword guards facing each other. Hence, the two EGF proteins are not directly in contact each other and are 79 Å apart.

Domains I and III consist of a right-handed repetitive β-sheet structure, whose backbones are individually analogous to L1 and L2 domains of the unliganded IGF-1R (insulin-like growth factor-1 receptor), with the root-mean-squared difference (RMSD) values for the corresponding Cα atoms in each domain of 2.1 Å for domain I and 4.0 Å for domain III, respectively. A comparison with the structure of unliganded IGF-1R has revealed a significant difference between domains II and III orientation of the complex of the present invention and the S1-L2 orientation. The dimeric structure of the EGFR-EGF complex has been shown to have features such that loops extrude from each domain II (S1 domain) of the receptor due to the binding of EGFR to EGF, and with these extruding loops the complexes are bound to each other. This binding type has not been shown in any conventional modeling structure of the extracellular domains

TABLE 3

Diffraction data and crystallographic refinement statistics

| Crystal | Native | Se-Met | | | |
|---|---|---|---|---|---|
| | | (Peak) | (Edge) | (Remote 1) | (Remote 2) |
| Wavelength (Å) | 1.000 | 0.9795 | 0.9798 | 0.9733 | 0.9839 |
| Resolution (Å) | 50-3.5 | 50-4.0 | 50-4.0 | 50-4.0 | 50-4.0 |
| Unique reflections | 39517 | 26902 | 26968 | 26796 | 26941 |
| Total reflections | 293584 | 214772 | 210007 | 199751 | 198119 |
| $R_{sym}$ (%)[a] | 7.5(27.0)* | 8.0(20.5)* | 7.2(25.7)* | 6.4(22.0)* | 5.7(26.1)* |
| Completeness (%) | 99.0(98.6)* | 98.6(96.8)* | 98.5(97.0)* | 98.3(95.3)* | 98.4(95.9)* |
| I/σ (I) | 25.6(5.1)* | 24.9(4.7)* | 21.7(3.2)* | 22.2(3.6)* | 20.5(2.9)* |

| MAD phasing | |
|---|---|
| Se atom found | 13 (total 20) |
| Figure of merit | 0.39 |

| Crystallographic refinement statistics | | | |
|---|---|---|---|
| Resolution | 10.0-3.5 | Rmsd from ideality | |
| Number of reflections | 37704 | Bond length (Å) | 0.009 |
| Number of atoms | 8767 | Bond angles (°) | 1.6 |
| $R_{work}/R_{free}$ (%)[b] | 28.1/34.3 | | |

*Numbers within parentheses correspond to the values in the highest resolution shell.
[a]$R_{sym} = \Sigma_h \Sigma_i |I_{hi} - <I_h>|/\Sigma_h \Sigma_i |I_{hi}|$ (where $<I_h>$ indicates the $h^{th}$ average intensity of unique reflection, and $I_{hi}$ indicates $i^{th}$ intensity observed.)
[b]$R_{work} = \Sigma ||F_o| - |F_c||/\Sigma |F_o|$, $R_{free} = \Sigma ||F_o| - |F_c||/\Sigma |F_o|$ (5% of total reflection was used)

2-2 Overall Structure

In the present invention, the crystal structure determination of a dimeric EGFR-EGF complex at 3.5 Å has revealed atomic structures of EGF-EGFR binding sites and EGFR dimerization sites. The dimer in the asymmetric unit of the crystal contains two EGF-bound EGFRs. The ligand-receptor interface consists of one site in domain I and two sites in domain III of EGFR. A cleft, at which EGF interacts extensively with domains I and III of the receptor, is formed by domains I, II, and III of EGFR. There are absolutely no interactions between EGF and the other receptor. The dimer of EGFR (Protein Sci. 2000, 9, 310-324). This binding type is a finding that has been discovered for the first time in the present invention, and shows new structural features. The loop region required for this dimerization has been shown to be specific to the EGFR family based on the amino acid sequence alignment of the proteins, not present in the insulin receptor family. Domain II shows the folding manner analogous to that of S1 of IGF-1R, except for the difference between the loop between Cys240 and Cys267 located outside the curve (on the side opposite from the EGF-bound region) of the EGFR-EGF complex and the loop between Cys252 and Cys273 located inside the IGF-1R molecule, with the RMSD for the corresponding Cα atoms of 3.2 Å. The two equivalent C-terminal residues (Val481) of domain III are 77 Å apart, which would not bring the cytoplasmic domains closer together without domain IV in the dimer.

In addition, in this specification, numerals described together with amino acids (three letter code) indicate amino acid numbers corresponding to those of the amino acid sequence of EGFR (SEQ ID NO: 1) when EGFR is denoted. When EGF is denoted, numerals indicate amino acid numbers corresponding to those of the amino acid sequence of EGF (SEQ ID NO: 2). When IGF-1R is denoted, numerals indicate amino acid numbers corresponding to those of the amino acid sequence of IGF-1R (SEQ ID NO: 3).

2-3 Ligand-Receptor Interaction

EGF interacts with 3 sites on EGFR consisting of site 1 in domain I, and site 2 and site 3 in domain III (FIG. 2a). These interfaces between the ligand and the receptor are extensive such that the interface area of domain I reaches approximately 720 Å$^2$ and the same of domain III reaches 730 Å$^2$, and the interfaces are dominated by hydrophobic interactions. Leu14, Tyr45, Leu69, and Leu98 side chains in site 1 and Met21, Ile23, and Leu26 side chains in the B-loop of EGF create hydrophobic environments (FIG. 2b). Val350 and Phe357 side chains in site 2 and Tyr13 and Leu15 side chains in EGF create a hydrophobic environment (FIG. 3a). Phe412 and Ile438 side chains in site 3 and the Leu47 side chain in EGF create a hydrophobic environment (FIG. 3b). Amino acid residues having the above properties are conserved among the EGF family members, suggesting that the above interfaces between the receptor and the ligand may be present at conserved interaction sites of other EGF family members.

Site-directed mutagenesis conducted by substituting the amino acid sequence of the ligand have suggested the importance of the above hydrophobic residues, Tyr13, Met21, Ile23 and Leu26 in receptor binding (Tadaki, D. K. & Niyogi, S. K. J. Biol. Chem. 268, 10114-10119 (1993); Campion, S. R. et al., Biochemistry 29, 9988-9993 (1990); Koide, H. et al., Biochim. Biophys. Acta 1120, 257-261 (1992)).

An experiment of substituting Ile23 of EGF by mutagenesis with Ala, Val, Leu, Phe, Trp, or the like has shown that Ile23 in EGF is required for the tight binding with the receptor, and the binding site is known to be appropriate for the size of the isoleusine residue. This is in good agreement with the fact that the Ile23 binding region in EGF, which is formed by Leu14, Tyr45, and Leu69 side chains in EGFR domain I, is almost complementary to the isoleucine side chain in the crystal structure.

Similarly, the result of an experiment conducted by substituting Tyr13 of EGF by mutagenesis with Phe, Leu, Val, Ala or the like and then binding the EGF to the receptor suggests that Tyr13 is of an optimum size. This is in firm agreement with the fact that the Tyr13 binding region, which is formed by Phe357 side chain and His10, Tyr29, and Arg41 side chains in domain III, is complementary to the tyrosine side chain in the crystal structure. The Glu90 side chain in site 1 forms a salt bridge with the Lys28 side chain derived from the ligand, and the Asp355 side chain in site 2 forms a salt bridge with the Arg41 side chain derived from the ligand in the crystal structure. Mutagenesis and biochemical studies have shown that the guanidium group of Arg41 in EGF is a critical determinant of binding with the receptor (Engler, D. A. et al., J. Biol. Chem. 267, 2274-2281 (1992)). This is in firm agreement with the analytical results of the crystal structure where the above side chains are placed close to the Tyr13 side chain derived from the ligand and the Phe357 side chain derived from the receptor, creating a hydrophobic environment. As a result of a binding assay that the EGF having mutation of Lys28 with Leu by mutagenesis, the substitution with the Leu had almost no effect on receptor binding. This is apparently inconsistent with the crystal structure, indicating that ionic interactions at position 28 are not always required (Campion, S. R. et al., Biochemistry 29, 9988-9993 (1990)).

Several hydrogen bonds further fortify the ligand-receptor interface. The Gln16 side chain in site 1 forms a hydrogen bond with the Asn32 side chain derived from the ligand. The result of substitution of Asn32 in EGF with His, Phe, Val, Asp, or the like by mutagenesis suggests that Asn32 in EGF is required for tight binding with the receptor (Koide, H. et al., FEBS Lett. 302, 39-42 (1992)). The Gln384 side chain in site 3 forms hydrogen bonds with atoms of Gln43 and Arg45 main chains in the ligand.

A study on chimeric EGF-heregulin peptides (Barbacci, E. G. et al., J. Biol. Chem. 270, 9585-9589 (1995)) has shown that the N-terminal 5 residues of heregulin are of specific importance for binding to the heregulin receptor (ErbB-4). However, no interactions in an N-terminal region are observed in the crystal structure, suggesting that the differences in binding sites of the ligands result in different binding sites of the receptors and may confer ligand-receptor specificities among the EGFR family members. No specific interactions with amino acids, whose properties were not conserved among the EGF family members, are observed in the crystal structure except for Asn32 in EGF. The corresponding position in TGF-α sharing a ligand-binding site with EGF, is substituted with Val, suggesting that Asn32 would not confer ligand specificity on EGFR. It has been shown that the N-terminus of EGF can be linked to the residues Tyr101 and Lys336. Though no interactions between the N-terminal region (disordered, so that the structure cannot be seen) of EGF and EGFR are observed in the crystal structure, the estimated distance between the Cα of Glu5 that is the N-terminus of the EGF structure and Tyr101 and the distance between the same and Lys336 are 16 Å and 39 Å, respectively, in the crystal structure.

This indicates that the N-terminus of EGF can be linked to the Tyr101, but cannot be linked to Lys336. It is also possibly considered that stable dimeric EGF-bound EGFR would be formed via several intermediate states, in which EGF may bind to EGFR at some different sites of a receptor that cannot be elucidated based on the crystal structure. The residues 10 to 17, 85 to 94, and 101 to 107 in domain I and the residues 316 to 325, 353 to 362, and 404 to 413 in domain III seem to loop out the barrels in the form of a right-handed repetitive β-sheet structure. Among the above loops, the loops 10 to 17 and 353 to 362 participate in EGF binding. This is consistent with the loops 353 to 362 encompassing most of the epitope (residues 351 to 364) to the ligand-competitive-monoclonal antibody, LA22 (Wu, D. G. et al., J. Biol. Chem. 264, 17469-17475 (1989)).

In the above explanation, amino acid residues shown to participate in EGF-EGFR interaction based on the results of structure analysis made on the EGF-EGFR complex are examples of amino acids creating interaction that is important in the EGF-EGFR binding sites.

2-4 Receptor-Receptor Interaction

The interaction between the two EGFR molecules in the dimer is almost limited to domain II (FIGS. 4a, 4b, and 4c). The total surface area buried of this interface is approximately 1270 Å$^2$. The loop between Cys240 and Cys267, in particular, participates in the receptor dimerization. Across the 2-fold rotational axis of the dimer, the Tyr246, Pro248, and Tyr251 side chains create hydrophobic environments with the Phe230, Phe263, Ala265, Tyr275, and Arg285 side chains derived from the other receptor. This is achieved by hydrogen bonds between the Ty275 and Arg285 side chains.

The Gln252 side chain forms a hydrogen bond with the backbone nitrogen and carbonyl oxygen of Ala286. Hydrogen bonds between the Tyr246 side chain and the backbone oxygen of Cys283 of the other receptor fortify the interface. The properties of most of the above amino acid residues are conserved among the EGFR family members, suggesting that these interfaces between the loops of each receptor may be present at conserved dimerization sites of other EGFR family members. In addition to the above domain II-domain II interactions, a sole interaction between an amino acid residue in domain II and an amino acid residue in domain I of the other receptor is also observed in the crystal structure disclosed in this specification. In detail, the Thr249 side chain extruding from the dimerization loop forms a hydrogen bond with the Asn86 side chain derived from domain I of the other receptor.

The amino acid residues that are shown in the above explanation to participate in dimerization based on the results of the structure analysis made on the EGF-EGFR complex are examples of amino acids creating important interactions at the EGFR dimerization sites.

2-5 Mechanisms of Ligand-Dependent Receptor Dimerization

It is necessary to first understand the receptor activation mechanism responsible for signal transduction. EGFR has been one of the representative targets of much research on signal transduction across the membrane. During the past quarter century, biochemical and physical biology data concerning the activation mechanism of EGFR has been gradually accumulated. Although binding EGF to the EGFR extracellular domain has been thought to induce stable dimer formation, dimerization patterns (whether dimerization is mediated by EGF or takes place on the receptor side) have remained unknown (Lemmon, M. A. et al., Embo J. 16, 281-294 (1997)). We have shown for the first time the structure of this stable dimeric EGFR-EGF complex.

Based on comparison of the crystal structure of the EGF-EGFR complex with that of unliganded IGF-1R, we have deduced the mechanisms of EGF-induced receptor dimerization. The crystal structure, in which receptor dimerization is not mediated by interactions involving EGF but is mediated by direct interaction between domain II and domain II of the 2 EGFR proteins, indicating that EGF binding to the receptor results in conformational changes that expose receptor-receptor interaction sites. One of the loop regions specific to the EGFR family lies between Cys240 and Cys267 in EGFR. The significant roles of these loops functioning as dimerization sites have been elucidated for the first time from the crystal structure of the present invention.

From the comparison with the unliganded IGF-1R, we have deduced that a ligand binding to the extracellular domain of EGFR would induce a change of inter-domain orientation at a putative hinge region (Lys303 to Lys311) and bring domain III into the proximity of domain II (FIG. 5a). We have assumed that the Gln293 side chain might make a salt bridge with the Arg285 side chain in domain II of an unbound EGFR monomer. This assumption is reasonably derived from a comparison with the structure of unbound IGF-1R, in which the R283 side chain at corresponding position makes a salt bridge with the Glu276 side chain in S1 domain (FIG. 5b). The ligand-dependent conformational change would place the Arg405 side chain in domain III within reach of the Glu293 side chain, followed by making a salt bridge between these side chains. The Arg285 side chain located away from its partner for interaction would interact with the Tyr275 side chain. Consequently, a hydrophobic environment is created together with the Phe263, Tyr275, and Arg285 side chains, where the Tyr251 side chain extruding from domain II of the other receptor makes hydrophobic contact as shown in the crystal structure (FIG. 5c). We speculate that the ligand-dependent conformational change of the receptor may control the above interaction and other unidentified structural changes.

We now discuss other potential structural changes. It would be more effective for ligand-dependent receptor activation to assume that the dimerization loop does not extrude from domain II and is tucked into itself before receptor activation. For this purpose, we propose the following model by tentatively assuming that the Arg273 side chain might make a salt bridge with the Asp254 side chain in domain II of an unbound EGFR monomer (FIG. 5c).

An EGF-dependent conformational change of the receptor would place the Gly458 main chain in domain III within reach of Arg273, followed by making a hydrogen bond between the oxygen of Gly458 main chain and the side chain derived from Arg273. The Asp254 side chain would be liberated from every interactions, so that the dimerization loop encompassing the Asp254 extrudes from domain II, thereby permitting interactions to take place between the dimerization loops of each receptor.

Dimerization of the extracellular domains of EGFRs brings the cytoplasmic tyrosine kinase domains of the two receptors into close proximity, resulting in activation of the intrinsic tyrosine kinase receptor in the intracellular domain similarly to the case of an erythropoietin receptor (Remy, I. et al., Science 283, 990-993 (1999)).

2-6 Conclusion

We have revealed for the first time the structure of a dimeric EGFR-EGF complex on the basis of X-ray diffraction data at 3.5 Å and 3.3 Å. The crystal structure of the present invention displays the novel structural feature that only the two loops extruding from each domain II of the receptor in the dimer are major dimerization sites. The crystal structure of the present invention provides for the first time not only information by which the ligand-dependent EGFR activation is explained on the atomic level, but also important information for developing an EGFR family antagonist or an activation inhibitor as, for example, a novel antitumor agent.

Comparison and analysis of the coordinates of EGF crystal structures and EGFR modeling structures that have been obtained by conventional techniques with those of the EGF-EGFR complex crystal structure obtained in the present invention make it clear that the flow of the amino acid backbones and the side chain conformations of the former structures do not have accuracy sufficient for use in industrial applications such as drug design.

When EGF crystal structure 1JL9 (J. Biol. Chem. 276 pp. 34913 (2001)) elucidated in 2001 and the structure of an EGFR-EGF complex were compared, specifically, in the case of superimposition (superimposition by the least squares method) of the Cys6-Leu47 main chain, the RMSD (root mean square deviation) value between the two was 1.5 Å in the case of 1JL9A chain, and the RMSD value between the two was 2.9 Å in the case of 1JL9B chain. When superimposition was conducted including side chains important for exerting EGF activity, the gap between the structures increased, such that an RMSD value between the two was 3.5 Å in the case of the A chain, and the RMSD value between the two was 4.2 Å in the case of B chain. It was revealed that the EGF structure of the conventional technology merely reflects the structure in a state of being unbound to EGFR, and is not sufficient information to provide the active conformation observed in the complex with EGFR exerting pharmacological activity. The only reason why the active conformation of EGF in the EGF-EGFR co-crystal structure is so different from the conformation of EGF in a free state presented by conventional technology is that the binding of EGF to EGFR causes the conformation or the orientation of the side chains to alter in terms of the exertion of EGF activity. This altered structure itself is active conformation and the provision of this is useful for creating or developing drugs. Hence, it clearly involves an inventive step whereby the active conformation of the EGF/EGFR has been elucidated by the present invention.

According to the three-dimensional structure of an EGFR protein of conventional technology, no structure of the EGF-EGFR complex has been known, and the modeling structure of an EGFR monomer has been merely predicted. Conventionally, a ligand-binding site of an insulin-like growth factor-1 receptor has been crystallized in an unliganded state, and the structure has been specified. However, since the active conformation when the ligand is bound cannot be predicted with this structure, it has been difficult to provide information sufficient to carry out scientific analysis and molecular design. In particular, the active conformation of EGFR alters dynamically, so that it is impossible to infer the active conformation using an unliganded structure. In the homology modeling method, the structure of a template specifies the conformation of a target protein (EGFR monomer) model structure upon modeling. By conducting EGFR modeling using an unliganded IGF-1R structure as a template, an EGFR model with conformation similar to that of the unliganded IGF-1R can be obtained. Comparison of the crystal structure of the insulin-like growth factor-1 receptor monomer used as a template for the EGFR modeling structure with the EGFR structure of the EGF-EGFR complex revealed by the present invention makes it possible to understand that even in visual analysis, modeling of the active conformation using the unliganded structure is extremely difficult (see FIG. 8).

The structure coordinates provided from the co-crystal structure of the complex of the present invention is useful in pharmacophore extraction of a substance regulating EGFR activity (specifically, agonists and antagonists), computer screening using all or some of the structure coordinates of the complex, molecular design (e.g., increased activity and provision of selectivity) of EGFR agonists or EGFR antagonists, design and screening for industrially useful EGF variants or EGFR variants, preparation of EGF neutralization antibodies and EGF agonist antibodies, the molecular replacement method utilizing the EGF-EGFR crystal structure, modeling of a protein thought to have folds similar to those of EGFR such as an insulin receptor and the use of the modeling structure (e.g., computer screening, molecular design, antibody design, designing of altered proteins, and the molecular replacement method), and the like. The present invention provides the structure coordinates of the EGF-EGFR complex that can be used for these purposes.

More specifically, the present invention provides the following structure coordinates (a) to (zc):

(a) all or some of structure coordinates shown in Table 1;

(b) structure coordinates of an EGF-EGFR complex, which are characterized in that the root mean square deviation of α carbon atomic coordinates is 2.0 Å or less when the structure coordinates are superimposed on those of the EGF-EGFR complex shown in Table 1.

(c) structure coordinates of EGFR, which are specified by atom serial numbers 1 to 3957 from the structure coordinates shown in Table 1;

(d) structure coordinates of EGFR, which are characterized in that the root mean square deviation of α carbon atomic coordinates is 2.0 Å or less when the structure coordinates are superimposed on those of EGFR specified by atom serial numbers 1 to 3957 from the structure coordinates shown in Table 1;

(e) some of the structure coordinates of EGFR, comprising at least any one of the following structure coordinates (e-1) to (e-4);

(e-1) structure coordinates of a portion corresponding to domain I of EGFR which are specified by atom serial numbers 1 to 3957 from the structure coordinates shown in Table 1;

(e-2) structure coordinates of a portion corresponding to domain II of EGFR which are specified by atom serial numbers 1 to 3957 from the structure coordinates shown in Table 1;

(e-3) structure coordinates of a portion corresponding to domain III of EGFR which are specified by atom serial numbers 1 to 3957 from the structure coordinates shown in Table 1;

(e-4) structure coordinates of a portion corresponding to domain I, II, or III of EGFR, which are characterized in that the root mean square deviation of α carbon atomic coordinates is 2.0 Å or less when the structure coordinates are superimposed on those of the portion corresponding to domain I, II, or III of EGFR specified by any one of (e-1) to (e-3);

(f) structure coordinates of EGFR, which are specified by atom serial numbers 3958 to 7887 from the structure coordinates shown in Table 1;

(g) structure coordinates of EGFR, which are characterized in that the root mean square deviation of α carbon atomic coordinates is 2.0 Å or less when the structure coordinates are superimposed on those of EGFR specified by atom serial numbers 3958 to 7887 from the structure coordinates shown in Table 1;

(h) some of the structure coordinates of EGFR, comprising at least any one of the following structure coordinates (h-1) to (h-4);

(h-1) structure coordinates of a portion corresponding to domain I of EGFR which are specified by atom serial numbers 3958 to 7887 from the structure coordinates shown in Table 1;

(h-2) structure coordinates of a portion corresponding to domain II of EGFR which are specified by atom serial numbers 3958 to 7887 from the structure coordinates shown in Table 1;

(h-3) structure coordinates of a portion corresponding to domain III of EGFR which are specified by atom serial numbers 3958 to 7887 from the structure coordinates shown in Table 1;

(h-4) structure coordinates of a portion corresponding to domain I, II, or III of EGFR, which are characterized in that the root mean square deviation of α carbon atomic coordinates is 2.0 Å or less when the structure coordinates are superimposed on those of the portion corresponding to domain I, II, or III of EGFR specified by any one of (h-1) to (h-3);

(i) structure coordinates of EGF, which are specified by atom serial numbers 7888 to 8250 from the structure coordinates shown in Table 1;

(j) structure coordinates of EGF, which are characterized in that the root mean square deviation of α carbon atomic coordinates is 2.0 Å or less when the structure coordinates are superimposed on those of EGF specified by atom serial numbers 7888 to 8250 from the structure coordinates shown in Table 1;

(k) structure coordinates of EGF, which are specified by atom serial numbers 8251 to 8613 from the structure coordinates shown in Table 1;

(l) structure coordinates of EGF, which are characterized in that the root mean square deviation of α carbon atomic coordinates is 2.0 Å or less when the structure coordinates are superimposed on those of EGF specified by atom serial numbers 8251 to 8613 from the structure coordinates shown in Table 1;

(m) all or some of structure coordinates shown in Table 2;

(n) structure coordinates of an EGF-EGFR complex, which are characterized in that the root mean square deviation of α carbon atomic coordinates is 2.0 Å or less when the structure coordinates are superimposed on those of the EGF-EGFR complex specified by the structure coordinates shown in Table 2;

(o) structure coordinates of EGFR, which are specified by atom serial numbers 1 to 3957 from the structure coordinates shown in Table 2;

(p) structure coordinates of EGFR, which are characterized in that the root mean square deviation of α carbon atomic coordinates is 2.0 Å or less when the structure coordinates are superimposed on those of EGFR specified by atom serial numbers 1 to 3957 from the structure coordinates shown in Table 2;

(q) some of the structure coordinates of EGFR, comprising at least any one of the following structure coordinates (q-1) to (q-4);

(q-1) structure coordinates of a portion corresponding to domain I of EGFR which are specified by atom serial numbers 1 to 3957 from the structure coordinates shown in Table 2;

(q-2) structure coordinates of a portion corresponding to domain II of EGFR which are specified by atom serial numbers 1 to 3957 from the structure coordinates shown in Table 2;

(q-3) structure coordinates of a portion corresponding to domain III of EGFR which are specified by atom serial numbers 1 to 3957 from the structure coordinates shown in Table 2;

(q-4) structure coordinates of a portion corresponding to domain I, II, or III of EGFR, which are characterized in that the root mean square deviation of α carbon atomic coordinates is 2.0 Å or less when the structure coordinates are superimposed on those of the portion corresponding to domain I, II, or III of EGFR specified by any one of (q-1) to (q-3);

(r) structure coordinates of EGFR, which are specified by atom serial numbers 3958 to 7905 from the structure coordinates shown in Table 2;

(s) structure coordinates of EGFR, which are characterized in that the root mean square deviation of α carbon atomic coordinates is 2.0 Å or less when the structure coordinates are superimposed on those of EGFR specified by atom serial numbers 3958 to 7905 from the structure coordinates shown in Table 2;

(t) some of the structure coordinates of EGFR, comprising at least any one of the following structure coordinates (t-1) to (t-4);

(t-1) structure coordinates of a portion corresponding to domain I of EGFR which are specified by atom serial numbers 3958 to 7905 from the structure coordinates shown in Table 2;

(t-2) structure coordinates of a portion corresponding to domain II of EGFR which are specified by atom serial numbers 3958 to 7905 from the structure coordinates shown in Table 2;

(t-3) structure coordinates of a portion corresponding to domain III of EGFR which are specified by atom serial numbers 3958 to 7905 from the structure coordinates shown in Table 2;

(t-4) structure coordinates of a portion corresponding to domain I, II, or III of EGFR, which are characterized in that the root mean square deviation of α carbon atomic coordinates is 2.0 Å or less when the structure coordinates are superimposed on those of the portion corresponding to domain I, II, or III of EGFR specified by any one of (t-1) to (t-3);

(u) structure coordinates of EGF, which are specified by atom serial numbers 7906 to 8291 from the structure coordinates shown in Table 2;

(v) structure coordinates of EGF, which are characterized in that the root mean square deviation of α carbon atomic coordinates is 2.0 Å or less when the structure coordinates are superimposed on those of EGF specified by atom serial numbers 7906 to 8291 from the structure coordinates shown in Table 2;

(w) structure coordinates of EGF, which are specified by atom serial numbers 8292 to 8677 from the structure coordinates shown in Table 2;

(x) structure coordinates of EGF, which are characterized in that the root mean square deviation of α carbon atomic coordinates is 2.0 Å or less when the structure coordinates are superimposed on those of EGF specified by atom serial numbers 8292 to 8677 from the structure coordinates shown in Table 2;

(ya) structure coordinates of a first EGF-EGFR binding site selected from any one of the following (ya-1) to (ya-8);

(ya-1) structure coordinates of an EGF-EGFR binding site, comprising atomic coordinates of amino acid residues corresponding to at least Leu26 and Lys28 of EGF and Leu69 and Leu98 of EGFR;

(ya-2) structure coordinates of an EGF-EGFR binding site, comprising atomic coordinates of amino acid residues corresponding to at least Leu26 and Lys28 of EGF and Leu69 and Leu98 of EGFR, and atomic coordinates of one or more amino acid residues selected from amino acid residues corresponding to Met21, Ile23, Ala25, Cys31, Asn32, and Cys33 of EGF, and Leu14, Gln16, Gly18, Glu35, Tyr45, Ala68, Glu90, and Tyr101 of EGFR;

(ya-3) structure coordinates of an EGF-EGFR binding site, consisting of the atomic coordinates of the amino acid residues corresponding to at least Leu26 and Lys28 of EGF and Leu69 and Leu98 of EGFR, and atomic coordinates of one or more amino acid residues selected from amino acid residues corresponding to Met21, Ile23, Ala25, Cys31, Asn32, and Cys33 of EGF and Leu14, Gln16, Gly18, Glu35, Tyr45, Ala68, Glu90, and Tyr101 of EGFR;

(ya-4) structure coordinates of an EGF-EGFR binding site, consisting of atomic coordinates of amino acid residues corresponding to at least Leu26 and Lys28 of EGF and Leu69 and Leu98 of EGFR, and atomic coordinates of one or more amino acid residues selected from amino acid residues corresponding to Met21, Ile23, Ala25, Cys31, Asn32 and Cys33 of EGF, and Leu14, Gln16, Gly18, Glu35, Tyr45, Ala68, Glu90 and Tyr101 of EGFR and amino acid residues adjacent thereto;

(ya-5) structure coordinates of an EGF-EGFR binding site, comprising atomic coordinates of amino acid residues corresponding to at least Ile23, Leu26, and Lys28 of EGF and Leu14, Tyr45, Leu69, Glu90, and Leu98 of EGFR;

(ya-6) structure coordinates of an EGF-EGFR binding site, comprising atomic coordinates of amino acid residues corresponding to at least Ile23, Leu26, and Lys28 of EGF and Leu14, Tyr45, Leu69, Glu90, and Leu98 of EGFR, and atomic coordinates of one or more amino acid residues selected from amino acid residues corresponding to Met21, Ala25, Cys31, Asn32, and Cys33 of EGF and Gln16, Gly18, Glu35, Ala68, and Tyr101 of EGFR;

(ya-7) structure coordinates an EGF-EGFR binding site, consisting of atomic coordinates of the amino acid residues corresponding to at least Ile23, Leu26, and Lys28 of EGF and Leu14, Tyr45, Leu69, Glu90, and Leu98 of EGFR, and atomic coordinates of one or more amino acid residues selected from amino acid residues corresponding to Met21, Ala25, Cys31, Asn32, and Cys33 of EGF and Gln16, Gly18, Glu35, Ala68, and Tyr101 of EGFR;

(ya-8) structure coordinates an EGF-EGFR binding site, consisting of atomic coordinates of amino acid residues corresponding to at least Ile23, Leu26, and Lys28 of EGF and Leu14, Tyr45, Leu69, Glu90, and Leu98 of EGFR, and atomic coordinates of one or more amino acid residues selected from amino acid residues corresponding to Met21, Ala25, Cys31, Asn32, and Cys33 of EGF and Gln16, Gly18, Glu35, Ala68, and Tyr101 of EGFR and amino acid residues adjacent thereto;

(yb) structure coordinates of a second EGF-EGFR binding site selected from any one of the following (yb-1) to (yb-8);

(yb-1) structure coordinates of an EGF-EGFR binding site, comprising atomic coordinates of amino acid residues corresponding to at least Leu15 and Arg41 of EGF and Val350 and Asp355 of EGFR;

(yb-2) structure coordinates of an EGF-EGFR binding site, comprising atomic coordinates of amino acid residues corresponding to at least Leu15 and Arg41 of EGF and Val350 and Asp355 of EGFR, and atomic coordinates of one or more amino acid residues selected from amino acid residues corresponding to His10, Asp11, Tyr13, His16, Cys31, Asn32, Cys33, Ile38, Gly39, and Glu40 of EGF, and Thr10, Asn12, Lys13, Gln16, Leu17, Gly18, Leu27, Leu325, Ser356, Phe357, Gln384, and His409 of EGFR;

(yb-3) structure coordinates of an EGF-EGFR binding site, consisting of atomic coordinates of amino acid residues corresponding to at least Leu15 and Arg41 of EGF and Val350 and Asp355 of EGFR, and atomic coordinates of one or more amino acid residues selected from amino acid residues corresponding to His10, Asp11, Tyr13, His16, Cys31, Asn32, Cys33, Ile38, Gly39, and Glu40 of EGF and Thr10, Asn12, Lys13, Gln16, Leu17, Gly18, Leu27, Leu325, Ser356, Phe357, Gln384, and His409 of EGFR;

(yb-4) structure coordinates of an EGF-EGFR binding site, consisting of atomic coordinates of amino acid residues corresponding to at least Leu15 and Arg41 of EGF and Val350 and Asp355 of EGFR, and atomic coordinates of one or more amino acid residues selected from amino acid residues corresponding to His10, Asp11, Tyr13, His16, Cys31, Asn32, Cys33, Ile38, Gly39, and Glu40 of EGF, and Thr10, Asn12, Lys13, Gln16, Leu17, Gly18, Leu27, Leu325, Ser356, Phe357, Gln384, and His409 of EGFR and amino acid residues adjacent thereto;

(yb-5) structure coordinates of an EGF-EGFR binding site, comprising atomic coordinates of amino acid residues corresponding to at least Tyr13, Leu15, and Arg41 of EGF and Val350, Asp355, and Phe357 of EGFR;

(yb-6) structure coordinates of an EGF-EGFR binding site, comprising atomic coordinates of amino acid residues corresponding to at least Tyr13, Leu15, and Arg41 of EGF and Val350, Asp355, and Phe357 of EGFR, and atomic coordinates of one or more amino acid residues selected from amino acid residues corresponding to His10, Asp11, His16, Cys31, Asn32, Cys33, Ile38, Gly39, and Glu40 of EGF and Thr10, Asn12, Lys13, Gln16, Leu17, Gly18, Leu27, Leu325, Ser356, Gln384, and His409 of EGFR;

(yb-7) structure coordinates of an EGF-EGFR binding site, consisting of atomic coordinates of amino acid residues corresponding to at least Tyr13, Leu15, and Arg41 of EGF and Val350, Asp355, and Phe357 of EGFR, and atomic coordinates of one or more amino acid residues selected from amino acid residues corresponding to His10, Asp11, His16, Cys31, Asn32, Cys33, Ile38, Gly39, and Glu40 of EGF and Thr10, Asn12, Lys13, Gln16, Leu17, Gly18, Leu27, Leu325, Ser356, Gln384, and His409 of EGFR;

(yb-8) structure coordinates of an EGF-EGFR binding site, consisting of atomic coordinates of amino acid residues corresponding to at least Tyr13, Leu15, and Arg41 of EGF and Val350, Asp355, and Phe357 of EGFR, and atomic coordinates of one or more amino acid residues selected from amino acid residues corresponding to His10, Asp11, His16, Cys31, Asn32, Cys33, Ile38, Gly39, and Glu40 of EGF and Thr10, Asn12, Lys13, Gln16, Leu17, Gly18, Leu27, Leu325, Ser356, Gln384, and His409 of EGFR and amino acid residues adjacent thereto;

(yc) structure coordinates of a third EGF-EGFR binding site selected from any one of the following (yc-1) to (yc-8);

(yc-1) structure coordinates of an EGF-EGFR binding site, comprising the atomic coordinates of amino acid residues corresponding to at least Arg45 and Leu47 of EGF and Leu382, Gln384, Phe412, and Ile438 of EGFR;

(yc-2) structure coordinates of an EGF-EGFR binding site, comprising atomic coordinates of amino acid residues corresponding to at least Arg45 and Leu47 of EGF and Leu382, Gln384, Phe412, and Ile438 of EGFR, and atomic coordinates of one or more amino acid residues selected from amino acid residues corresponding to Gln43, Tyr44, Asp46, and Lys48 of EGF, and Arg29, Leu325, His346, Gln408, Gln411, Ala415, and Val417 of EGFR;

(yc-3) structure coordinates of an EGF-EGFR binding site, consisting of atomic coordinates of amino acid residues corresponding to at least Arg45 and Leu47 of EGF and Leu382, Gln384, Phe412, and Ile438 of EGFR, and atomic coordinates of one or more amino acid residues selected from amino acid residues corresponding to Gln43, Tyr44, Asp46, and Lys48 of EGF and Arg29, Leu325, His346, Gln408, Gln411, Ala415, and Val417 of EGFR;

(yc-4) structure coordinates of an EGF-EGFR binding site, consisting of atomic coordinates of amino acid residues corresponding to at least Arg45 and Leu47 of EGF and Leu382, Gln384, Phe412, and Ile438 of EGFR, and atomic coordinates of one or more amino acid residues selected from amino acid residues corresponding to Gln43, Tyr44, Asp46, and Lys48 of EGF and Arg29, Leu325, His346, Gln408, Gln411, Ala415, and Val417 of EGFR and amino acid residues adjacent thereto;

(yc-5) structure coordinates of an EGF-EGFR binding site, comprising atomic coordinates of amino acid residues corresponding to at least Gln43, Arg45, and Leu47 of EGF and Leu382, Gln384, Phe412, and Ile438 of EGFR;

(yc-6) structure coordinates of an EGF-EGFR binding site, comprising atomic coordinates of amino acid residues corresponding to at least Gln43, Arg45, and Leu47 of EGF and Leu382, Gln384, Phe412, and Ile438 of EGFR, and atomic coordinates of one or more amino acid residues selected from amino acid residues corresponding to Tyr44, Asp46, and Lys48 of EGF and Arg29, Leu325, His346, Gln408, Gln411, Ala415, and Val417 of EGFR;

(yc-7) structure coordinates of an EGF-EGFR binding site, consisting of atomic coordinates of amino acid residues corresponding to at least Gln43, Arg45, and Leu47 of EGF and Leu382, Gln384, Phe412, and Ile438 of EGFR, and atomic coordinates of one or more amino acid residues selected from amino acid residues corresponding to Tyr44, Asp46, and Lys48 of EGF and Arg29, Leu325, His346, Gln408, Gln411, Ala415, and Val417 of EGFR;

(yc-8) structure coordinates an EGF-EGFR binding site, consisting of atomic coordinates of amino acid residues corresponding to at least Gln43, Arg45, and Leu47 of EGF and Leu382, Gln384, Phe412, and Ile438 of EGFR, and atomic coordinates of one or more amino acid residues selected from amino acid residues corresponding to Tyr44, Asp46, and Lys48 of EGF and Arg29, Leu325, His346, Gln408, Gln411, Ala415, and Val417 of EGFR and amino acid residues adjacent thereto;

(yd) structure coordinates of an EGF-EGFR binding site, comprising the first EGF-EGFR binding site of (ya) and the second EGF-EGFR binding site of (yb);

(ye) structure coordinates of an EGF-EGFR binding site, comprising the second EGF-EGFR binding site of (yb) and the third EGF-EGFR binding site of (yc);

(yf) structure coordinates of an EGF-EGFR binding site, comprising the first EGF-EGFR binding site of (ya) and the third EGF-EGFR binding site of (yc);

(yg) structure coordinates of an EGF-EGFR binding site, comprising the first EGF-EGFR binding site of (ya), the second EGF-EGFR binding site of (yb), and the third EGF-EGFR binding site of (yc);

(yh) structure coordinates of an EGF-EGFR binding site selected from any one of the following (yh-1) to (yh-3);

(yh-1) structure coordinates of an EGF-EGFR binding site, comprising atomic coordinates of amino acid residues corresponding to at least Tyr13, Glu40, Arg41, Asp46, and Leu47 of EGF and Phe357, Lys13, Asp355, Arg29, Leu382, Ala415, and Val417 of EGFR;

(yh-2) structure coordinates, consisting of atomic coordinates of amino acid residues corresponding to His10, Asp11, Tyr13, Leu15, His16, Met21, Ile23, Ala25, Leu26, Lys28, Ala30, Cys31, Asn32, Cys33, Val35, Tyr37, Ile38, Gly39, Glu40, Arg41, Gln43, Tyr44, Arg45, Asp46, Leu47, Lys48 and Trp49 of EGF and Asn12, Lys13, Leu14, Thr15, Gln16, Leu17, Gly18, Asp22, Arg29, Tyr45, Ala68, Leu69, Tyr89, Glu90, Leu98, Ser99, Tyr101, Leu325, His346, Leu348, Pro349, Val350, Asp355, Ser356, Phe357, Thr358, Leu382, Gln384, Gln408, His409, Gln411, Phe412, Ala415, Val417, Ile438 and Lys465 of EGFR;

(yh-3) structure coordinates, consisting of atomic coordinates of amino acid residues corresponding to His10, Asp11, Tyr13, Leu15, His16, Met21, Ile23, Ala25, Leu26, Lys28, Ala30, Cys31, Asn32, Cys33, Val35, Tyr37, Ile38, Gly39, Glu40, Arg41, Gln43, Tyr44, Arg45, Asp46, Leu47, Lys48 and Trp49 of EGF and Asn12, Lys13, Leu14, Thr15, Gln16, Leu17, Gly18, Asp22, Arg29, Tyr45, Ala68, Leu69, Tyr89, Glu90, Leu98, Ser99, Tyr101, Leu325, His346, Leu348, Pro349, Val350, Asp355, Ser356, Phe357, Thr358, Leu382, Gln384, Gln408, His409, Gln411, Phe412, Ala415, Val417, Ile438 and Lys465 of EGFR and amino acid residues adjacent thereto;

(yi) structure coordinates of an EGF-EGFR binding site;

(yj) structure coordinates of an EGFR dimerization site, comprising atomic coordinates of amino acid residues corresponding to at least Thr249, Tyr246, and Gln252 of the $1^{st}$ EGFR protein and Asn86, Cys283, and Ala286 of the $2^{nd}$ EGFR protein, where the two EGFR proteins form a dimer;

(yk) structure coordinates of an EGFR dimerization site, comprising atomic coordinates of amino acid residues corresponding to at least Thr249, Tyr246, and Gln252 of the $1^{st}$ EGFR protein and Asn86, Cys283, and Ala286 of the $2^{nd}$ EGFR protein, where the two EGFR proteins form a dimer, and atomic coordinates of one or more amino acid residues selected from amino acid residues corresponding to Asn86, Gln194, Pro204, Ser205, Lys229, Phe230, Thr239, Pro242, Tyr246, Pro248, Thr249, Tyr251, Gln252, Met253, Ser262, Phe263, Gly264, Ala265, Tyr275, His280, Ser282, Cys283, Val284, Arg285, Ala286, and Lys303 of both EGFR proteins;

(yl) structure coordinates of an EGFR dimerization site, consisting of atomic coordinates of amino acid residues corresponding to Asn86, Gln194, Pro204, Ser205, Lys229, Phe230, Thr239, Pro242, Tyr246, Pro248, Thr249, Tyr251, Gln252, Met253, Ser262, Phe263, Gly264, Ala265, Tyr275, His280, Ser282, Cys283, Val284, Arg285, Ala286, and Lys303 of both EGFR proteins forming a dimer;

(ym) structure coordinates, consisting of atomic coordinates of amino acid residues corresponding to Asn86, Gln194, Pro204, Ser205, Lys229, Phe230, Thr239, Pro242, Tyr246, Pro248, Thr249, Tyr251, Gln252, Met253, Ser262, Phe263, Gly264, Ala265, Tyr275, His280, Ser282, Cys283, Val284, Arg285, Ala286, and Lys303 and amino acid residues adjacent thereto of both EGFR proteins forming a dimer;

(yn) structure coordinates of an EGFR dimerization site, comprising atomic coordinates of amino acid residues corresponding to at least Arg405 and Glu293 of EGFR, and atomic coordinates of one or more amino acid residues selected from amino acid residues corresponding to Arg285, Arg273, Asp254, and Gly458 of EGFR;

(yo) structure coordinates of an EGFR dimerization site, consisting of atomic coordinates of amino acid residues corresponding to at least Arg405 and Glu293 of EGFR, and atomic coordinates of one or more amino acid residues selected from amino acid residues corresponding to Arg285, Arg273, Asp254, and Gly458 of EGFR;

(yp) structure coordinates, consisting of atomic coordinates of amino acid residues corresponding to at least Arg405 and Glu293 of EGFR, and atomic coordinates of one or more amino acid residues selected from the amino acid residues corresponding to Arg285, Arg273, Asp254, and Gly458 of EGFR and amino acid residues adjacent thereto;

(yq) structure coordinates of an EGFR dimerization site;

(za) structure coordinates of a ligand-receptor binding site, which are characterized in that the root mean square deviation of α carbon atomic coordinates is 1.5 Å or less when the structure coordinates are superimposed on those of the amino acid residues composing the EGF-EGFR binding site of any one of (ya) to (yi);

(zb) structure coordinates of a receptor dimerization site, which are characterized in that the root mean square deviation of α carbon atomic coordinates is 1.5 Å or less when the structure coordinates are superimposed on those of the amino acid residues composing the EGFR dimerization site of any one of (yj) to (yq);

(zc) structure coordinates of the EGF-EGFR complex or a structure homologue thereof, comprising the structure coordinates of any one of (a) to (zb).

In the above explanation of the structure coordinates, "α carbon" means a carbon atom at position α of an amino acid, and is also denoted as "Cα." The three-dimensional structure of protein is not firmly fixed, but involves fluctuation to some extent. As long as deviation for the backbone position between entire protein structures, that is, the root mean square deviation of α carbon is 2.0 Å or less, the proteins can be thought to have structures substantially equivalent to each other. Preferably, the root mean square deviation is 1.5 Å or less, and further preferably 1.0 Å or less. Furthermore, in the case of the structures of receptor dimerization sites or ligand-receptor binding sites, as long as the root mean square deviation of the backbone atoms is 1.5 Å or less, the sites can be thought to have functionally equivalent structures. Preferably, the root mean square deviation is 1.0 Å or less, more preferably 0.7 Å or less, and further preferably 0.5 Å or less.

"Some (of structure coordinates)" in (a) or (m) above means structure coordinates consisting of any one or more of the atomic coordinates of the structure coordinates of Table 1 or Table 2. For example, the structure coordinates in Table 1 or Table 2 contain 2 molecules of EGF and 2 molecules of EGFR, and a portion corresponding to one EGF molecule or a portion corresponding to one EGFR molecule among these molecules is an appropriate example of "some (of structure coordinates)." In addition, the coordinates of an EGF-EGFR binding site and coordinates of an EGFR dimerization site are also appropriate examples of "some (of structure coordinates)." Preferably, at a minimum, some (of structure coordinates) refer to structure coordinates containing atomic coordinates of an EGF-EGFR binding site or an EGFR dimerization site. As long as "some (of structure coordinates)" contain structure coordinates of an EGF-EGFR binding site or an EGFR dimerization site, it may also contain any one or more of the atomic coordinates in Table 1 or Table 2. Another appropriate example of "some (of structure coordinates)" is a portion corresponding to any of domain I, II, or III of EGFR. More specific examples of "some (of structure coordinates)" are shown in the structure coordinates (b) to (l), (O) to (x), and (ya) to (yq).

Appropriate examples of the structure coordinates of an EGFR dimerization site are structure coordinates consisting of atomic coordinates of amino acid residues corresponding to Asn86, Gln194, Pro204, Ser205, Lys229, Phe230, Thr239, Pro242, Tyr246, Pro248, Thr249, Tyr251, Gln252, Met253, Ser262, Phe263, Gly264, Ala265, Tyr275, His280, Ser282, Cys283, Val284, Arg285, Ala286, and Lys303 of both EGFR proteins forming a dimer. The structure coordinates of the same may also be structure coordinates consisting of atomic coordinates of the above amino acids of one of the two EGFR proteins forming a dimer. Moreover, at least, as long as amino acids creating an interaction important in dimerization are contained, some of the above amino acids, or one or more amino acids other than the amino acids listed above, may be contained. "Correspond to" means that given amino acid numbers correspond to the amino acid sequence shown in SEQ ID NO: 1 regarding the amino acid residues of EGFR, and regarding the amino acid residues of EGF, given amino acid numbers correspond to the amino acid sequence shown in SEQ ID NO: 2.

Examples of amino acids creating an interaction important in dimerization include Thr249, Tyr246, and Gln252 of the 1st EGFR and Asn86, Cys283, and Ala286 of the $2^{nd}$ EGFR, among the EGFR proteins forming a dimer. However, since amino acids creating an interaction important in dimerization may differ depending on methods employed for analyzing interfaces, examples of such amino acids are not limited to the above examples. As a preferred example, it is defined that amino acids composing a dimerization site may contain any one or more amino acids, as long as they contain amino acid residues corresponding to at least Thr249, Tyr246, and Gln252 of the $1^{st}$ EGFR, and Asn86, Cys283, and Ala286 of the $2^{nd}$ EGFR, where the two EGFR proteins form a dimer. Preferred specific examples thereof are shown in the structure coordinates (yk) to (ym). Moreover, residues (Glu293, Arg285, Arg405, Arg273, Asp254, and Gly458) that do not participate in direct interaction in dimerization, but in changeover of amino acid interaction like a switch when a ligand-dependent conformational change takes place, can also be said to be amino acids creating an interaction important in dimerization. Examples of a dimerization site consisting of such amino acid residues are shown in the structure coordinates (yn) to (yp). Furthermore, "amino acid residues adjacent thereto" means amino acid residues that are present at a distance of within 5 Å, and preferably within 3 Å, from other amino acid residues. The "receptor dimerization site" of (zb) includes an EGFR dimerization site, but is not limited thereto. Sites important for the exertion of protein functions, such as a dimerization site, may be conserved structurally at a high level regardless of differences among families or species. Hence, ligand-receptor complex that form a complex with a mechanism similar to that for EGF/EGFR are thought to have structures equivalent to those of the EGFR dimerization sites of the present invention. Therefore, the present invention also provides the coordinates of receptor dimerization sites of such ligand-receptor complexes that form a complex with a mechanism similar to that of EGF/EGFR. Examples of such ligand-receptor complexes include receptors belonging to the ErbB family.

Appropriate examples of the structure coordinates of an EGF-EGFR binding site are structure coordinates consisting of atomic coordinates of amino acid residues corresponding to the following (A) and (B):

(A) His10, Asp11, Tyr13, Leu15, His16, Met21, Ile23, Ala25, Leu26, Lys28, Ala30, Cys31, Asn32, Cys33, Val35, Tyr37, Ile38, Gly39, Glu40, Arg41, Gln43, Tyr44, Arg45, Asp46, Leu47, Lys48, and Trp49 of EGF; and (B) Asn12, Lys13, Leu14, Thr15, Gln16, Leu17, Gly18, Asp22, Arg29, Tyr45, Ala68, Leu69, Tyr89, Glu90, Leu98, Ser99, Tyr101, Leu325, His346, Leu348, Pro349, Val350, Asp355, Ser356, Phe357, Thr358, Leu382, Gln384, Gln408, His409, Gln411, Phe412, Ala415, Val417, Ile438, and Lys465 of EGFR. Moreover, at least, as long as amino acids creating an interaction important in EGF-EGFR binding are contained, some of the amino acids listed above, or one or more amino acids other than the amino acids listed above, may be contained. Furthermore, since sugar chains or water molecules other than amino acids may play an important role in an interaction, the structure coordinates of an EGF-EGFR complex or binding sites may appropriately contain atomic coordinates of such sugar chains or water molecules.

Examples of amino acids creating an interaction important in EGF-EGFR binding include Tyr13, Glu40, Arg41, Asp46, and Leu47 of EGF and Phe357, Lys13, Asp355, Arg29, Leu382, Ala415, and Val417 of EGFR as shown in FIG. 9. However, since amino acids creating an interaction important in EGF-EGFR binding may differ depending on methods employed for analyzing interfaces, examples of such amino acids are not limited to the above amino acids. As a preferred example, it is defined that amino acids composing an EGF-EGFR interaction site may contain any one or more amino acids, as long as they contain a set of amino acid residues of EGF and EGFR listed in any one of structure coordinates (ya-1), (yb-1), and (yc-1). Preferred specific examples thereof are shown in the structure coordinates (ya) to (yh).

Furthermore, "amino acid residues adjacent thereto" means amino acid residues that are present at a distance of within 5 Å, and preferably within 3 Å, from other amino acid residues. The "ligand-receptor binding site" of (za) includes an EGF-EGFR binding site, but is not limited thereto. Sites important for the exertion of protein functions, such as a ligand-receptor binding site, may be conserved structurally at a high level regardless of differences among families or species. Hence, ligand-receptor complexes that form a complex with a mechanism similar to that for EGF/EGFR are thought to have structures equivalent to those of the EGF-EGFR binding sites of the present invention. Therefore, the present invention also provides the coordinates of ligand-receptor binding sites of such ligand-receptor complexes that form a complex with a mechanism similar to that of EGF/EGFR. Examples of such ligand-receptor complexes include receptors belonging to the ErbB family.

The "structure homologue" of (zc) refers to a ligand-receptor complex that is structurally analogous to an EGF-EGFR complex. Being structurally analogous refers to having structure similarity in at least a receptor dimerization site and/or a ligand-receptor binding site. "Having similarity" means to have a structure which is specified by structure coordinates characterized in that a root mean square deviation of α carbon atomic coordinates is 1.5 Å or less when the structure coordinates are superimposed on those of a peptide chain of the EGF-EGFR complex. Examples of structure homologues include ligand-receptor complexes that form a complex with a mechanism similar to that for EGF/EGFR and are receptors belonging to the ErbB family.

For the structure coordinates of EGF-EGFR binding sites or EGFR dimerization sites specified by the amino acid residues (ya) to (yq), the structure coordinates in the form of amino acid coordinates shown in Table 1 or Table 2 can be referred, but the coordinates are not limited thereto. For example, structure coordinates of an EGF-EGFR complex, which are characterized in that a root mean square deviation of α carbon atomic coordinates is 2.0 Å or less when the structure coordinates are superimposed on those of the EGF-EGFR complex specified by the structure coordinates shown in Table 1 or Table 2 can be referred to. Moreover, structure coordinates of an EGF-EGFR complex that satisfy at least one feature of those described in the following (1) to (4) can also be referred:

(1) amino acid residues corresponding to Leu14, Tyr45, Leu69, Glu90, and Leu98 of EGFR are present at a distance from amino acid residues corresponding to Ile23, Leu26, and Lys28 of EGF so as to be able to interact with each other;
(2) amino acid residues corresponding to Val350, Asp355, and Phe357 of EGFR are present at a distance from amino acid residues corresponding to Tyr13, Leu15, and Arg41 of EGF so as to be able to interact with each other;
(3) amino acid residues corresponding to Leu382, Gln384, Phe412, and Ile438 of EGFR are present at a distance from amino acid residues corresponding to Gln43, Arg45, and Leu47 of EGF so as to be able to interact with each other;
(4) amino acid residues corresponding to Asn86, Cys283, and Ala286 of a second EGFR protein are present at a distance from amino acid residues corresponding to Thr249, Tyr246, and Gln252 of a first EGFR protein where the two EGFR proteins form a dimer, so as to be able to interact with each other.

Here, "a distance . . . so as to be able to interact with each other" is within 5 Å, and preferably within 3 Å.

Furthermore, the three-dimensional structure of protein is defined by the relative spatial arrangement of atoms composing the structure. Thus, generation of structure coordinates is a convenient process necessary for handling the data of the three-dimensional structure on a computer or the like. Hence, as is clear to persons skilled in the art, structure coordinates obtained by rotating the structure coordinates (a) to (zc) and/or subjecting the same coordinates to translational operation also completely represent the same three-dimensional structure as that represented by the structure coordinates prior to such operation.

Moreover, the present invention provides a computer-readable storage medium (recording medium) wherein any of the above structure coordinates (a) to (zc) has been stored (recorded). Examples of the computer-readable storage medium are not specifically limited, as long as it can introduce the stored structure coordinates into various programs (e.g., a program utilizing structure coordinates) on a computer. For example, it may be an electric temporary storage medium referred to as a memory, or a semipermanent storage medium such as a floppy disk, a hard disk, an optical disk, a magneto-optic disk, or a magnetic tape.

The structure coordinates and the storage medium storing the structure coordinates of the present invention are useful, because they can be used for screening for or designing compounds having action to regulate EGFR activity (in this specification, also referred to as "substances regulating EGFR activity"). Furthermore, the present invention provides EGF/EGFR or an EGF-EGFR complex having a three-dimensional structure that is characterized by any one of the above structure coordinates (a) to (z).

3. Screening Method or Designing Method Using Structure Information

A method for screening for or designing a substance regulating EGFR activity using structure coordinates of an EGF-EGFR complex according to the present invention, comprises the following steps of:

(a) generating structure coordinates of a three-dimensional structure of a test substance; and
(b) superimposing the structure coordinates of (a) onto all or some of the structure coordinates of the EGF-EGFR complex in the same coordinate system so as to evaluate their state of fitting. Specifically, the method of the present invention involves fitting the above structure coordinates of the EGF-EGFR complex with structure coordinates representing the three-dimensional structure of any test substance on a computer, numerically expressing their state of fitting using, for example, empirical scoring functions as indices, and then evaluating the ability of the test substance to bind to EGFR and/or EGF. Here, as the structure coordinates of the EGF-EGFR complex, all the structure coordinates or some of the structure coordinates of an EGF-EGFR binding site, an EGFR dimerization site or the like can be utilized.

The method of the present invention can further comprise a step of subjecting a screened or designed substance regulating EGFR activity to biochemical assay so as to evaluate action to regulate EGFR activity.

In this specification, a substance regulating EGFR activity is referred to as an EGFR agonist or an EGFR antagonist. The EGFR agonist is referred to as a substance at least having activity to bind to EGFR, and preferably having activity to induce EGFR dimerization by its binding. The EGFR antagonist is referred to as a substance having activity to inhibit EGF-EGFR binding and/or activity to inhibit EGFR dimerization. Substances inhibiting EGF-EGFR binding by binding to EGF are also included in the examples of the EGFR antagonist. Substances having activity to promote or stabilize EGF-EGFR binding by binding to EGF so as to induce EGFR dimerization are included in the examples of the EGFR agonist. A preferred example of such an EGFR agonist is EGF.

The activity of the substance regulating EGFR activity to induce or inhibit EGFR dimerization (specifically, action regulating EGFR activity) can be confirmed by directly observing the success or failure of EGFR dimerization, and can also be confirmed by a method for detecting the success or failure of the process or the result (e.g., phosphorylation in the intracellular regions of EGFR and cell proliferation) of signal transduction that takes place by dimerization.

Examples of a test substance to be subjected to the screening method of the present invention include, but are not limited to, proteins, peptides, oligonucleotides, synthetic compounds, compounds derived from nature, fermentation products, cell extracts, plant extracts, and animal tissue extracts, and may be either novel substances or known substances.

3-1 Method for Identifying EGF-EGFR Binding Site and EGFR Dimerization Site

The present invention provides a method for identifying an EGF-EGFR binding site or an EGFR dimerization site in an EGF-EGFR complex using structure coordinates of the EGF-EGFR complex.

All the information regarding the structure coordinates of the EGF-EGFR complex is useful in the present invention. Extraction of particularly important information from the entirety of information results in much wider possibilities for the industrial applications thereof. Analysis of the crystal structure coordinates of the present invention makes it possible to specify amino acid residues at which EGF interacts with EGFR (EGF-EGFR binding site) and amino acid residues interacting upon EGFR dimerization (EGFR dimerization site). Moreover, it is also possible to extract properties or information particularly important in industrial applications by visually displaying molecular coordinates of the complex using existing molecular design software (e.g., Tripos, Inc.'s SYBYL™ and Acceirys Inc.'s InsightII™) and then extracting amino acid residues involved in the interaction.

Specifically, the method can comprise the steps of entering the structure coordinates of the EGF-EGFR complex into a computer, and specifying amino acid residues composing an EGF-EGFR binding site or an EGFR dimerization site through the analysis of the structure of the EGF-EGFR complex. Furthermore, the method may also comprise a step of visually displaying the three-dimensional structure of the EGF-EGFR complex on a computer. The step of specifying amino acid residues composing an EGF-EGFR binding site or an EGFR dimerization site through the analysis of the structure of the EGF-EGFR complex can be realized by analysis using visual observation and/or a computer program.

The structure coordinates obtained from the crystal of the EGF-EGFR complex according to the present invention are entered into a computer or a storage medium of the computer on which a computer program runs for expressing the three-dimensional structure coordinates of molecules, making it possible to express in detail the patterns of three-dimensional chemical interactions of the EGF-EGFR complex. Examples of the storage medium of the computer are not specifically limited, as long as they can introduce the structure coordinates obtained from a crystal of the EGF-EGFR complex to the program in the computer. For example, it may be an electric temporary storage medium referred to as a memory or a semipermanent storage medium such as a floppy disk, a hard disk, an optical disk, a magneto-optical disk, or a magnetic tape. Many computer programs for expressing the three-dimensional structure coordinates of protein molecules are commercially available, and these programs generally provide, for example, a means of entering the three-dimensional structure coordinates of molecules, a means of visually expressing the coordinates on a computer screen, a means of measuring each distance, bond angle, and the like between atoms within an expressed molecule, and a means of carrying out additional correction for the coordinates. Furthermore, it is also possible to use a program that is produced to be able to provide a means of calculating molecular structural energy based on the coordinates of a molecule, and a means of calculating free energy considering a solvent molecule such as a water molecule. InsightII™ and QUANTA™, which are computer programs marketed by Accelrys Inc., are examples of appropriate programs for this purpose, but the examples in the present invention are not limited to these programs. Moreover, the program is generally introduced into a computer referred to as workstation supplied by Silicon Graphics Inc., or Sun Microsystems Inc., and then used, but examples of a computer are not limited thereto. As structure coordinates, the structure coordinates (a) to (x) explained in section "2. Structure coordinates of EGF-EGFR complex" can be used.

The step of specifying amino acid residues composing an EGF-EGFR binding site or an EGFR dimerization site by visual observation and/or a computer program is a step of specifying amino acid residues participating in protein-protein interaction by analyzing the interface between protein molecules by visual observation and/or use of a computer program. At this time, amino acids participating in interaction are specified considering distance, strength, type, and the like regarding interaction between amino acid residues. For example, in the crystal structure of the complex, when amino acid residues of EGFR that are present at a distance of within several angstroms from each amino acid residue of EGF are extracted, amino acid residues on EGFR directly interacting with EGF can be extracted. Conversely, when amino acid residues in EGF that are present at a distance of within several angstroms from each amino acid residue of EGFR are extracted, amino acid residues on EGF directly interacting with EGFR can be specified. Furthermore, extraction of amino acid residues in EGFR that are present at a distance of within several angstroms from another EGFR protein, where the EGFR proteins form a dimer, makes it possible to specify amino acid residues important in EGFR dimerization.

For example, amino acid residues of EGF that are present at a distance of within 3 Å from EGFR are important in direct binding with EGFR. Conversely, amino acid residues in EGFR that are present at a distance of within 3 Å from EGF are important in direct interaction with the EGF molecule. Furthermore, amino acid residues in EGFR that are present at a distance of within 3 Å from another EGFR protein, where the EGFR proteins form a dimer, are important for EGFR dimerization.

Examples of interaction types include electrostatic interaction, hydrophobic interaction, Van der Waals interaction, and hydrogen bonds. In addition, not only simple specification of interaction based on distance, but also specification of interaction considering the orientation of amino acid side chains corresponding to each other is preferred. The strength of interaction is affected by distance, interaction type, orientation of side chains, the presence of water molecules, and the like. When analysis is made by a computer program, it is possible to use a program calculating the distance between amino acid residues, a program specifying the interaction type based on the types of two amino acid residues inferred to create interaction, or the like. However, when a plurality of amino acid residues capable of interacting with each other are present in close proximity, it may be difficult to determine which interactions of which residues are important in protein-protein interaction by calculation only. Hence, it is preferred to finally specify amino acids participating in interaction considering comprehensibly distance, strength, type, and the like regarding interaction between amino acid residues by visual observation.

The amino acid residues shown below are useful for analyzing interaction that is specified from the crystal structure analysis of the EGF-EGFR complex based on the distance for interaction.

(i) Examples of amino acid residues in EGF composing a binding site with EGFR His10, Asp11, Tyr13, Leu15, His16, Met21, Ile23, Ala25, Leu26, Lys28, Ala30, Cys31, Asn32, Cys33, Val35, Tyr37, Ile38, Gly39, Glu40, Arg41, Gln43, Tyr44, Arg45, Asp46, Leu47, Lys48, and Trp49

(ii) Examples of amino acid residues in EGFR composing a binding site with EGF Asn12, Lys13, Leu14, Thr15, Gln16, Leu17, Gly18, Asp22, Arg29, Tyr45, Ala68, Leu69, Tyr89, Glu90, Leu98, Ser99, Tyr101, Leu325, His346, Leu348, Pro349, Val350, Asp355, Ser356, Phe357, Thr358, Leu382, Gln384, Gln408, His409, Gln411, Phe412, Ala415, Val417, Ile438, and Lys465

(iii) Examples of amino acid residues in EGFR forming an EGFR dimerization site

Asn86, Gln194, Pro204, Ser205, Lys229, Phe230, Thr239, Pro242, Tyr246, Pro248, Thr249, Tyr251, Gln252, Met253, Ser262, Phe263, Gly264, Ala265, Tyr275, His280, Ser282, Cys283, Val284, Arg285, Ala286, and Lys303

Examples of EGF-EGFR binding sites and EGFR dimerization sites are not limited to the above examples.

As described above, an interface can also be defined as being composed of amino acid residues in EGFR that are present at a distance of within 3 Å from EGF. In addition, only amino acids that are important in interaction can also be defined as composing an EGF-EGFR binding site or an EGFR dimerization site while focusing on interaction type and strength. Specifically, results may differ depending on the method used for analyzing an interface. However, as long as the screening method according to the present invention can still be implemented, such interaction is encompassed in the scope of the present invention. Examples of extraction of amino acids important in interaction considering not only the distance between amino acid residues for interaction, but also interaction type and side chain orientation, are explained in FIGS. 9 and 10, Example 6, and the above section "2. Structure coordinates of EGF-EGFR complex."

3-2 Identification of EGF-EGFR Binding Site and Dimerization Site

Through the use of the method for identifying EGF-EGFR binding sites or EGFR dimerization sites in an EGF-EGFR complex using the structure coordinates of the EGF-EGFR complex, the present invention further provides the following methods:

I. a method for screening for a substance regulating EGFR activity, comprising the following steps of:
(1) identifying an EGF-EGFR binding site or an EGFR dimerization site using the structure coordinates of the EGF-EGFR complex;
(2) screening for a candidate substance regulating EGFR activity using the structure coordinates of the EGF-EGFR binding site or the EGFR dimerization site identified by (1); and
(3) subjecting the substance regulating EGFR activity obtained by (2) to biochemical assay so as to evaluate the action regulating EGFR activity.

II. a method for screening for a substance regulating EGFR activity, comprising the following steps of:
(1) identifying an EGF-EGFR binding site or an EGFR dimerization site using the structure coordinates of the EGF-EGFR complex;
(2) designing a pharmacophore of a substance regulating EGFR activity using the structure coordinates of the EGF-EGFR binding site or the EGFR dimerization site identified by (1);
(3) screening for the substance regulating EGFR activity using the pharmacophore obtained by (2); and
(4) subjecting the substance regulating EGFR activity obtained by (3) to biochemical assay so as to evaluate the action regulating EGFR activity.

III. a method for designing a substance regulating EGFR activity, comprising the following steps of:
(1) identifying an EGF-EGFR binding site or an EGFR dimerization site using the structure coordinates of the EGF-EGFR complex;
(2) designing a pharmacophore of a substance regulating EGFR activity using the structure coordinates of the EGF-EGFR binding site or the EGFR dimerization site identified by (1);
(3) designing a compound using the pharmacophore obtained by (2); and
(4) subjecting the compound obtained by (3) to biochemical assay so as to evaluate the action regulating EGFR activity.

These methods are explained in detail below.

3-3 Screening Method Using Structure Coordinates of EGF-EGFR Complex

A method for screening for a substance regulating EGFR activity using structure coordinates of an EGF-EGFR complex according to the present invention comprises the following steps of:
(a) generating structure coordinates of a three-dimensional structure of a test substance; and
(b) superimposing the structure coordinates of (a) onto all or some of the structure coordinates of an EGF-EGFR complex in the same coordinate system so as to evaluate their state of fitting. Specifically, such a method involves fitting the above structure coordinates of the EGF-EGFR complex to structure coordinates representing a three-dimensional structure of any test substance on a computer, expressing their state of fitting numerically using, for example, empirical scoring functions as indices, and then evaluating the binding ability of the test substance to EGFR and/or EGF.

As described above, the structure coordinates of the EGF-EGFR complex are used, the shape of an EGF-EGFR binding site or an EGFR dimerization site is assigned, and then a compound that can bind to the site can be subjected to computer screening using commercial package software such as DOCK (Ewing, T. J. et al., "DOCK 4.0: Search Strategies for Automated Molecular Docking of Flexible Molecule Database," J. COMP. AIDED MOL. DES. 15(5):411-428 (2001)), AutoDock (Morris, G. M., et al., "Automated Docking Using a Lamarckian Genetic Algorithm and Empirical Binding Free Energy Function," J. COMPUTATIONAL CHEM. 19:1639-1662 (1998)), Ludi™, or LigandFit™. For example, amino acid residues in EGFR that can interact with EGF (Asn12, Lys13, Leu14, Thr15, Gln16, Leu17, Gly18, Asp22, Arg29, Tyr45, Ala68, Leu69, Tyr89, Glu90, Leu98, Ser99, Tyr101, Leu325, His346, Leu348, Pro349, Val350, Asp355, Ser356, Phe357, Thr358, Leu382, Gln384, Gln408, His409, Gln411, Phe412, Ala415, Val417, Ile438, and Lys465) provide pockets or clefts to which substances regulating EGFR activity (agonist or antagonist) can bind. Thus, it becomes possible to conduct computer screening using such sites as an aid.

The step of superimposing structure coordinates of a test substance onto all or some of the structure coordinates of the EGF-EGFR complex in the same coordinate system so as to evaluate their state of fitting can be implemented using the above-mentioned commercial packaging software and a computer system on which the software can run. The computer system appropriately comprises various means necessary for running target software such as a storage means for storing structural formulae of compounds, a means for generating coordinates of three-dimensional structures of compounds, a storage means for storing structure coordinates of compounds, a storage means for storing the structure coordinates of the EGF-EGFR complex, a storage means for storing evaluation results, a means for displaying the contents of each storage means, a means for data entry such as a keyboard, a means for displaying, such as a display, and a central processing unit.

In this specification, a specific example using DOCK as software for analysis is shown. Any software may be used, as long as it makes a simulation of the docking procedure of a ligand to a protein possible on a computer. For example, software programs such as FlexX™ (Tripos, Inc.), Ligand-Fit™ (Accelrys Inc.), or Ludi™ (Accelrys Inc.) can be used.

First, a virtual spherical body referred to as a sphere is disposed using a SPHGEN program in the periphery of a pocket and a cleft to which a substance regulating EGFR activity (agonist or antagonist) is thought to be able to bind. This sphere functions as an anchor for docking of a ligand. In addition, sites at which spheres are generated can be limited to specific pockets or specific clefts, or spheres can be generated at a plurality of sites. When too many spheres are generated, adjacent spheres can be manually removed.

Next, grids are generated at a portion and the periphery thereof where EGF interacts with EGFR using a GRID program, so as to express an electronic and steric environment for receptor residues within an assigned range as a scalar value on each grid. In addition, the force field of AMBER™ (Pearlman, D., et al., "Amber, a Computer Program for Applying Molecular Mechanics, Normal Mode Analysis, Molecular Dynamics and Free Energy Calculation to Elucidate the Structures and Energies of Molecules," COMP. PHYS. COMMUN. 91:1-41 (1995)) or the like is utilized to calculate each grid value, but is not always limited to AMBER™ and other force fields may also be used. Furthermore, depending on the protein side shape, adjustment can also be made by altering grid information so as to express docking of a compound in a more realistic form.

Next, a search is conducted on compound database. Using the DOCK program, a compound that is located in the vicinity of spheres existing in the periphery of a pocket and a cleft and takes a three-dimensional conformation so as not to repel steric elements or electronic elements on the grids is searched for. At this time, the three dimensional conformation of the docked compound is optimized by a conformation-generating function integrated in the DOCK program. However, whether or not appropriate docking is finally conducted is comprehensively determined based on empirical judgment made using scores at the time of docking, visual observation, and the like. In this manner, a series of selected compound groups that were judged to be able to appropriately conduct docking can be considered as substances regulating EGFR activity (agonist or antagonist) at a certain probability.

The above method promotes more efficient drug discovery and drug development. Specifically, predicting the arrangement of structure coordinates that fit the properties and shapes of the interaction sites of an EGF-EGFR complex and the selection by calculation of a compound having a structure capable of agreeing with the putative structure coordinates make it possible to efficiently select an activity-controlling substance specific to EGFR from among many compounds.

A candidate substance (test substance) to be confirmed whether or not the substance has activity-regulating action for EGFR may be either a known or a novel substance. The structure, origin, physical properties, and the like thereof are not specifically limited. Such a candidate substance may be any of a native compound, a synthetic compound, a high molecular weight compound, a low molecular weight compound, a peptide, or a nucleic acid analogue. In terms of future pharmaceutical development, a low molecular weight compound is preferred. For example, compound information registered with the Available Chemicals Directory (ACD) (MDL information systems, Inc., San Leandro, Calif.), CMC (Comprehensive Medical Chemistry), or MDDR (MDL Drug Data Report, or the like) is beneficial.

As a program to generate three-dimensional structure coordinates of such low molecular weight compounds, programs such as CORINA™ (Molecular Networks GmbH), Concord™ (Tripos, Inc.), Converter™, or the like can be utilized. The thus generated coordinates of a low molecular weight compound and those of the EGF-EGFR complex can be automatically bound using a molecular docking package such as DOCK or the like, or can be interactively bound using software for displaying molecules such as InsightII™. At this time, as indices for evaluating their state of fitting using these programs, calculated free energy values, empirical scoring functions, shape complementarity, and the like, evaluated for the entire compound-bound complex, can be freely chosen and used. By the use of the indices, the quality of the binding can be evaluated objectively.

In the method for screening for a substance regulating EGFR activity using the structure coordinates of the EGF-EGFR complex of the present invention, as the structure coordinates, structure coordinates of an EGF-EGFR binding site or an EGFR dimerization site identified by the method described in section "3-1" can be used.

Examples of the structure coordinates of the EGF-EGFR binding site or the EGFR dimerization site include the structure coordinates of each (ya) to (yh) and (yj) to (yp) explained in section "2. Structure coordinates of EGF-EGFR complex." Furthermore, through the use of structure coordinates of a ligand-receptor complex obtained using the structure coordinates of the EGF-EGFR complex by a later-described homology modeling method or the molecular replacement method, screening of the receptor agonist and the receptor antagonist can be conducted by a similar method.

3-4 Method for Screening for and Method for Designing Substance Regulating EGF Activity Using Pharmacophores A pharmacophore is a representation of physicochemical features of a compound, which is required for binding with a target protein. A pharmacophore represents structural and physicochemical features of a compound as spheres representing pharmacophoric features, so that it can be defined by determining relative distances among spheres representing pharmacophoric features or can be defined by determining relative distances among specific functional groups. Furthermore, a pharmacophore can be defined freely using techniques that can be generally employed by persons skilled in the art, and the method therefor is not limited to the above methods.

A sphere representing pharmacophoric features means a spatial region holding various physicochemical properties including hydrophobicity, electrostatic property, and capability of forming hydrogen bonds. For example, according to Catalyst™, which is a pharmacophore construction program (Accelrys Inc., San Diego, Calif.), eight types of spheres representing pharmacophoric features are shown: "Hydrogen-bond Acceptor (furthermore, Hydrogen-bond Acceptor lipid can also be classified)," "Hydrogen-bond Donor," "Hydrophobic (furthermore, Hydrophobic Aromatic and Hydrophobic aliphatic can also be classified)," "Negative Charge," "Negative Ionizable," "Positive Charge," "Positive Ionizable," and "Ring Aromatic." Users of the program can add new definitions, and can utilize those other than the above components. Specifically, having a hydrophobic region, a hydrogen bond receptor region, a positive ion region, a ring aromatic region, and the like are specified as physicochemical properties. Spheres representing pharmacophoric features can be expressed as a spherical region with Å radius having these physicochemical properties. Examples of atoms and functional groups fitting each sphere representing pharmacophoric features are defined in the manual attached to a program such as Catalyst™ (Accelrys Inc., Catalyst Documentation Release 4.5, 1999).

In other words, the substance regulating EGFR activity of the present invention is specified as a substance that can selectively fit protein-protein interaction sites (including a ligand-receptor interface and a receptor-receptor interface) of the EGF-EGFR complex, and is represented by a chemical structure that satisfies the structure coordinates of spheres having certain physicochemical properties and corresponding to each other.

By analyzing the structure information of an EGF-EGFR co-crystal and specifying properties provided by the steric arrangement of the previously described amino acid residues or the three-dimensional arrangement of structural water as a pharmacophore, a substance regulating EGFR activity (agonist or antagonist) can be screened for by a computer. Moreover, to form a complex, water molecules (structural water) existing between molecules may play a role in the formation of a complex, and protein-protein interaction mediated by such water molecules is specified by graphics observation or the like. Furthermore, among amino acid residues and water molecules which can participate in interaction, specifically, the analysis of sites forming hydrophobic interaction, ionic bonds, hydrogen bonds, amino acid residues, and molecular shapes (pockets and clefts) provided by the active conformation of EGF and EGFR in the structure of the complex make it possible to present pharmacophores required for molecular design and computer screening. Examples of interactions of the EGF-EGFR complexes useful for the construction of pharmacophores are shown in FIGS. 9 and 10. The amino acid residues shown in these figures are examples of the amino acids that create important interaction upon EGF-EGFR binding and EGFR dimerization, respectively.

3-4-1 Method for Designing Pharmacophores

The present invention provides a method for designing a pharmacophore, which uses structure coordinates of an EGF-EGFR complex. Here, "pharmacophore" means the pharmacophore of a substance regulating EGFR activity. The method for designing a pharmacophore can comprise the steps of analyzing a three-dimensional structure represented by the structure coordinates of the EGF-EGFR complex (by visual observation and/or an appropriate computer program), specifying a partial structure (e.g., amino acid residues, structural water, pockets, and clefts) that can be used as a pharmacophore; and converting the partial structure into spheres representing pharmacophoric features, so as to generate the pharmacophore. The step of specifying a partial structure that can be used as a pharmacophore is conducted according to the means explained in "3-1." The step of converting the partial structures into spheres representing pharmacophoric features, so as to generate a pharmacophore, can be implemented using commercial software such as Catalyst and a computer system on which the software can run.

By setting relative positional relationships on the three-dimensional space of spheres representing pharmacophoric features, a search formula (pharmacophore) on the software program Catalyst™ can be constructed. In addition, a specification method may be conducted using coordinates (x, y, z) or using the collection of slant distances connecting each point. Moreover, when an actual distance that enables interaction with a receptor, calculation errors, and the like are taken into consideration, it is not necessary for each distance between chemical functions to be always precisely defined. According to Catalyst™, positions of each chemical function are generally defined by a radius of a sphere ranging from 1.5 Å to 2.0 Å when each point is a center, or a direct distance between ±3 Å and 4 Å connecting each point. These numerical values can also be changed as appropriate.

In the method for designing a pharmacophore using the structure coordinates of the EGF-EGFR complex of the present invention, as the structure coordinates of the EGF-EGFR complex, the structure coordinates of EGF-EGFR binding sites or EGFR dimerization sites identified by the method described in "3-1" can be used. Examples of the structure coordinates of the EGF-EGFR binding sites or the EGFR dimerization sites include the structure coordinates (ya) to (yh) and (yj) to (yp) that are each explained in section "2. Structure coordinates of EGF-EGFR complex." Furthermore, through the use of structure coordinates of a ligand-receptor complex obtained using the structure coordinates of the EGF-EGFR complex by the homology modeling method or the molecular replacement method as described below, pharmacophores useful in screening for the receptor agonist and antagonist can be designed by a similar method.

Furthermore, based on compounds showing EGFR-activity-regulating action obtained by the above screening method using a computer or the above experimental screening method, a pharmacophore can be defined by expressing common structural characteristics among these compounds, and then determining the relative distance between spheres representing pharmacophores. It can also be defined by determining the relative distance between specific functional groups.

Moreover, when sites binding to a protein differ depending on compounds, there may be no physicochemical properties that are common to all compounds. In this case, there is a need to perform appropriate clustering of compounds, and then to determine common physicochemical properties within each cluster.

We have succeeded in designing a pharmacophore of a substance regulating EGFR activity utilizing the structure coordinates of the EGF-EGFR complex. A specific pharmacophore is disclosed in Example 5 and Example 6.

3-4-2 Screening Method Using Pharmacophores

The present invention provides a method for screening for a substance regulating EGFR activity using a pharmacophore. The use of a specified pharmacophore makes it possible to discover an EGFR agonist or an EGFR antagonist. Here, a case using Catalyst™ (Accelrys Inc.) as software for analysis is described. However, any software may be used, as long as it enables extraction of chemical functions from a ligand and searching for a compound that can have spatial arrangement analogous to that of the extracted chemical functions. For example, Unity™, which is a module of SYBYL™ (Tripos, Inc.), may also be used. At this time, when clustering of compounds is required, a program such as Daylight Clustering Package™ (Daylight Chemical Information Systems, Inc., Aliso Viejo, Calif.) can be used.

Using the designed pharmacophore, a previously prepared compound structure database is used for computer screening. The pharmacophore information and spatial arrangement of the three-dimensional structure of a compound are compared, and then whether or not the compound satisfies the properties of the pharmacophore is determined by calculation. An advantage of computer screening is that a search object is a partial collection of all the theoretically conceivable compounds. In general, a corporation's own compound database or a commercial compound database, such as Available Chemical Directory (MDL Information Systems, Inc.), databases produced by each compound sales companies or agents, and a database of virtual compounds generated using virtual combinatorial synthesis techniques, a database of compounds derived from natural products, a drug database, is converted for use in computer search.

A group of hit compounds selected by the above computer screening may bind to the pharmacophore of EGFR, so that they may be EGFR agonists or antagonists (substances regulating EGFR activity) at a certain probability.

The screening method using a pharmacophore can comprise the steps of (1) generating structure coordinates of a three-dimensional structure of a test substance, and (2) superimposing the structure coordinates of (1) onto structure coordinates of spheres specifying a pharmacophore in the same coordinate system, so as to evaluate their fitting state. Here, a pharmacophore indicates the pharmacophore of the substance regulating EGFR activity designed in "3-4-1." At this time, preferably, the structure coordinates of (1) match the relative arrangement and features of at least 3 or more spheres representing pharmacophoric features. These steps can be implemented using the above commercial software and a computer system on which the software can run.

In addition, the database of a group of compounds selected by means of search formulae is generated, and then the protein structure is applied to commercial docking software so as to be able to increase the selection rate.

In addition, compounds that bind to the EGF-EGFR complex can be used as filters effective for computer screening using DOCK or the like, and can also be subjected De Novo design, which involves arranging fragments fitting each pharmacophore, and then binding each fragment at an appropriate functional group so as to construct a compound.

3-4-3 Design Method Using Pharmacophores

The use of the structure coordinates of the EGF-EGFR complex of the present invention enables molecular design (e.g., increased activity and provision of selectivity) of substances regulating EGFR activity (agonists and antagonists).

Construction of a binding model of a compound selected in screening or a derivative thereof enables the use of the model for optimizing induction of the thus obtained compound. For example, a docking model structure of an EGFR agonist or an EGFR antagonist obtained by screening to EGF or EGFR can also be predicted on a computer. This model structure is very useful for discovering orientation for induction that enhances interaction between a compound and an amino acid residue adjacent thereto, because it can present an appropriate orientation for improving metabolism, toxicity, and the like without affecting the activity. Furthermore, the model structure also provides the most useful information for considering differences among species in pharmacological experiments or metabolism experiments or supporting induction and synthesis for improving selectivity against a target protein for the purpose of side-effect alleviation.

The method for designing a substance regulating EGFR activity using a pharmacophore can comprises the steps of: (1) generating each group of fragments having functional groups corresponding to each sphere representing pharmacophoric features; and (2) binding each fragment selected one-by-one from each group of the fragments generated in (1), so as to design a compound. Furthermore, the method may also comprises the steps of: (3) superimposing structure coordinates of the designed compound onto the structure coordinates or a pharmacophore of the EGF-EGFR complex in the same coordinate system so as to evaluate their fitting state; (4) substituting one or more fragments of the compound with a fragment(s) having a property of enhancing or attenuating interaction with amino acid residues adjacent thereto; and (5) repeating steps (3) and (4).

Step (1) is for generating a group of fragments having functional groups corresponding to each sphere representing pharmacophoric features. In the present invention, a fragment means a partial structure of a compound. For example, fragments having functional groups corresponding to spheres representing features of one pharmacophore are collected as a group of fragments. Furthermore, fragments having functional groups corresponding to spheres representing features of another pharmacophore are collected as a group of fragments. In this manner, each fragment group having functional groups corresponding to each condition is generated. At this time, fragments having functional groups that match a plurality of pharmacophores, or fragments simultaneously having functional groups matching one pharmacophore and functional groups matching another pharmacophore, may also be collected. A manner of collecting fragments is not specifically limited. For example, fragments may be collected from substances regulating EGFR activity. A new fragment may also be generated by a procedure such as addition of a substituent to one collected fragment, extension or reduction of carbon chains, substitution of an atom, or the like. At this time, it is more useful to generate fragments such that a known substance regulating EGFR activity is improved. For example, water molecules (structural water) existing between EGFR and a substance regulating EGFR activity may also play a role in the formation of a complex of the two, and the EGFR-substance regulating EGFR activity interaction mediated by such molecules can be specified by graphics observation or the like. Furthermore, such interaction can be observed by analyzing amino acid residues and water molecules that can participate in interaction, in particular, sites or amino acid residues forming hydrophobic interaction, ionic bonds, or hydrogen bonds, and furthermore, a molecular shape given by the active conformation of a substance regulating EGFR activity in the structure of the complex. In this manner, it is possible to create new fragments in order to discover the orientation for induction that enhances interaction between a known substance regulating EGFR activity and amino acid residues adjacent thereto; or in order to present orientation appropriate for proceeding with pharmacological improvement in such areas as metabolism and toxicity without affecting the activity.

Next, a compound model is built by binding fragments selected one-by-one from the above-generated fragment group. For example, on paper, fragments selected one by one from each fragment group determined in step (1) may be bound to each other so as to build a compound model. Preferably, a compound model is built using computer software.

Software used herein may be any software, as long as it can build the structure of a compound. For example, the program Ludi™ (Accelrys Inc.), CombiLibMaker™, which is a module of Sybyl™ (Tripos, Inc.), or the like can be used.

Binding of fragments includes direct binding of fragments to each other, and binding via a linker that is used between fragments. Examples of a linker to be used herein are not specifically limited, and include a group of hydrocarbon having straight chains or side chains, and groups where the above group of hydrocarbons is substituted with a hetero compound.

Furthermore, by designing a peptide having amino acid residues existing in a continuous sequence in EGF or EGFR and participating in interaction, a low molecular weight compound can also be mimicked based on the structure information on the EGF-EGFR crystal. For example, a partial sequence such as Cys33-Trp49 of EGF (CVVGYIGERC-QYRDLKW: SEQ ID NO: 10), Ser11-Asn32 in domain I of EGFR(SNKLTQLGTFEDHFLSLQRMFN: SEQ ID NO: 11), Pro241-Thr266 in domain II of EGFR (PPLMLYNPT-TYQMDVNPEGKYSFGAT: SEQ ID NO: 12), or Leu345-Leu363 in domain III (LHILPVAFRGDSFTHTPPL: SEQ ID NO: 13) can exert action to regulate activity, such as agonist activity or antagonist activity. Thus, a peptide mimic of the sequence is created to degrade the lower molecular weight thereof, so that it can be optimized as a medicament.

The methods explained in "3-1" to "3-4" can be used not only individually, but also in combination or repeatedly. For example, after screening for a compound using the structure coordinates of the EGF-EGFR complex is conducted, the selected compound can further be subjected to the screening method using a pharmacophore. Combination or repetition of a plurality of techniques makes it possible to identify a more precise substance regulating EGFR activity.

3-5 Evaluation by Biochemical Assay

The above-explained method for designing or screening for a substance regulating EGFR activity using the structure coordinates of the EGF-EGFR complex, or the above explained method for designing or screening for a substance regulating EGFR activity using a pharmacophore enables rapid screening on a computer. However, although a compound group selected by screening utilizing a computer has expected activity at a higher probability, all compounds do not always have such activity. Thus, it is preferable to evaluate many compounds experimentally (using biochemical assay). Specifically, the screening or the design method using structure information and pharmacophores can be said to be a method for screening for a "candidate" substance regulating EGFR activity when it does not contain a step of subjecting compounds to biochemical assay.

Hence, when a compound to be experimentally evaluated based on the results of computer screening is selected, it is required to determine the number of compounds to be actually evaluated experimentally considering the number of active compounds that are expected as a result of evaluation.

In general, a program for conducting computer screening contains an evaluation system. However, such an evaluation system often involves original procedures tailored to the algorithm of the corresponding program. When the activity value of each compound is obtained by means of an evaluation system, compounds to be subjected to experimental evaluation can be selected based on the activity values. However, there are many evaluation systems by which activity values are not obtained and only empirical numerical values are obtained. In the meantime, the purpose of computer screening is to narrow down the number of compounds to be subjected to experimental evaluation, and it is meaningful to select top compounds ranked by an evaluation system in numbers that enable experimental evaluation. For example, when a probability that a compound selected by computer screening has expected activity is supposed to be between 5% and 30%, approximately 30 to 200 candidate compounds are selected to obtain 10 compounds that are substances controlling activity. Furthermore, approximately 160 to 1000 candidate compounds are selected to obtain 50 compounds that are substances controlling activity. At this time, to confer diversity on compounds controlling activity that are finally obtained, it is also meaningful to conduct clustering of top compounds ranked by evaluation based on similarities in structure, physical property, and the like, and then to select from each cluster the number of compounds to be subjected to experimental evaluation.

Specifically, further subjecting of (candidate) substances regulating EGFR activity selected by screening on a computer to biochemical assay using cells expressing EGFR or EGFR makes it possible to more effectively select a substance regulating EGFR activity. Whether or not a test substance exerts action regulating EGFR activity upon the use of biochemical assay can be determined by examining if there is a difference in protein activity between a case where the compound has been added to a system by which protein activity can be confirmed and a case where no compounds have been added. Having action regulating activity indicates that there is a difference between assayed protein activity values of a group to which a test compound has been added and those of a group to which no test compounds have been added. For example, having action regulating activity means to have an inhibition (or suppression) rate or enhancement (or promotion) rate calculated by the following formula of 10% or more, preferably 30% or more, more preferably 50% or more, further more preferably 70% or more, and particularly preferably 90% or more.

Inhibition (suppression) rate or enhancement (promotion) rate (%)=absolute value of (assayed value of the group to which no compounds have been added−assayed value of a group to which a test compound has been added)/assayed value of the group to which no compounds have been added× 100

Here, whether action is inhibition action or enhancement action and assayed values can be appropriately determined based on a system type by which protein activity can be confirmed. For example, when a system by which protein activity can be confirmed is the method of biochemical assay example 6 shown below, absorbance can be used. In a case where the assayed values of a group to which a test substance has been added are less than the assayed values of a group to which no test substances have been added, the test substance can be said to be an EGFR antagonist. In a case where assayed values of a group to which a test substance has been added are greater than the assayed values of a group to which no test substances have been added, the test substance can be said to be an EGFR agonist. When a measurement system contains background or noise values, an assayed value can be obtained by subtracting such background or noise values from the original assayed value.

Examples of biochemical assay are as shown below, but are not limited thereto.

BIOCHEMICAL ASSAY EXAMPLE 1

EGF Receptor Binding Assay

Cells expressing EGF receptors at a high level represented by A431 (human squamous cell carcinoma) cells and the like or soluble EGF receptors are immobilized on a plate. EGF labeled with europium and a test substance are added to each well, followed by incubation for a given time period. After incubation, the plate is washed, a DELFIA enhancement reagent is added, and then time-resolved fluorescence is measured. Fluorescence count of a well to which DMSO has been added instead of the test substance is used as a control. A test substance showing a count lower than the control count can be screened for as a substance inhibiting EGF binding.

Similarly, receptor binding assay can also be conducted using EGF labeled with RI or the like.

BIOCHEMICAL ASSAY EXAMPLE 2

ELISA Assay

Cells expressing EGF receptors at a high level including A431 cells or soluble EGF receptors are immobilized on a plate. EGF and a test substance are added to each well, followed by incubation for a given time period. After incubation, the plate is washed, anti-EGF antibodies labeled with HRP are added, and then incubation is further conducted. The plate is washed again, and then a substrate solution is added thereto, thereby initiating an enzyme reaction. After a given time period, the reaction is stopped, and then absorbance is measured. Using the absorbance of a well to which DMSO has been added instead of the test substance as a control, a test substance showing a count lower than that of the control can be screened for as a substance inhibiting the binding of EGF.

BIOCHEMICAL ASSAY EXAMPLE 3

Binding Experiment Using BIACOR®

Soluble EGF receptors are immobilized on a sensor chip, and then test substances are introduced onto the chip through the BIACORE® (registered mark) microchannel system. Changes in quantity on the sensor chip surface are detected by surface plasmon resonance, so as to be able to screen for test substances specifically binding to the EGF receptor.

BIOCHEMICAL ASSAY EXAMPLE 4

Phosphorylation Experiment for EGF Receptor (Western Blotting)

Cells expressing EGF receptors at a high level including A431 cells are inoculated on a plate. EGF and test substances are added to each well, followed by incubation for a given time period. After incubation, the cells are lysed using a Laemmli buffer (Laemmli, U.K., 1970, NATURE 227: 680-685). Protein is separated by SDS-PAGE, and then blotted onto a membrane. Tyrosine-phosphorylated EGF receptors are caused to emit using a secondary antibody labeled with an anti-phosphorylated EGF receptor antibody, HRP, or the like, and an appropriate substrate solution, so that they are detected on X-ray film or the like. The quantity (darkness of a band detected) of the phosphorylated receptors in cells to which DMSO has been added instead of the test substances is used as a control, so that test substances showing bands which are lighter in color than that of the control can be screened for as agents inhibiting the activation of EGF receptor.

Furthermore, a test substance showing a band which is darker in color than that of the control can be screened for as an agent activating an EGF receptor.

BIOCHEMICAL ASSAY EXAMPLE 5

Reporter Gene Assay

A plasmid is constructed wherein a luciferase gene is ligated downstream of the promoter region of a gene such as c-fos or c-myc whose transcription is induced by EGF stimulation. The plasmid is transfected into cells expressing EGF receptors represented by A431 cells or the like, thereby producing recombinant cells expressing a reporter gene transiently or permanently by EGF stimulation. EGF and test substances are added to the recombinant cells, and then luciferase activity is assayed after a given time period. The luciferase activity of a well to which DMSO has been added instead of the test substances is used as a control, so that test substances showing luciferase activity lower than that of the control can be screened for as agents inhibiting the activation of EGF receptor.

Furthermore, a test substance showing luciferase activity that is higher than that of the control can also be screened for as an agent activating an EGF receptor.

BIOCHEMICAL ASSAY EXAMPLE 6

Cell Proliferation Assay

Cells showing EGF-dependent proliferation represented by A431 cells, SiHa cells (human squamous cell carcinoma), and the like are inoculated on a plate. EGF and test substances are added. A few days later, viable count is quantified by an MTT method or the like. Absorbance of a well to which DMSO has been added instead of the test substances is used as a control, so that test substances showing absorbances lower than that of the control can be screened for as agents inhibiting the activation of EGF receptor. Furthermore, a test substance showing absorbances higher than that of the control can be screened for as an agent activating an EGF receptor.

The effect and the action of EGF have been shown to be induced via EGF receptors existing on cell membranes. It is expected that a compound binding to an EGF receptor so as to activate it has physiological activity and pharmacological activity equivalent to those of EGF. Evaluation examples of the biological activity (drug efficacy experiment) of an agent activating an EGF receptor are shown below.

EXPERIMENT EXAMPLE 1

Action on Tumor Transplantation Model Mouse

Colon-26 (carcinoma of mouse colonic gland) or A431 cells are transplanted subcutaneously in the abdomens of BALB/c female mice. After a given time period, carcinoma size, that is, the major axis ("a" mm) and the minor axis ("b" mm) of each tumor, are measured, and then the carcinoma weight is calculated by the following formula.

Carcinoma weight (mg)=$ab^2/2$ (Since these cancerous tumors generally exist in the form of spheroids, a formula for calculating the volume of a spheroid is employed. In addition, volume=weight is employed, wherein the specific gravity of a cancer cell is supposed to be approximately 1.)

After carcinoma weight is weighed immediately before the administration of a test substance, the test substance is administered to each group, and then changes with time in the weight of transplanted carcinoma cells are measured. The agent activating an EGF receptor obtained by the present invention increases or decreases carcinoma weight.

EXPERIMENT EXAMPLE 2

Action on Acute Hepatic Disorder Model Mouse

A test substance is administered to ddY male mice. 30 minutes later, 3 vol % carbon tetrachloride is injected subcutaneously. At 24 hours after this time blood is collected from orbital plexus, and then serum is prepared. The serum is diluted, and then GOT and GPT values are measured. The agent activating an EGF receptor obtained by the present invention suppresses increases in GOT and GPT values.

EXPERIMENT EXAMPLE 3

Action on Gastric Ulcer Model Rat

SD male rats are fasted for 24 hours before the start of the experiment, and then incised along a median line under anesthesia so as to cut open each stomach thereof. The outside and the inside of each stomach wall are caught with tweezers with a ring, and then 60 vol % acetic acid is added dropwise to the inside. After a given time period, the tweezers are removed, and then the cut stomach is sutured. The rats are then fed ad libitum. On the next day, administration of a test substance is begun, and changes in the thickness of the mucosal layer are measured with time. The agent activating an EGF receptor obtained by the present invention increases the thickness of the mucosal layer.

EXPERIMENT EXAMPLE 4

Action on Granulation

Paper discs allowed to absorb a test substance are transplanted subcutaneously to the dorsal regions of Wistar male rats under anesthesia. Changes in dry weight, protein content, DNA content and/or hydroxyproline content of the thus formed granulation tissues are measured with time. The agent activating an EGF receptor obtained by the present invention increases the dry weight, the protein content, the DNA content and/or the hydroxyproline content.

EXPERIMENT EXAMPLE 5

Action on Parkinson Disease Model Rat

Parkinson disease model rats are produced by administering 6-hydroxydopamine HBr to the nigrostriatal dopamine pathway (on one side) of each SD female rat. The ventral midbrain obtained from a 14-week-old rat fetus and a test substance are transplanted into the striatum, amphetamine is administered, and then changes in mobility are observed with time. The agent activating an EGF receptor obtained by the present invention decreases mobility when amphetamine is administered.

Moreover, the biological activity of the agent inhibiting the activation of EGF receptor can be confirmed by, for example, various methods shown below.

EXPERIMENT EXAMPLE 6

Action on Tumor Transplantation Model Mouse

This experiment is conducted by procedures similar to those in the experiment example 1, except that EGF is administered together with a test substance, and biological activity of this group is compared with that of a group to which only EGF has been administered. The agent inhibiting the activation of EGF obtained by the present invention inhibits changes in carcinoma weight that are observed when only EGF has been administered.

EXPERIMENT EXAMPLE 7

Action on Rat Subjected to Oophorectomy

After ovaries have been resected from SD female rats, a test substance is administered. After a given time period, both femora are resected, and calcium and hydroxyproline levels contained in bone trabeculae are measured. The agent inhibiting the activation of EGF receptor obtained by the present invention suppresses decreases in calcium and hydroxyproline contents.

Furthermore, the biological activity of an EGF-receptor-selective-drug delivery agent can be confirmed by, for example, the following method.

EXPERIMENT EXAMPLE 8

Action on Tumor Transplantation Model Mouse

This experiment is conducted by procedures similar to those in the experiment example 1, except that an appropriate cytotoxic substance is administered together with a test substance, and then biological activity of this group is compared with that of a group to which only the cytotoxic substance has been administered. The EGF-receptor-selective drug delivery agent obtained by the present invention enhances the action suppressing an increase in carcinoma weight that is observed when only the cytotoxic substance has been administered.

The physiological activity and the pharmacological activity of EGF have been reported as follows.

1) Promotion [Dev Biol., 12, 394 (1965), Science, 201, 515 (1978)] or suppression [J. Biol. Chem., 259, 7761 (1984)] of the proliferation of normal cells and tumor cells
2) Promotion of self-regeneration of damaged organs [Ciba Found Symp., 55, 95 (1977)]
3) Action suppressing gastric acid secretion [Gut, 23, 951 (1982)]•Action protecting mucous membrane of digestive tract [J. Clin. Gastroenterol., 13, S103 (1991)]
4) Action promoting wound healing [J. Surg. Res., 33, 164 (1982)]•Action correcting cornea [Exp. Eye Res., 40, 47 (1985)]
5) Action protecting nerves [J. Neurosurg. Sci., 37, 1 (1993)]•Action differentiating/proliferating neurons [J. Neurosci., 12, 4565 (1992), J. Neurosci., 16, 2649 (1996)]
6) Action promoting calcium liberation [Endocrinology, 107, 270 (1980)]

A substance (agonist) binding to an EGF receptor so as to activate the receptor can be used as 1) an agent for regulating the proliferation of tumor cells and preferably an anti-tumor agent, or an agent promoting the activation or the metabolism of cells, cosmetics, and preferably a depilatory; 2) an agent promoting the regeneration of damaged organs and preferably a therapeutic agent against liver function failure; 3) an agent used against digestive tract dysfunction and preferably an agent suppressing gastric acid secretion, an agent protecting the mucous membranes of digestive tracts, and an antiulcer agent; 4) an agent promoting wound healing, and preferably a therapeutic agent for skin ulcer or damaged cornea due to diabetes mellitus, injury, burn, or the like; and 5) an agent regenerating or protecting neurons and preferably an anti-parkinsonism agent.

Furthermore, a substance (antagonist) binding to an EGF receptor, so as to inhibit the receptor activation can be used as: 1) an agent regulating the proliferation of normal cells and tumor cells, and preferably an anti-tumor agent, a therapeutic agent for psoriasis, and a therapeutic agent for chronic obstructive respiratory disease including asthma; and 2) an agent suppressing bone resorption, and preferably a prophylactic or a therapeutic agent for osteoporosis.

Furthermore, a compound binding to an EGF receptor can be used as an agent for selectively delivering a drug to cells having the EGF receptor and preferably an agent for selectively delivering a cytotoxic substance as a drug to tumor cells.

The present invention also provides a substance regulating EGFR activity that is identified or designed by the above-described method for designing or screening for a substance regulating EGFR activity using the structure coordinates of the EGF-EGFR complex, or the method for designing or screening for a substance regulating EGFR activity using a pharmacophore.

3-6 EGFR Agonist or EGFR Antagonist

The present invention also provides an EGFR agonist or an EGFR antagonist having a structure that fits a pharmacophore defined by specific spheres representing pharmacophoric features. "Having a structure that fits a pharmacophore" means that the structure coordinates obtained when the three-dimensional structure of an EGFR agonist or an EGFR antagonist is generated match the relative arrangement and features of at least 3 spheres representing pharmacophoric features. Examples of atoms or functional groups that fit each sphere representing pharmacophoric features are defined in a manual attached to a program such as Catalyst™ (Accelrys Inc., San Diego, Calif., Catalyst Documentation Release 4.5, 1999). An example of a pharmacophore having specific spheres representing pharmacophoric features is disclosed in Examples 5 and 6, but is not limited thereto. Pharmacophores obtained by the method for designing a pharmacophore of the present invention are also included herein.

3-7 Method for Regulating EGFR Activity

The present invention also provides a method for regulating EGFR activity, which comprises bringing EGFR into contact with a substance regulating EGFR activity that has a structure that fits a pharmacophore defined by specific spheres representing pharmacophoric features. This method may further comprise a step of confirming that EGFR activity has been regulated. The step of confirming that EGFR activity has been regulated can be realized by detecting that at least one phenomenon (e.g., phosphorylation of EGFR intracellular domains and cell proliferation) known to take place as a result of EGFR activation has been inhibited or promoted.

4. Production of EGF Variant and EGFR Variant Using Structure Information

The present invention provides a method for designing an EGFR variant, or a method for designing an EGF variant, which uses structure coordinates of an EGF-EGFR complex. The present invention further provides a method for producing an EGFR variant or an EGF variant using the design method and the EGFR variant or the EGF variant obtainable by the production method.

The interaction sites and the dimerization sites among EGF/EGFR are observed using the structure coordinates of the EGF-EGFR complex of the present invention, so that point mutation can be introduced depending on the purpose into an amino acid residue in EGF or EGFR. The method for designing an EGFR variant or the method for designing an EGF variant, which use the structure coordinates of the EGF-EGFR complex, can comprise the following steps of: entering the structure coordinates of the EGF-EGFR complex into a computer; specifying amino acid residues composing EGF-EGFR binding sites or EGFR dimerization sites by analyzing the structure of the EGF-EGFR complex; and specifying amino acid residues to which mutation is introduced.

Furthermore, the method may also comprise a step of displaying visually the three-dimensional structure of the EGF-EGFR complex on a computer. The step of specifying amino acid residues composing EGF-EGFR binding sites or EGFR dimerization sites by analyzing the structure of the EGF-EGFR complex and the step of specifying amino acid residues to which mutation is introduced can be realized by visual observation and/or analysis using a computer program.

The method for producing an EGFR variant or an EGF variant using the design method can comprise the following steps of: designing an EGFR variant or an EGF variant using the structure coordinates of the EGF-EGFR complex; preparing a variant protein; and subjecting the variant protein to biochemical assay so as to confirm that the protein has desired activity.

For example, the method makes it possible to design an EGF variant having enhanced EGF activity. Compared with a simple recombinant EGF, such an EGF variant has merit in that it can be administered in low doses as a medicament for injury or the like.

Specifically, to design an EGF variant having activity as an agonist (agent), mutation is introduced into amino acid residues and the region adjacent thereto of EGF participating in direct interaction with EGFR so as to be able to bind more strongly with an amino acid residue in the region on the EGFR side corresponding upon interaction. Here, "the region adjacent thereto" means a region participating in electrostatic interaction, hydrophobic interaction, Van der Waals interaction, hydrogen bond formation, or the like with the amino acid residue, and specifically a region that is located within 5 Å from the amino acid residue. Furthermore, when a variant EGF having activity as an agonist is designed by introducing mutation into a site other than the above regions, such a design method is also encompassed in the scope of the present invention, as long as it uses the structure coordinates of the present invention.

The step of entering the structure coordinates of the EGF-EGFR complex into a computer, the step of visually displaying the three-dimensional structure of the EGF-EGFR complex on the computer, and the step of specifying amino acid residues composing EGF-EGFR binding sites or EGFR dimerization sites by analyzing the structure of the EGF-EGFR complex are described in detail in "3-1" above. In the step of specifying amino acid residues into which mutation is introduced, examples of interaction by noncovalent bonds that should be considered include electrostatic interaction, hydrophobic interaction, Van der Waals interaction, and hydrogen bond formation. By comprehensively considering them, a final variant can be designed. For example, in the vicinity of amino acid residues having negatively charged side chain portions, such as glutamic acid and aspartic acid on the EGFR side, mutation is introduced so that positively-charged side chains of amino acid residues such as lysine, arginine, and histidine are arranged as amino acid residues of EGF adjacent thereto. Conversely, in the vicinity of amino acid residues having positively charged side chain portions, such as lysine, arginine, and histidine, mutation is introduced so that negatively-charged side chains of amino acid residues such as glutamic acid and aspartic acid are arranged as amino acid residues of EGF adjacent thereto. Moreover, for a portion where amino acid residues whose side chain portions have high hydrophobicity (e.g., alanine, leucine, isoleucine, valine, proline, phenylalanine, triptophan, and methionine) mainly cluster together for interaction, positions at which hydrophilic amino acid residues such as serine, threonine, tyrosine, asparagine, and glutamine, or charged amino acid residues such as aspartic acid, glutamic acid, lysine, arginine, and histidine, are present in EGF are found, the amino acid residues are substituted with hydrophobic amino acid residues, thereby enhancing hydrophobic interaction. Furthermore, for the main chain portion that forms hydrogen bonds, or side chain portions of amino acid residues such as serine and tyrosine, amino acid residues corresponding thereto are caused to mutate so as to be able to form new hydrogen bonds. In the above mutation, care should be exercised so that Van der Waals interactions become as large as possible at the side chain and the main chain of amino acid residues, and steric constraints are prevented from being generated between atoms. Moreover, it is necessary to prevent any new gap portions from being generated due to mutation. For a region wherein a gap portion is already present, it is also necessary to consider mutation that fills the gap portion as far as possible. In this manner, electrostatic interaction, hydrophobic interaction, Van der Waals interaction, hydrogen bond formation, and other factors are comprehensively taken into consideration visually on a computer screen or/and using an appropriate computer program, so that a final variant can be designed.

For example, according to the analytical results of the crystal structure, Met21 of EGF can be substituted with an amino acid residue capable of forming a hydrogen bond having carbons upto or beyond a delta carbon with a certain degree of probability. In particular, substitution of Met21 with Lys, Arg, Glu, or Gln can confer the ability of forming hydrogen bonds between the hydroxyl group of Tyr45 side chain and Leu14 main chain carbonyl of Gln16 side chain. Thus, elevated activity of binding to EGFR, improved EGF physical properties, and the like can be expected. On the contrary, substitution with amino acid side chains extending to only Cγ can deteriorate activity (e.g., Thr and Ser). Furthermore, Gln43 can be substituted with a hydrophobic residue such as Leu and Ile with a certain degree of probability. This can be inferred from the fact that a residue of EGFR capable of conducting interaction is Leu.

Furthermore, to design an EGF variant having activity as an antagonist (antagonistic drug), mutation is introduced into amino acid residues of EGF and the region adjacent thereto participating in direct interaction with EGFR. Next, a variant characterized in that the binding of the variant EGF to EGFR makes it impossible to keep the relative position of the 2 original molecules, EGF and EGFR, in the three-dimensional space; or a variant characterized in that the variant EGF and EGFR become unable to interact with each other so that the variant has activity as an antagonist against native EGF, is selected. Alternatively, a variant that does not cause any structural changes in EGFR while binding to EGFR is also useful. There is a case wherein variant EGF having activity as an antagonist is designed by introducing mutation into a site other than those participating in direct interaction with EGFR, and such a design method is also encompassed in the scope of the present invention as long as it uses the structure coordinates according to the present invention.

Moreover, introduction of mutation that makes interaction difficult into amino acid residues participating in EGFR dimerization also makes it possible to design a variant EGFR that binds to EGF, but does not perform dimerization. If it is designed as a soluble variant EGFR, the soluble variant EGFR is expected to exert a therapeutic effect against carcinoma, psoriasis, or the like by exerting EGFR antagonist activity in a manner similar to that of an EGF neutralizing antibody. For example, Gln252 is linked by a hydrogen bond to the Ala286 main chain, Tyr246 is linked by a hydrogen bond to the Cys283 main chain, and Asn86 is linked by a hydrogen bond to the Thr249 side chain so as to stabilize the dimer. Substitution of these side chains of amino acid de residues with amino acids that are unable to form hydrogen bonds makes it possible to construct a molecule capable of trapping EGF without carrying out dimerization.

"Variant" means a protein having an amino acid sequence derived from the amino acid sequence of the original protein by substitution, addition, deletion, or modification of at least 1, for example, 1 or several (1 to 10), amino acids. Examples of amino acid modification include, but are not limited to, amidation, carboxylation, sulfation, halogenation, alkylation, glycosylation, phosphorylation, hydroxylation, and acylation (e.g., acetylation). Amino acids to be substituted or added may be native amino acids, non-native amino acids, or amino acid analogues. Native amino acids are preferred. "Native amino acids" mean L-isomers of native amino acids. Examples of native amino acids include glycine, alanine, valine, leucine, isoleucine, serine, methionine, threonine, phenylalanine, tyrosine, triptophan, cysteine, proline, histidine, aspartic acid, asparagine, glutamic acid, glutamine, γ-carboxyglutamic acid, arginine, ornithine, and lysine. Unless specified, all amino acids in this specification are L-amino acids. "Non-native amino acids," mean amino acids in a protein that are not generally found in the nature. Examples of non-native amino acids include norleucine, para-nitrophenylalanine, homophenylalanine, para-fluorophenylalanine, 3-amino-2-benzil propionic acid, D- or L-homoarginine, and D-phenylalanine. "Amino acid analogue" means molecules that are not amino acids, but are analogous to amino acids in physical properties and/or functions. Examples of an amino acid analogue include ethionine, canavanine, and 2-methyl glutamine.

Structure coordinates to be used in the method for designing a variant of the present invention may be the structure coordinates shown in Table 1 or Table 2, structure coordinates of a structure homologue newly produced by calculation or the like using a computer based on those shown in Table 1 or Table 2, or some of the structure coordinates extracted from these structure coordinates. In the case of designing a medicament for humans, the use of structure coordinates of a human-derived protein is further preferred.

A variant designed according to the present invention can be prepared by many methods. For example, based on the present invention, DNA encoding a variant designed based on the present invention can be obtained by chemically synthesizing an oligonucleotide corresponding to a variant, substituting a site of the oligonucleotide encoding corresponding amino acid residues (which has been determined so that mutation is effective therefor) with a native oligonucleotide portion using a sequence-specific oligonucleotide cleavage enzyme (restriction enzyme). The thus obtained variant DNA is incorporated into an appropriate expression vector, the vector is ligated into an appropriate host, and then the recombinant protein thereof is produced by the host, so that the above variant can be obtained.

Furthermore, for a variant designed by the design method of the present invention and prepared, it is preferable to confirm whether or not the variant has desired activity by biochemical assay. An assay system that can be used is not specifically limited, and the previously described (3-5) biochemical assay example can be employed. Specifically, an amino acid residue into which mutation should be introduced is determined utilizing the structure coordinates of the present invention, producing a variant protein using gene engineering techniques, subjecting the variant protein to biochemical assay, and then evaluating whether or not the variant protein has desired activity. Specific examples of desired activity of EGF include EGFR-binding ability and/or ability to enhance or attenuate EGFR dimerization-inducing ability. Specific examples of desired activity of EGFR include EGF-binding ability and/or ability to enhance or attenuate dimerization ability.

As described above, the use of the structure coordinates of the present invention makes it possible to produce a variant based on theoretical analysis within a three-dimensional space, which has been conducted on a trial and error basis under conditions lacking theoretical support for the three-dimensional structure.

In the method for designing an EGF variant or an EGFR variant using the structure coordinates of the EGF-EGFR complex of the present invention, structure coordinates described in section "2. Structure coordinates of EGF-EGFR complex" can be used as structure coordinates. Moreover, by the use of structure coordinates of a ligand-receptor complex obtained using the structure coordinates of the EGF-EGFR complex by a homology modeling method or a molecular replacement method described below, a variant of the ligand or a variant of the receptor can be designed by a similar method.

The present invention provides a variant that is obtainable by the above method for designing and that for producing an EGF variant or an EGFR variant.

Furthermore, the present invention provides the following variants (A) to (D) as specific examples of a variant:

(A) an EGFR variant having amino acid mutation at an EGFR dimerization site;
(B) an EGFR variant having amino acid mutation at an EGF-EGFR binding site;
(C) an EGFR variant having amino acid mutation at an EGFR dimerization site and an EGF-EGFR binding site;
(D) an EGF variant having amino acid mutation at an EGF-EGFR binding site.

Preferred embodiments of (A) include the following (A-1) to (A-3):
(A-1) an EGFR variant having mutation in at least one amino acid residue among amino acid residues composing an EGFR dimerization site;
(A-2) an EGFR variant having mutation in at least one amino acid residue among amino acid residues composing an EGFR dimerization site, and having attenuated EGFR dimerization activity; and
(A-3) an EGFR variant having mutation in at least one amino acid residue among amino acid residues composing an EGFR dimerization site, and having enhanced EGFR dimerization activity;

Preferred embodiments of (B) include the following (B-1) to (B-3):
(B-1) an EGFR variant having mutation in at least one amino acid residue among amino acid residues composing an EGF-EGFR binding site;
(B-2) an EGFR variant having mutation in at least one amino acid residue among amino acid residues composing an EGF-EGFR binding site, and having attenuated EGF-binding activity; and
(B-3) an EGFR variant having mutation in at least one amino acid residue among amino acid residues composing an EGF-EGFR binding site, and having enhanced EGF-binding activity.

Preferred embodiments of (C) includes the following (C-1) to (C-2):
(C-1) an EGFR variant having mutation in at least one amino acid residue among amino acid residues composing an EGFR dimerization site and in at least one amino acid residue among amino acid residues composing an EGF-EGFR-binding site;
(C-2) an EGFR variant having mutation in at least one amino acid residue among amino acid residues composing an EGFR dimerization site and in at least one amino acid residue among amino acid residues composing an EGF-EGFR-binding site, and having enhanced EGF-binding activity and attenuated EGFR-dimerization activity.

As shown in Example 9, EGF and EGFR are thought to carry out EGF-EGFR binding and EGFR dimerization by so-called "induced fit." Hence, a variant having mutation at an EGFR dimerization site can generate a change in EGF-binding ability, and an EGFR variant having mutation at an EGF-EGFR-binding site can generate a change in EGFR dimerization ability. Therefore, possible examples of EGFR variants, in addition to the above EGFR variants, have desired activity of any one of enhanced EGF-binding activity, attenuated EGF-binding activity, enhanced EGFR dimerization activity, attenuated EGFR dimerization activity, enhanced EGF-binding activity and enhanced EGFR dimerization activity, attenuated EGF-binding activity and attenuated EGFR dimerization activity, enhanced EGF-binding activity and attenuated EGFR dimerization activity, and attenuated EGF-binding activity and enhanced EGFR dimerization activity.

Preferred embodiments of (D) include the following (D-1) to (D-3):
(D-1) an EGF variant having mutation in at least one amino acid residue among amino acid residues composing an EGF-EGFR binding site;
(D-2) an EGF variant having mutation in at least one amino acid residue among amino acid residues composing an EGF-EGFR binding site, and having attenuated EGFR-binding activity;
(D-3) an EGF variant having mutation in at least one amino acid residue among amino acid residues composing an EGF-EGFR binding site, and having enhanced EGFR-binding activity.

Amino acid residues composing an EGFR dimerization site and amino acid residues composing an EGF-EGFR binding site of a variant in this section are defined according to the explanation given in section "2. Structure coordinates of EGF-EGFR complex." "Composing a dimerization site" can also entail the formation of important interactions in dimerization. This also applies in the case of an EGF-EGFR binding site.

"Attenuated activity" means that the activity of a protein having mutation is, for example, 0.8 times or less, preferably 0.5 times or less, and further preferably 0.3 times or less than the activity of a protein having a native amino acid sequence that contains no mutation. "Enhanced activity" means that the activity of a protein having mutation is, for example, 1.2 times or more, preferably 1.5 times or more, and further preferably 2.0 times or more than the activity of a protein having a native amino acid sequence that contains no mutation. Protein activity can be assayed using any method that persons skilled in the art can generally employ. Examples of such assay include biochemical assay explained in section "3-5" of "3. Method for screening or designing using structure coordinates," and methods described in Examples 7 to 9.

5. Molecular Replacement Method Using Structure Coordinates of EGP-EGFR Complex The present invention provides a method for obtaining structure coordinates of a protein or a protein complex with an unknown structure by a molecular replacement method, which uses structure coordinates of an EGF-EGFR complex. More specifically, the method can comprise the steps of: crystallizing a protein or a protein complex with an unknown structure; generating an X-ray diffraction image from the crystallized protein or the protein complex with the unknown structure; and applying at least some of the structure coordinates described in Table 1 or Table 2 to the X-ray diffraction image so as to generate at least a partial three-dimensional electron density map of the protein or the protein complex with the unknown structure. The molecular replacement method is a means for solving phase problems in X-ray crystal structure analysis. When an X-ray diffraction image of a native crystal (crystal containing no heavy metal atoms) of a protein or a protein complex with an unknown structure has been obtained, by utilization of the structure information on a protein or a protein complex whose structure has already been determined, the method enables rapid determination of structure coordinates of the protein or the protein complex with the unknown structure without using a heavy atom isomorphous replacement method (Blundell, T. L. and Johnson, L. N., (1976) PROTEIN CRYSTALLOGRAPHY, pp. 443-464, Academic Press, New York).

The structure coordinates or some of the structure coordinates of the EGF-EGFR complex according to the present invention can be used in X-ray crystal structure analysis for a crystal containing whole or a portion of EGF and EGFR, a crystal obtained from another protein having an amino acid sequence that shares significant homology with EGF or EGFR, a crystal obtained from another protein that is predicted to be structurally analogous to EGF or EGFR, or the like. When the molecular replacement method is conducted, for example, a program such as CNS™ (Brunger, A. T., et al., "Crystallography & NMR System: A New Software Suite for Macromolecular Structure Determination," ACTA CRYSTALLOGR. D. BIOL. CRYSTALLOGR. 54(Pt. 5):905-921 (1998) (Accelrys, Inc., San Diego, Calif.) or AMORE™ (CCP4 (one of a program group of the Collaborative Computational Project, Number 4; ACTA CRYSTALLOGR. D50, 670-673 (1994)) can be utilized, and other programs may also be used.

Examples of crystals to which the molecular replacement method should be applied using the structure coordinates of the EGF-EGFR complex of the present invention include a crystal containing whole or a portion of EGF and EGFR, a crystal of another protein having an amino acid sequence that shares significant homology with EGF or EGFR, a crystal of another protein predicted to be structurally analogous to EGF or EGFR, a crystal of a complex of a compound (e.g., agonist or antagonist) that binds to EGFR and EGFR, a crystal of a complex of a compound (e.g., antagonist) that binds to EGF and EGF, a crystal of a protein having amino acid residues that share significant homology with those of EGF, and a crystal of a protein having amino acid residues that share significant homology with those of EGFR. The method can also be applied to a crystal of an EGF variant, a crystal of an EGFR variant, and complexes thereof (including a ligand-receptor complex and a protein-compound complex). Here, significant homology generally means that 20% or more, and preferably 30% or more, amino acids are in agreement between amino acid sequences compared. The molecular replacement method can be applied for structural factors actually calculated from an X-ray diffraction image of a target crystal so as to obtain a meaningful solution. Specifically, a method for structurally analyzing a crystal of an unknown substance other than the above substances by the molecular replacement method using all or some of the structure coordinates of the EGF-EGFR complex according to the present invention is encompassed in the scope of the present invention, when a meaningful solution can be obtained by this method.

In the molecular replacement method using the structure coordinates of the EGF-EGFR complex of the present invention, the structure coordinates explained in section "2. Structure coordinates of EGF-EGFR complex" can be used as structure coordinates. In addition, structure coordinates of a protein or a protein complex obtained using the structure coordinates of an EGF-EGFR complex by a homology modeling method described below can also be used.

Structure coordinates of a protein or a protein complex, which are newly obtained by the molecular replacement method of the present invention, are also encompassed in the scope of the present invention.

6. Homology Modeling Method Using Structure Coordinates of EGF-EGFR Complex

The present invention provides a method for obtaining structure coordinates of a protein or a protein complex with an unknown structure by a homology modeling method using structure coordinates of an EGF-EGFR complex.

Homology modeling is a technique of predicting the unknown structure of a protein (target) based on the known structure of a protein (template) having a sequence analogous thereto. In homology modeling, first, an analogous sequence is searched and found from a structure database, and then the sequences are aligned. Next, based on the sequence of the aligned template, the structure of a corresponding portion is selected so as to construct a putative structure.

There are two methods of homology modeling. One is based on fragments, and the other one is based on restraints. The method based on fragments involves modeling by collecting fragments obtained from a protein with a known structure utilizes the average structure of the fragments, and employs other techniques such as loop modeling for portions that are not structurally conserved. The method based on restraints involves modeling to match restraints (e.g., distance between α carbons, and dihedral angles of main chain side chain) representing structural features. Restraints are expressed by evaluation functions so as to conduct minimization. A representative example of a program used in this case is Sali's MODELLER of Rockfeller university, but examples are not limited thereto.

There is a restraint that homology modeling cannot be applied in the absence of approximately 20%, and preferably 30% or more, homology with a known protein. However, compared with other approaches, homology modeling has advantages in that it can be applied to a large protein and in that the more improved the structure database, the more improved the prediction accuracy is, because homology modeling directly utilizes the database content. Selection and alignment of templates have a large effect on accuracy for structure prediction.

The homology modeling method using the structure coordinates of the EGF-EGFR complex according to the present invention comprises some or all of the steps of: preparing an amino acid sequence of a protein with an unknown structure to be modeled and an amino acid sequence of a protein to be used as a template for modeling; aligning both amino acid sequences; generating coordinates of a target protein using the structure information of the template protein as a template; and verifying that there is no theoretical problem in the thus obtained model structure.

It is very useful if the structure of the EGF-EGFR complex having industrially applicable accuracy is revealed, as this enables drug design by the analysis of the information. The crystal structure of the EGF-EGFR complex is not only useful in drug design of an EGFR agonist or an EGFR antagonist. The use of the crystal structure of the complex also enables prediction of three-dimensional structures of all receptors assumed to have the same conformational folds based on the homology with EGFR with high accuracy. Examples of such a receptor in a state of being liganded include an insulin receptor, an insulin-like growth factor-1 receptor, and ErbB2, 3, and 4. Obtainment of the EGF-EGFR co-crystal structure by the present invention has revealed that EGFR brings about a dynamic conformational change as a result of binding with a ligand. The present invention makes it possible to obtain useful information for structure prediction of a protein having EGF/EGFR-like folds, which is far better than the prior art. For example, general homology modeling using the EGFR structure enables prediction with high accuracy of the active conformation upon binding of an insulin receptor to insulin. Moreover, by specifying a site binding with insulin and designing a molecule complementary thereto, a low molecular weight compound having low molecular insulin-like activity can also be presented. An insulin-like compound that can be orally administered has been anxiously desired. The use of this technology enables the provision of information that is far more reasonable than that obtained by searches through a trial-and-error process. Similarly, prediction of the active conformation is enabled for all proteins having EGFR-like folds. Thus, the present invention makes it possible to conduct analyses for the purposes of useful scientific analyses and drug creation (e.g., anticancer agents).

Information and programs required for each of the above steps of comparing information regarding an amino acid sequence of a target protein with that regarding an amino acid sequence of a template protein, specifying a partial sequence composing a domain, generating coordinates of a target protein as a template using the structure information of a template protein, verifying if there are no theoretical problems in the thus obtained model structure, and specifying amino acid residues composing an interaction site can be obtained using a database that is opened to the public or using various commercialized programs. Known protein information necessary for specifying domains is available from public databases, such as the Genbank protein database (Benson, D. A., et al., "GenBank," NUCLEIC ACIDS RES. 30(1):17-20 (2002) or the PDB database Berman, H. M. et. al., NUCLEIC ACIDS RES. 28:235-242 (2000). In addition, for amino acid sequence comparison, BLAST™ (Altschul, S. F., J. MOL. EVOL. 36:290-300 (1993); Altschul, S. F. et al., J. MOL. BIOL. 215:403-10 (1990)), multiple sequence alignment program ClustalW™ (Thompson, J. D., Higgins, D. G., Gibson, T. J., Nucleic Acids Res. 22:4673-4680 (1994)), or any other available programs may be used. For a domain search, the PROSITE database, which is a motif database (Falquet, L., et al., "The PROSITE database, its status in 2002," NUCLEIC ACIDS RES. 30(1):235-238 (2002)), Pfam Sonnhammer, E. L. L., Eddy, S. R. and Durbin, R., Proteins, 28, pp. 405-420 (1997)), or the like can be utilized. Examples of a search program include HMMER™, which is a homology search program using the hidden Markov model (Durbin, R., Eddy, S.R., Krogh, A., Mitchison. G., Biological Sequence Analysis: Probabilistic Models of Protein and Nucleic Acids, Cambridge University Press 1999) and the Transmembrane prediction program tmap using weight matrix (Persson, B, Argos, P., J. MOL. BIOL. 237:182-92 (1994)). Furthermore, as a protein modeling program, FAMS™ (Ogata, K. et. al., J. MOL. GRAPH. MODEL. 18:258-272 (2000)), Modeler™ (Accelrys Inc., San Diego, Calif.), or Homology™ (Accelrys Inc., San Diego, Calif.), and the like can be used. As a protein structure evaluation program, Profiles-3D™ (Accelrys Inc., San Diego, Calif.) can be used. As a graphics display program, InsightII™ (Accelrys Inc., San Diego, Calif.), SYBYL™ (Tripos, Inc. St. Louis, Mo.), or the like can be used. The contents of these databases or the programs may be improved in terms of the nature thereof or new programs and the like can be developed in the future. These databases and the programs can be utilized as long as they have functions necessary for the implementation of the present invention, and the examples are not limited to the above examples.

In the homology modeling method using the structure coordinates of the EGF-EGFR complex of the present invention, as the structure coordinates, those explained in section "2. Structure coordinates of EGF-EGFR complex" can be used. Moreover, structure coordinates of a protein or a protein complex obtained using the structure coordinates of the EGF-EGFR complex by the above molecular replacement method can also be used.

Structure coordinates of a protein or a protein complex that are newly obtained by the homology modeling method of the present invention are also encompassed in the scope of the present invention.

The homology modeling method using the structure coordinates of the EGF-EGFR complex is explained specifically as follows. An amino acid sequence of a receptor having the same folds as those of EGFR, such as a human insulin receptor, an insulin-like growth factor-1 receptor, or ErbB2, 3, or 4, is extracted from an existing amino acid sequence database. This amino acid sequence is aligned with that of EGFR. As a sequence alignment program or a multiple alignment program, FASTA™, BLAST™, ClustalW™ or the like can be used. Next, homology modeling can be conducted according to a standard method using the EGF-EGFR co-crystal structure specified in the present invention or a partial structure thereof as a template and existing package software (e.g., Homology™ (Accelrys Inc.,) and FAMS (KITASATO UNIVERSITY)). Calculation for molecular optimization of an initial structure is conducted using the force field of Discover™, Charm™, Amber™, or the like. After minimization, a putative structure of a receptor having the same folds (thought to have extremely high accuracy) as those of a liganded insulin receptor, insulin-like growth factor-1 receptor, EGFR (e.g., ErbB2, 3, and 4) or the like can be successfully constructed. As an example, a modeling structure of human ErbB2 is shown in FIG. 12. Amino acid residues important for binding with a ligand have been determined based on the thus obtained modeling structure of each protein, and are presented in FIG. 11. These structures are useful in pharmacophore extraction of agonists or antagonists, computer screening, molecular design of agonists or antagonists (e.g., increased activity and provision of selectivity), design of industrially useful altered proteins, production of neutralizing antibodies and agonist antibodies, novel crystal structure analysis by the molecular replacement method, analysis of other variants, and the like. The thus specified pharmacophores can be utilized for screening for or development of drugs.

In addition, a binding model of a hit compound selected by screening or a derivative thereof may be built and then used for optimization of induction of the obtained compound.

7. Method for Designing Epitope Using Structure Coordinates of EGF-EGFR Complex and Antibody Production Through the use of the structure coordinates of the EGF-EGFR complex of the present invention, an epitope for an antibody can be reasonably designed. This enables efficient and reasonable production of neutralizing antibodies and agonist antibodies. For example, observation of the structure of the complex of the present invention has revealed that Cys33-Trp49 (CVVGYIGERCQYRDLKW: SEQ ID NO: 10) of EGF is a very useful sequence for production of a human EGF neutralizing antibody. It has also revealed that Ser11-Asn32 (SNKLTQLGTFEDHFLSLQRMFN: SEQ ID NO: 11) in domain I, Pro241-Thr266 (PPLMLYNPTTYQMDVNPEGKYSFGAT: SEQ ID NO: 12) in domain II, and Leu345-Leu363 (LHILPVAFRGDSFTHTPPL: SEQ ID NO: 13) in domain III of EGFR are very useful in production of a neutralizing antibody or an agonist antibody.

The method for designing an epitope, which uses the structure coordinates of the EGF-EGFR complex, can comprise the following steps of: entering the structure coordinates of the EGF-EGFR complex into a computer; and specifying a portion that can be used as an epitope by analyzing the structure of the EGF-EGFR complex. The method may further comprise a step of visually displaying the three-dimensional structure of the EGF-EGFR complex on the computer. The step of specifying a portion that can be used as an epitope by analyzing the structure of the EGF-EGFR complex can be implemented by visual observation and/or analysis using a computer program. Furthermore, the method for producing an anti-EGFR antibody or an anti-EGF antibody using the design method can comprise the following steps of: designing an epitope using the structure coordinates of the EGF-EGFR complex; preparing an antigen containing the designed epitope; and preparing an antibody that recognizes the designed epitope.

To design an epitope, the structure coordinates of the EGF-EGFR complex of the present invention are introduced into a computer program that can graphically display molecular three-dimensional structures. The three-dimensional structure of the EGF-EGFR complex is visually observed, or an appropriate computer program is used, so that a portion that can be used as an epitope is specified. As a portion that can be used as an epitope, a portion being exposed on a molecular surface, or a portion that can come into contact with a solvent (e.g., water molecule) is preferred. Moreover, when a portion that creates a protein-protein interaction site upon the formation of a complex and is exposed on the molecular surface upon the formation of a monomer, or a portion that can come into contact with a solvent (e.g., water molecule) is used as an epitope, a neutralizing antibody that obstructs the formation of a complex can be designed. In the mean time, an antibody that links ligand-receptor binding sites or an antibody that links dimerization sites is inferred to function as an agonist antibody. Furthermore, to design an antibody having neither agonist activity nor neutralizing activity, an epitope having no effect on EGF-EGFR binding and dimerization can also be designed.

After the portion that can be used as an epitope is specified, a peptide having an amino acid sequence of the epitope is synthesized, and then an antibody is produced according to a standard method using the peptide as an antigen. Alternatively, after antibodies are produced using a whole or a portion of a protein as an antigen, an antibody recognizing a desired epitope can be selected and obtained.

An antibody may be a monoclonal antibody or a polyclonal antibody. A monoclonal antibody is preferred because of its high specificity.

The above monoclonal antibody can be prepared by preparing a hybridoma by fusing an antibody-producing cell obtained from an animal immunized with an antigen with a myeloma cell, and then selecting clones producing an antibody that specifically recognizes a desired epitope from the obtained hybridoma.

As a peptide to be used as an antigen for immunization of an animal, a peptide prepared by the recombinant DNA method or chemical synthesis is preferred. Production of a monoclonal antibody is well known in the art. When briefly explained, the preparation involves administering a peptide as an antigen together with an adjuvant to mammals such as mice, rats, horses, monkeys, rabbits, goats, or sheep for immunization. Immunization intervals are not specifically limited, and immunization is conducted at intervals of several days to several weeks. After final immunization, antibody-producing cells (e.g., splenocytes, lymph node cells, and peripheral blood cells) are collected. Next, the antibody-producing cells are fused with myeloma cells. As the myeloma cells to be fused with the antibody-producing cells, an established cell line that is derived from various animals including a mouse, a rat, a human, and the like and is generally available for persons skilled in the art is used. A cell line used herein has drug resistance, is unable to survive in a selection medium (e.g., HAT medium) in an unfused state, and has a property of being capable of surviving only in a fused state. As myeloma cells, various previously known cell lines, for example, P3(P3x63Ag8.653), P3x63Ag8U.1, and the like, can be appropriately used.

Cell fusion is conducted by bringing myeloma cells into contact with antibody-producing cells at a mixing ratio between 1:1 and 1:10 in the presence of a fusion promoter in a medium for culturing animal cells such as MEM, DMEM, or RPMI-1640 media. To promote cell fusion, polyethylene glycol, polyvinyl alcohol, or the like with an average molecular weight between 1,000 and 6,000 can be used. In addition, antibody-producing cells can also be fused with myeloma cells using a commercial cell fuser utilizing electric stimulation.

Hybridomas are selected from cells that had been subjected to cell fusion treatment. An example of such a method is a method utilizing selective growth of cells in a selection medium.

Specifically, a cell suspension is diluted with an appropriate medium, and then inoculated on a microtiter plate. Selection media (e.g., HAT media) are added to each well, and then the cells are cultured while appropriately exchanging the selection media. As a result, cells that have grown can be obtained as hybridomas.

Screening of hybridomas is conducted by a limiting dilution method, a fluorescence excitation cell sorter method, or the like. Finally, monoclonal-antibody-producing hybridomas are obtained. When antibody purification is required for a method for collecting antibodies, antibodies are purified by appropriate selection of or combination of known methods such as an ammonium sulfate precipitation method, ion exchange chromatography, and affinity chromatography.

To evaluate an antibody, it is preferred to evaluate whether or not it has neutralizing activity or agonist activity, in addition to whether or not it specifically recognizes a desired epitope, by biochemical assay. The form of biochemical assay to be employed herein is not limited. For example, the above-described example of biochemical assay can be employed.

The method for designing an epitope of the present invention can also be applied to, in addition to EGF and EGFR, a protein or a protein complex whose structure has been determined by the homology modeling method using the structure coordinates of the EGF-EGFR complex, and a protein or a protein complex whose structure has been determined by the molecular replacement method using the structure coordinates of the EGF-EGFR complex. In addition, an antibody that has been produced utilizing the method for designing an epitope of the present invention is also encompassed in the scope of the present invention.

8. Peptide Fragment

The present invention provides a peptide (polypeptide) or a salt thereof comprising all or some of the amino acid residues of a region forming an EGFR-dimerization site. A region at which EGFR proteins of a complex bind to each other to form a dimer (EGFR dimerization site) consists of, for example, the 240th to the 267th (SEQ ID NO: 14) amino acid residues of an amino acid sequence (amino acid sequence shown in SEQ ID NO: 1) of EGFR, and contains all or some of the amino acid residues of the region.

Furthermore, the present invention also provides a peptide or a salt thereof comprising all or some of the amino acid residues of a region forming a binding site of EGF and EGFR.

Examples of the peptide of the present invention include Cys33-Trp49 of EGF (SEQ ID NO: 10), which is a very useful sequence for producing a human EGF neutralizing antibody, and Ser11-Asn32 in domain I (SEQ ID NO: 11), Pro241-Thr266 in domain II (SEQ ID NO: 12), and Leu345-Leu363 in domain III (SEQ ID NO: 13) of EGFR.

When the peptide of the present invention is chemically synthesized, it can be synthesized by a standard means for peptide synthesis. Examples of such a means include an azide method, an acid chloride method, an acid anhydride method, a mixed acid anhydride method, a DCC method, an active ester method, a method using carboimidazole, and an oxidation-reduction method. In addition, either a solid-phase synthesis or a liquid-phase synthesis can be applied for the synthesis.

Specifically, a peptide is synthesized by condensing amino acids that can compose the peptide of the present invention, and then eliminating protecting groups when a product thereof has protecting groups. Any known techniques may be used as a condensation method or a method for eliminating protecting groups (e.g., Nobuo Izumiya et al., Basis and Experiment for Peptide Synthesis (Peptide go-sei no kiso to jikken), MARUZEN CO., LTD. (1975)). After reaction, the peptide of the present invention can be purified by a combination of general purification methods such as solvent extraction, distillation, column chromatography, liquid chromatography, and recrystallization. Furthermore, in the present invention, the peptide can also be synthesized using a commercial automated peptide synthesizer (e.g., a simultaneous multiple solid-phase peptide synthesizer, PSSM-8, Shimadzu Corporation).

The peptide salt of the present invention is preferably a physiologically acceptable acid addition salt or a basic salt. Examples of an acid addition salt include a salt with an inorganic acid such as hydrochloric acid, phosphoric acid, hydrobromic acid, or sulfuric acid, or a salt with an organic acid such as acetic acid, formic acid, propionic acid, fumaric acid, maleic acid, succinic acid, tartaric acid, citric acid, malic acid, oxalic acid, benzoic acid, methanesulfonic acid, or benzenesulfonic acid. Examples of a basic salt include a salt with an inorganic base such as sodium oxide, potassium hydroxide, ammonium hydroxide, or magnesium hydroxide, or a salt with an organic base such as caffeine, piperidine, trimethylamine, or lysine. Salt can be prepared using an appropriate acid such as hydrochloric acid, or an appropriate base such as sodium hydroxide.

Furthermore, the peptide of the present invention has a C-terminus that is generally a carboxyl (—COOH) group or carboxylate (—COO⁻). The C-terminus may be amide (—CONH$_2$) or ester (—COOR). Here, examples of R in ester include $C_{1-12}$ alkyl, $C_{3-10}$ cycloalkyl, $C_{6-12}$ aryl, and $C_{7-12}$ aralkyl.

Furthermore, the peptide of the present invention also contains an alanine residue on the N-terminus whose amino group is protected with a protecting group, a conjugated peptide such as a glycopeptide having a sugar chain bound thereto, or the like.

BRIEF DESCRIPTION OF DRAWINGS

The patent or application file contains at least one drawing executed in color. Copies of this patent or patent application publication with drawings will be provided by the Office upon request and payment of the necessary fee.

FIG. 1a shows a ribbon diagram oriented with two-fold vertical axis. Most of domain IV is disordered. FIG. 1b shows the top view of FIG. 1a. A two-fold axis is mainly shown. FIG. 1c is a stereo view of a 2Fo-Fc electron density map of a portion of domain I.

FIG. 2a shows the mapping of different interaction sites on the ribbon representation of EGFR and EGF. The three binding sites in the interface are outlined. FIG. 2b is a stereo view of the interface at site 1. Only the side chains of interacting residues are shown. Dotted lines denote hydrogen bonds or salt bridges.

FIG. 3a is a stereo view of the interface at site 2. FIG. 3b is a stereo view of the interface at site 3.

FIG. 4a shows the outline of the binding region in the interface. Only the side chains of interacting residues are shown. FIG. 4b is a stereo view of the interface. Dotted lines denote hydrogen bonds or salt bridges. FIG. 4c is a stereo view of the interface viewed from different direction shown by the arrow in FIG. 4a.

FIG. 5a shows comparison of the overall folding of domain I, II, and III of liganded EGFR with L1, S1, and L2 domains of unliganded IGF-1R. FIG. 5b shows a putative structure of unliganded EGFR in the form of a monomer. Only the side chains of residues that may participate in ligand-dependent activation are shown. FIG. 5c shows the structure of the dimeric EGFR-EGF complex. Only the side chains shown in FIG. 5b are shown.

Figure 1A:
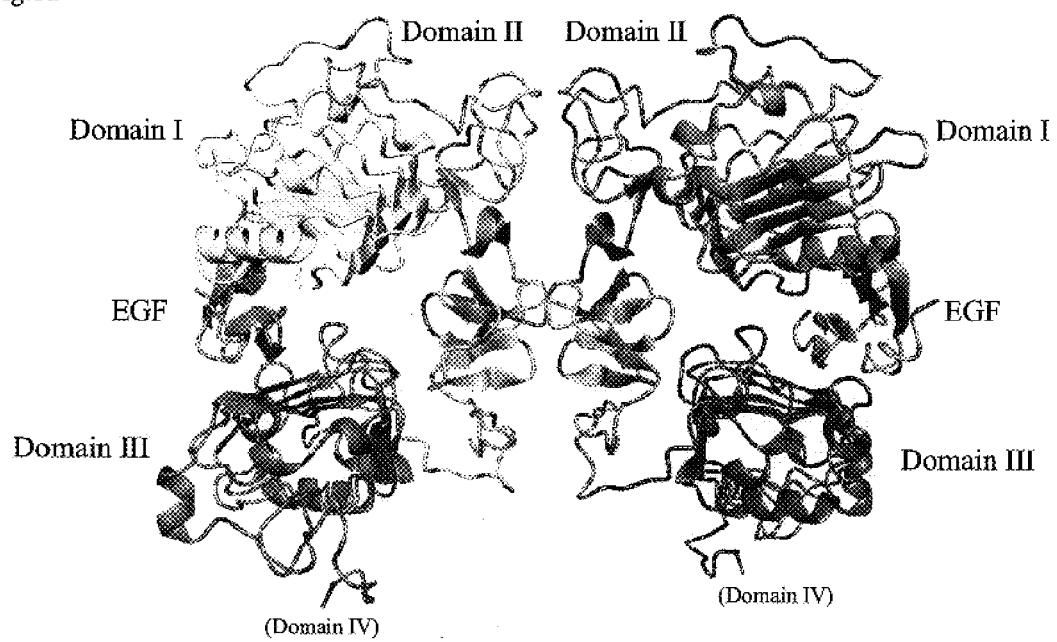
FIG. 1a to 1c show a crystal structure of a dimeric EGFR-EGF complex and a part of an electron density map generated at 3.5 Å resolution.
Figure 1B:
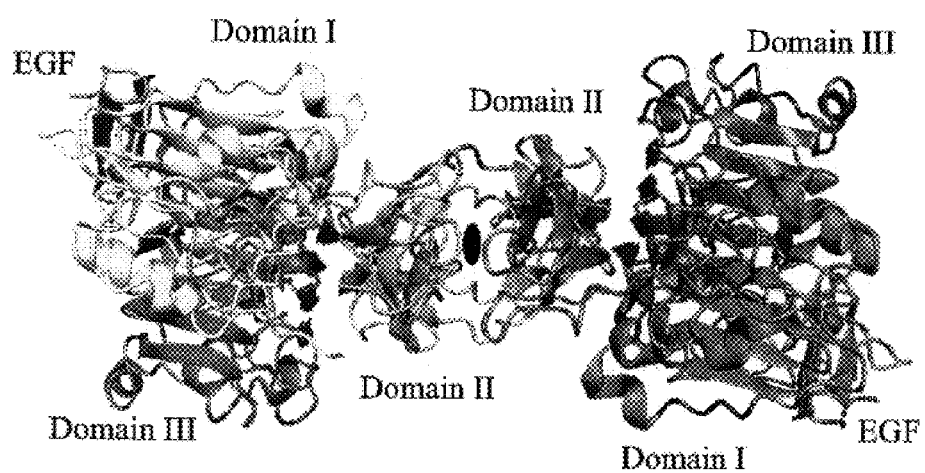
Figure 1C:
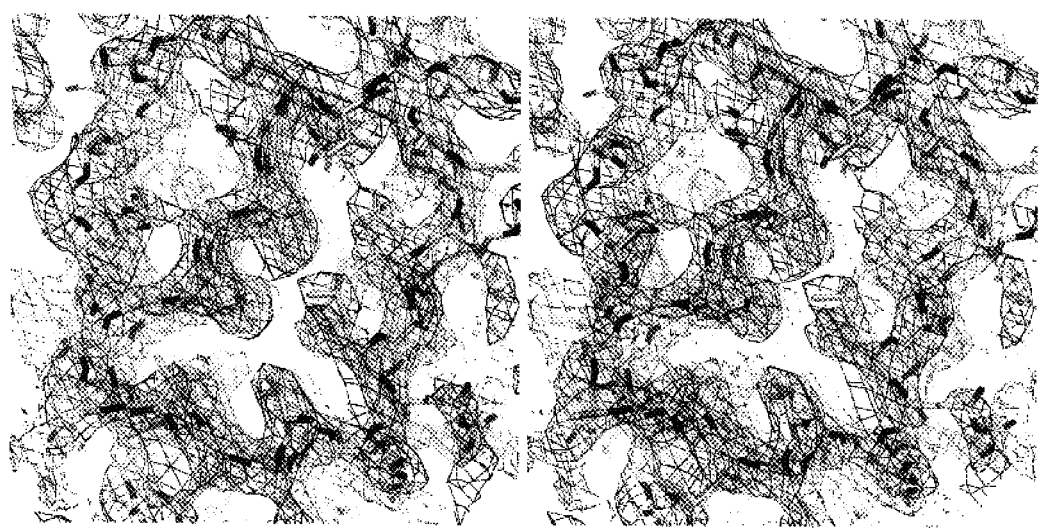
Figure 2A:
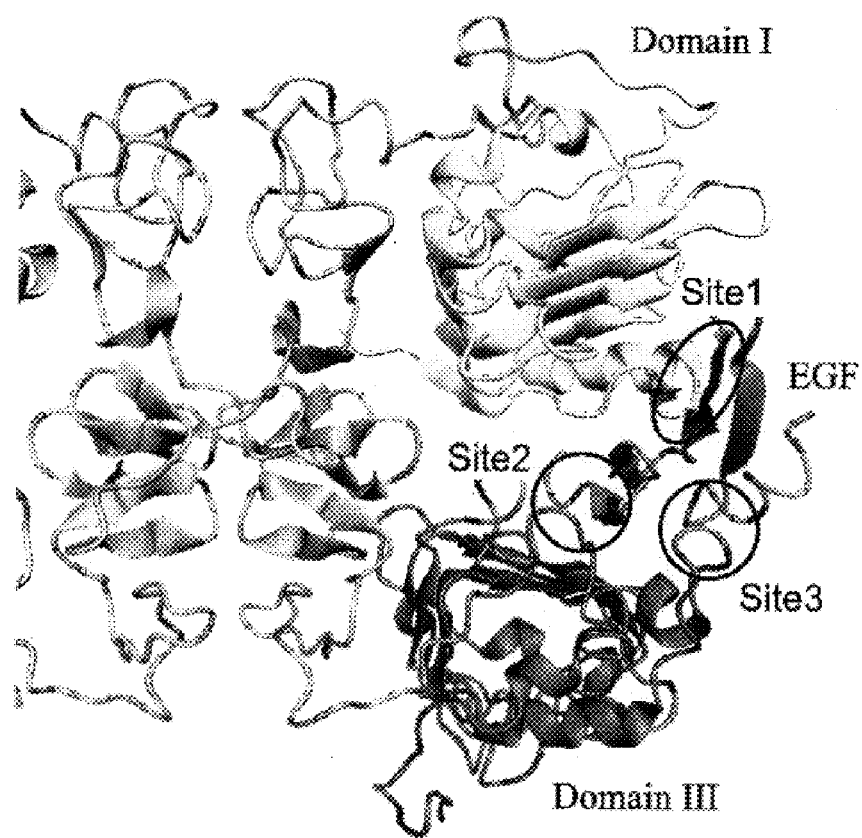
FIG. 2a to 2b show interaction between EGFR and EGF.
Figure 2B:
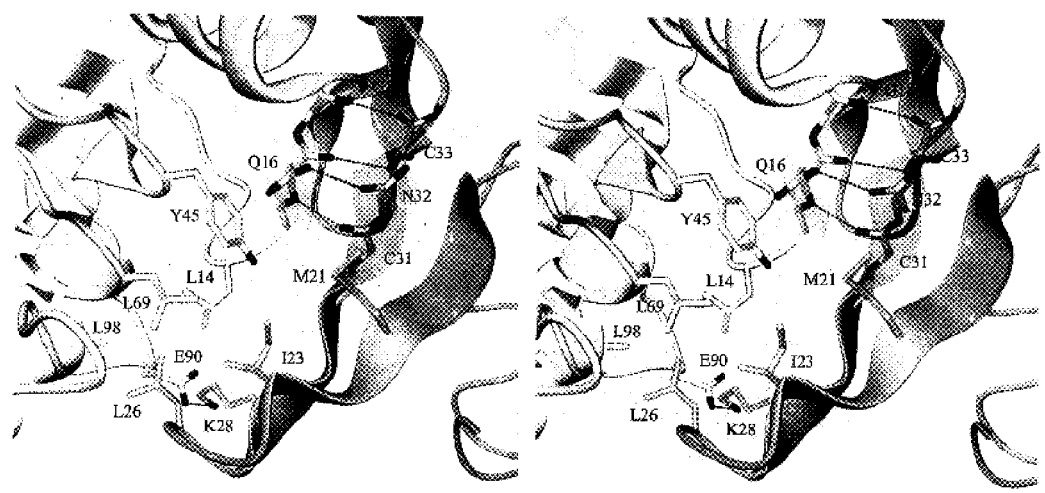
Figure 3A:
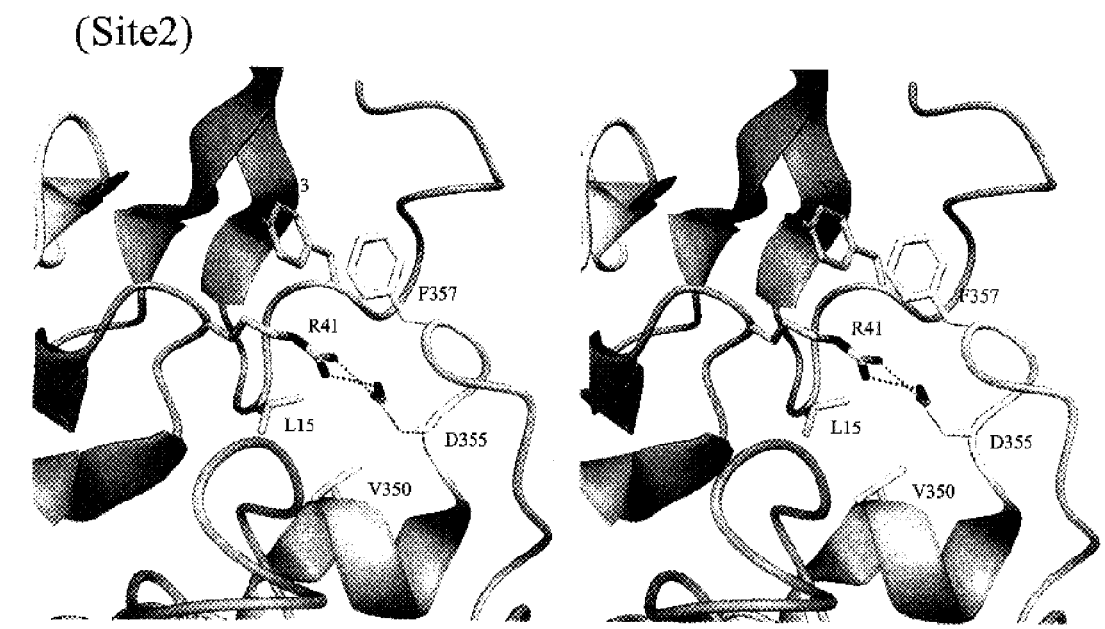
FIGS. 3a and 3b show interaction between EGFR and EGF (continued from FIGS. 2a and 2b).
Figure 3B:
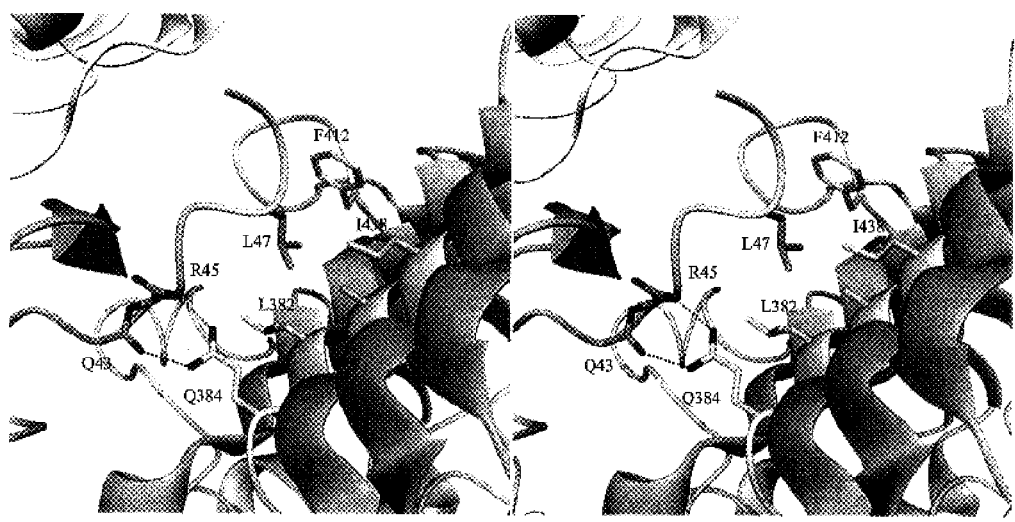
Figure 4A:
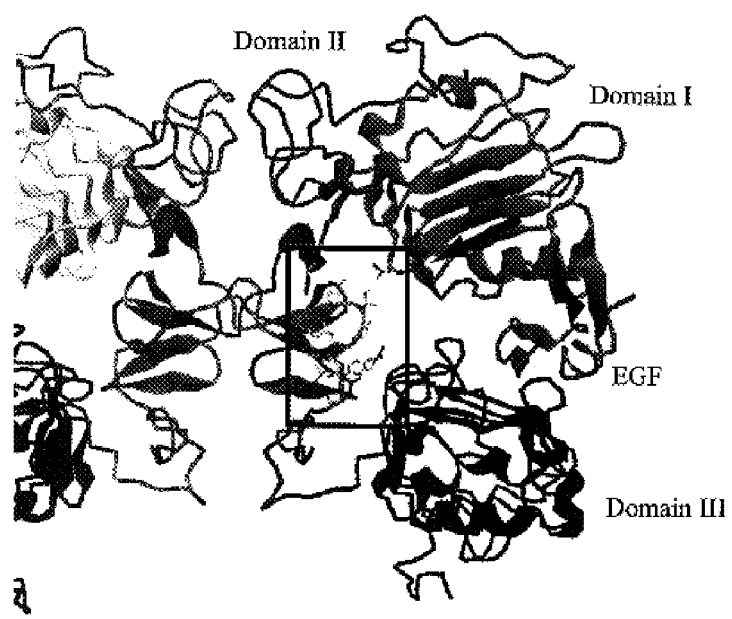
FIG. 4a to 4c show interaction between receptors in dimer interface.
Figure 4B:
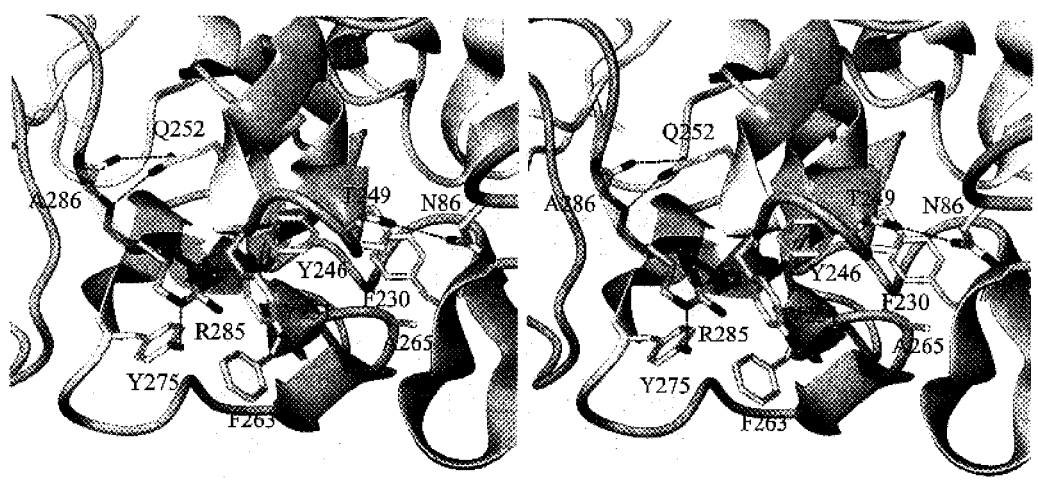
Figure 4C:
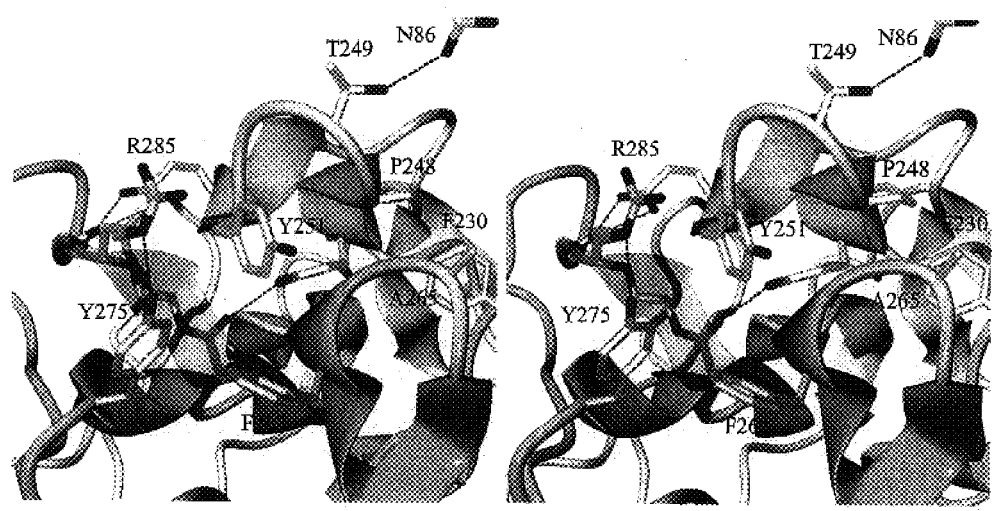
Figure 5A:
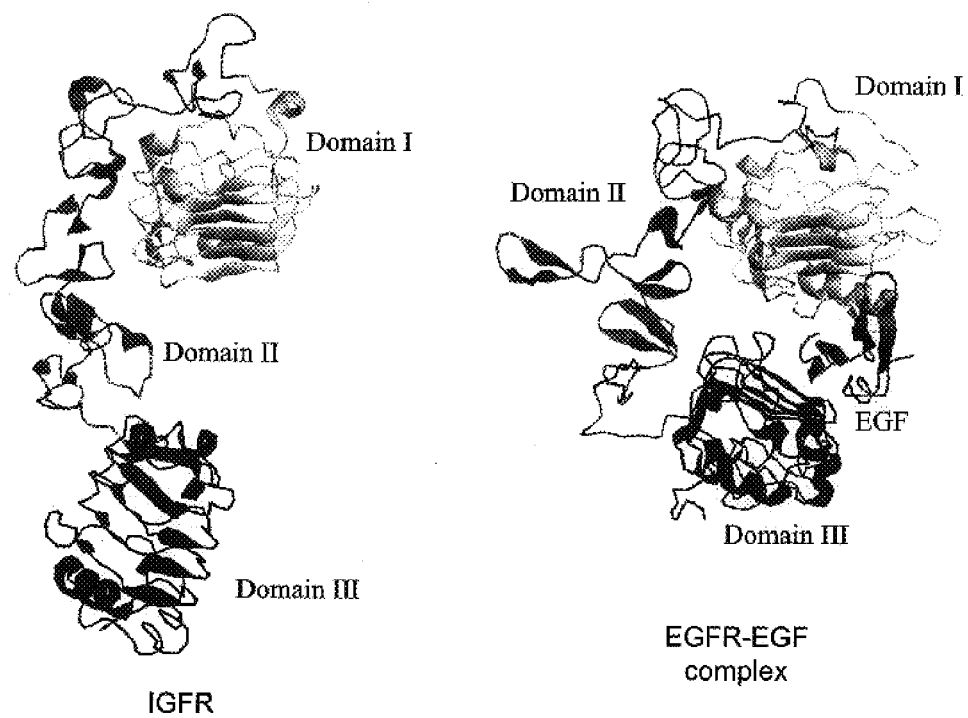
FIG. 5a to 5c shows potential models for EGF-dependent receptor dimerization.
Figure 5B:
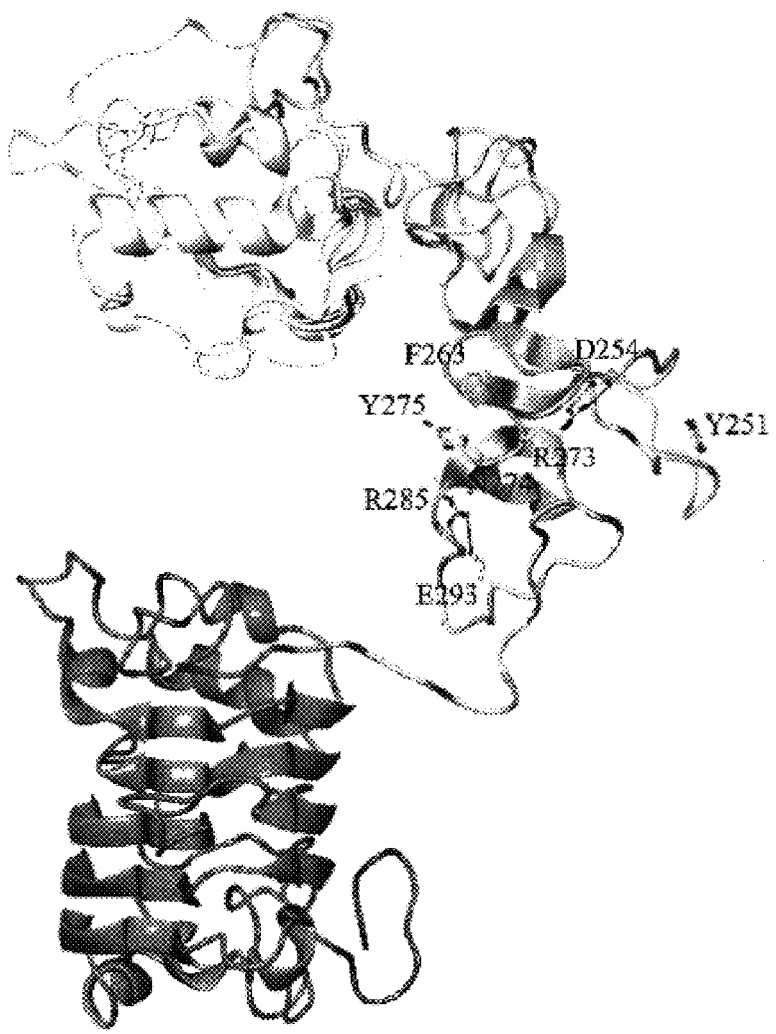
Figure 5C:
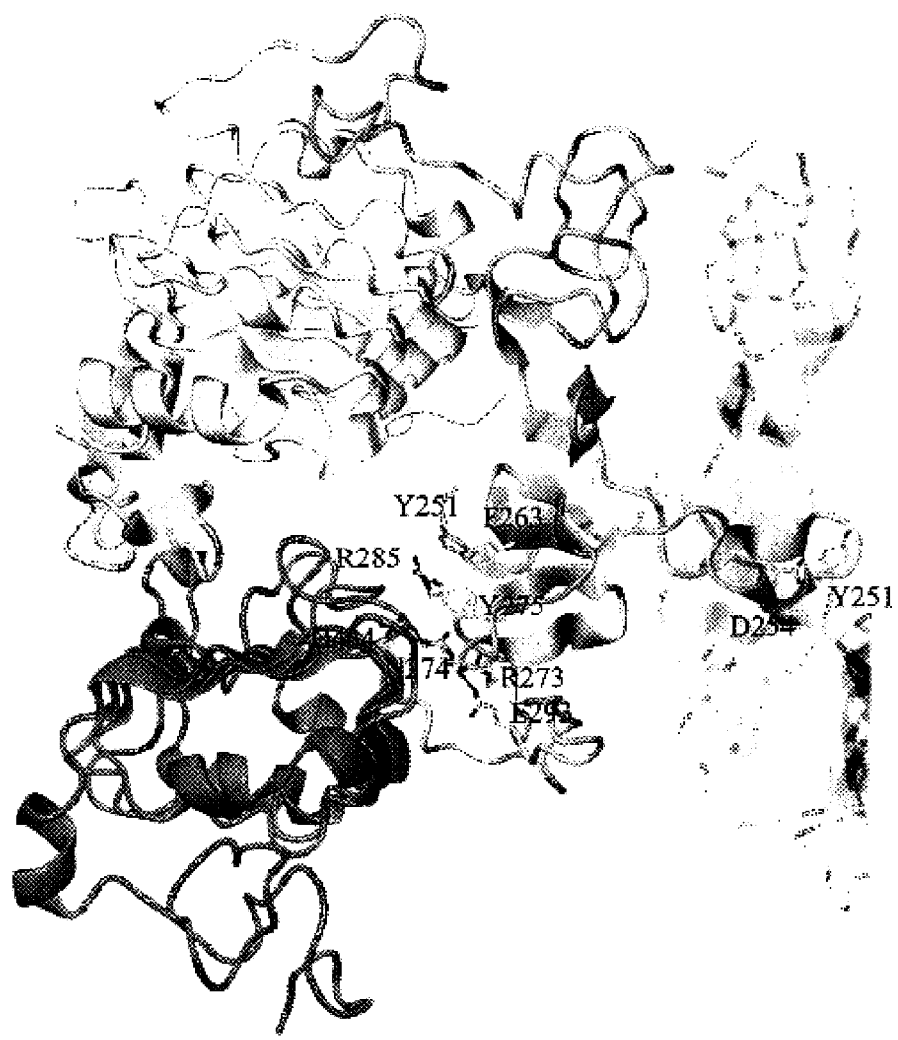

A: Purified dEGFR (2 mg/ml) was incubated at 37° C. together with endoglycosidase H (1 U/ml) and D (0.4 U/ml) in a 0.1M sodium acetate buffer (pH 5.8). After 0 hours (lane 1), 24 hours (lane 2), 48 hours (lane 3), 96 hours (lane 4), and 120 hours (lane 5) of digestion, products were collected, and the digested products were analyzed by 8% SDS-PAGE. In addition, a reaction mixture to which no endoglycosidase had been added (lane 6) or a reaction mixture to which no dEGFR had been added was incubated for 120 hours.

B: Purified dEGFR (0.8 mg/ml) was incubated in a 0.05M Hepes-NaOH buffer (pH 7.5) supplemented with EGF (lane 1) or without EGF (lane 2), followed by incubation with a chemical crosslinking agent BS3 (1 mM).

Figure 7:
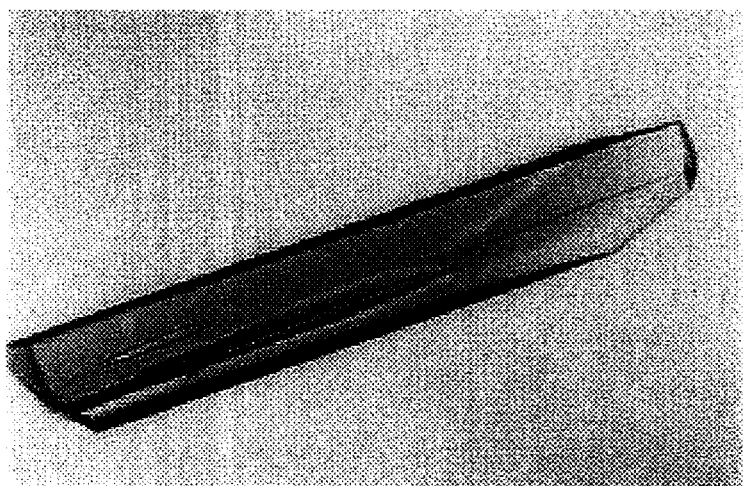

FIG. 7 shows a microphotograph of a dEGFR-EGF complex crystal. The dimension of the crystal is approximately 1.0×0.2×0.2 mm.

Figure 8:
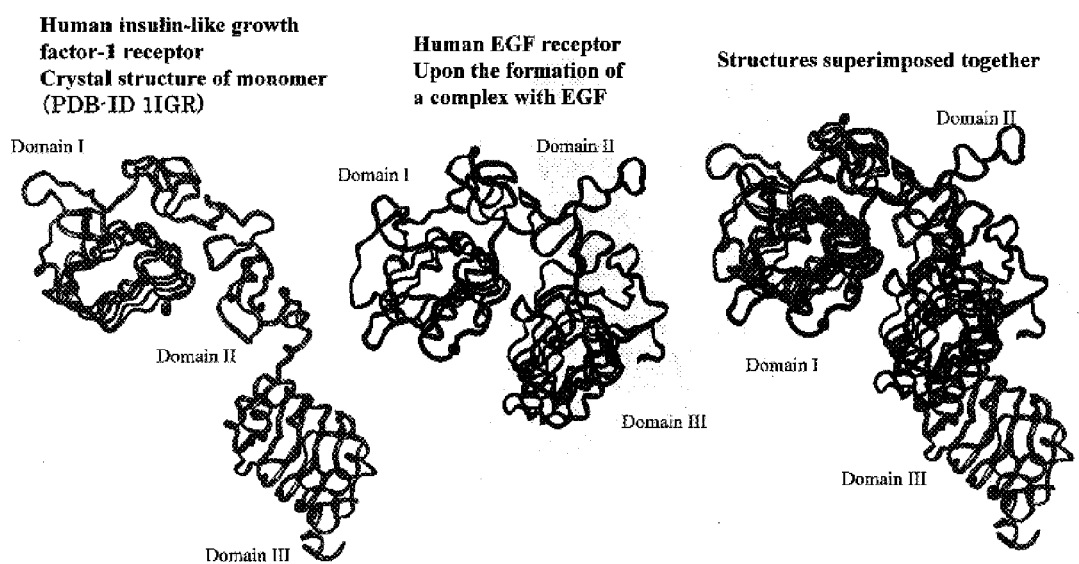

FIG. 8 shows comparison of the three-dimensional structure of a human insulin-like growth factor-1 receptor monomer (PDB-ID: 1 IGR) and that of EGF-bound EGFR.

FIG. 9 shows examples of amino acid residues of EGF-EGFR binding sites that can be utilized for pharmacophore construction.

FIG. 10 shows examples of amino acid residues of EGFR dimerization sites that can be utilized for pharmacophore construction.

FIG. 11 shows ligand-binding sites inferred based on the model structures of ErbB family members and insulin receptor (IR) insulin-like growth factor-1 receptor (IGF-1R) produced by the homology modeling method using the structure coordinates of the EGF-EGFR complex.

Figure 12:
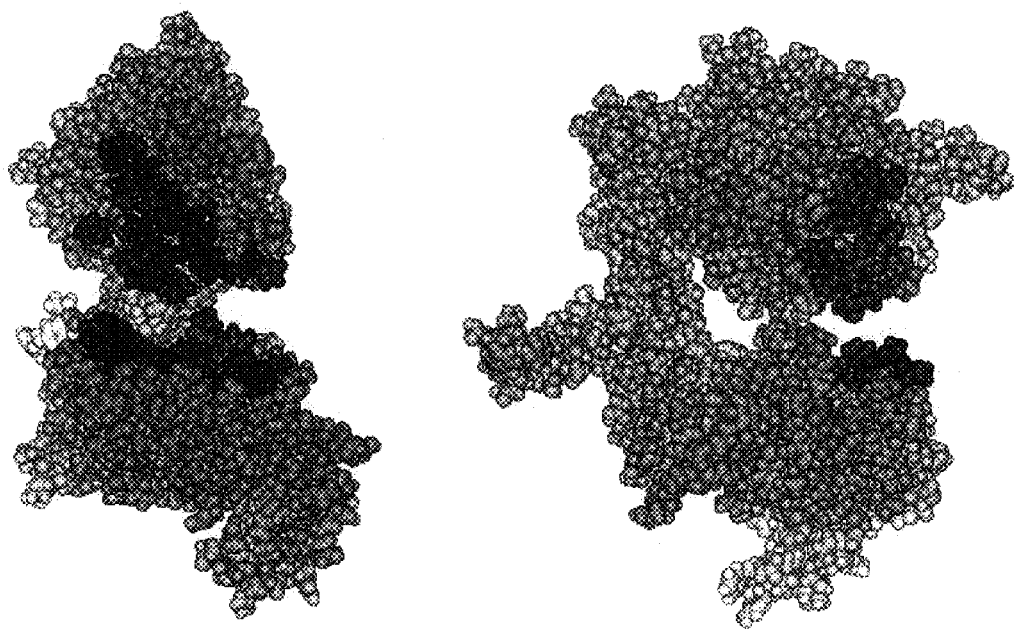

FIG. 12 shows the modeling structure of human ErbB2 produced by the homology modeling method using the structure coordinates of the EGF-EGFR complex. Dark gray portions represent putative ligand-binding sites.

Figure 13:
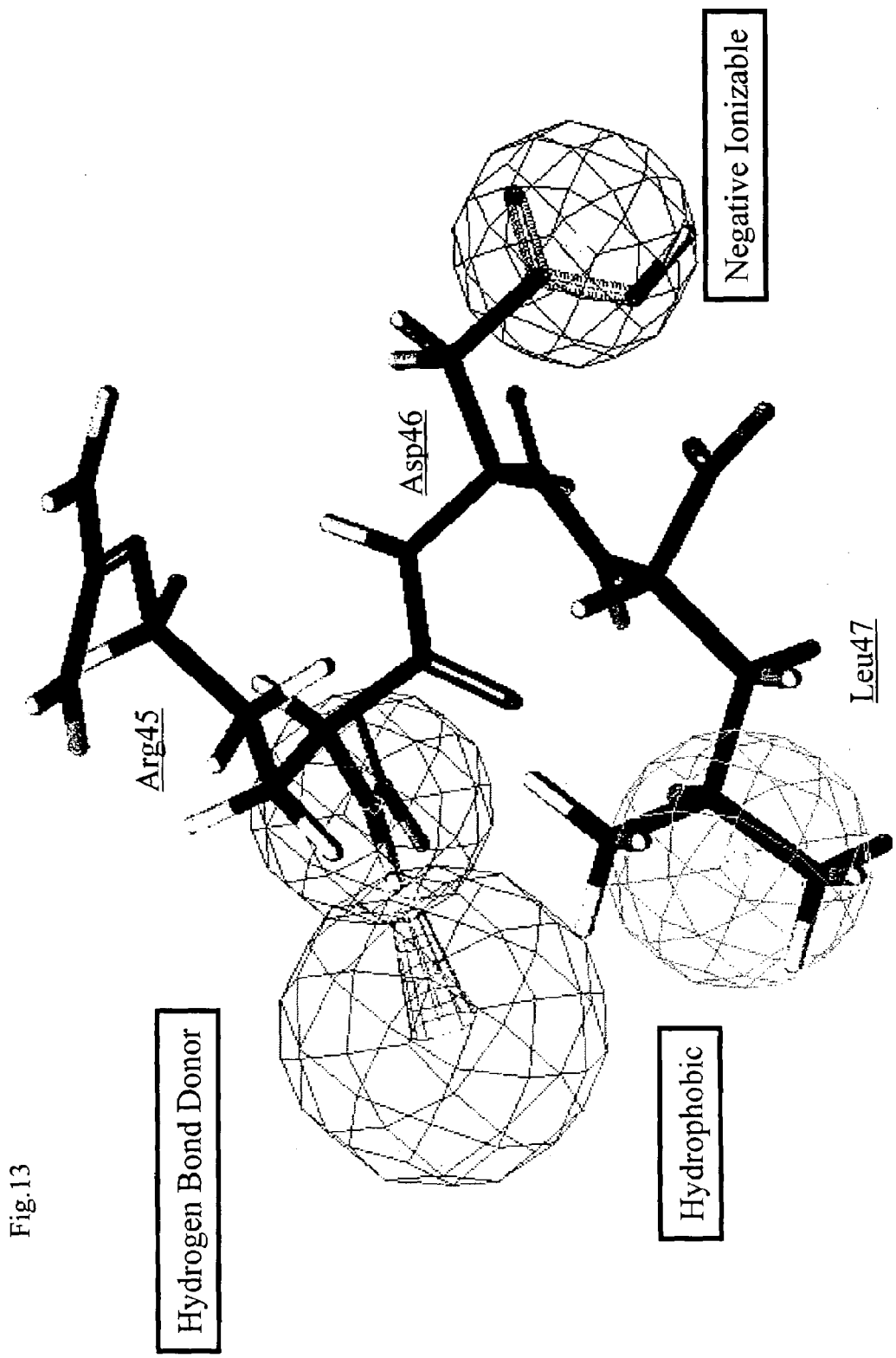

FIG. 13 shows an example of a pharmacophore constructed using the structure coordinates of the EGF-EGFR complex.

Figure 14:
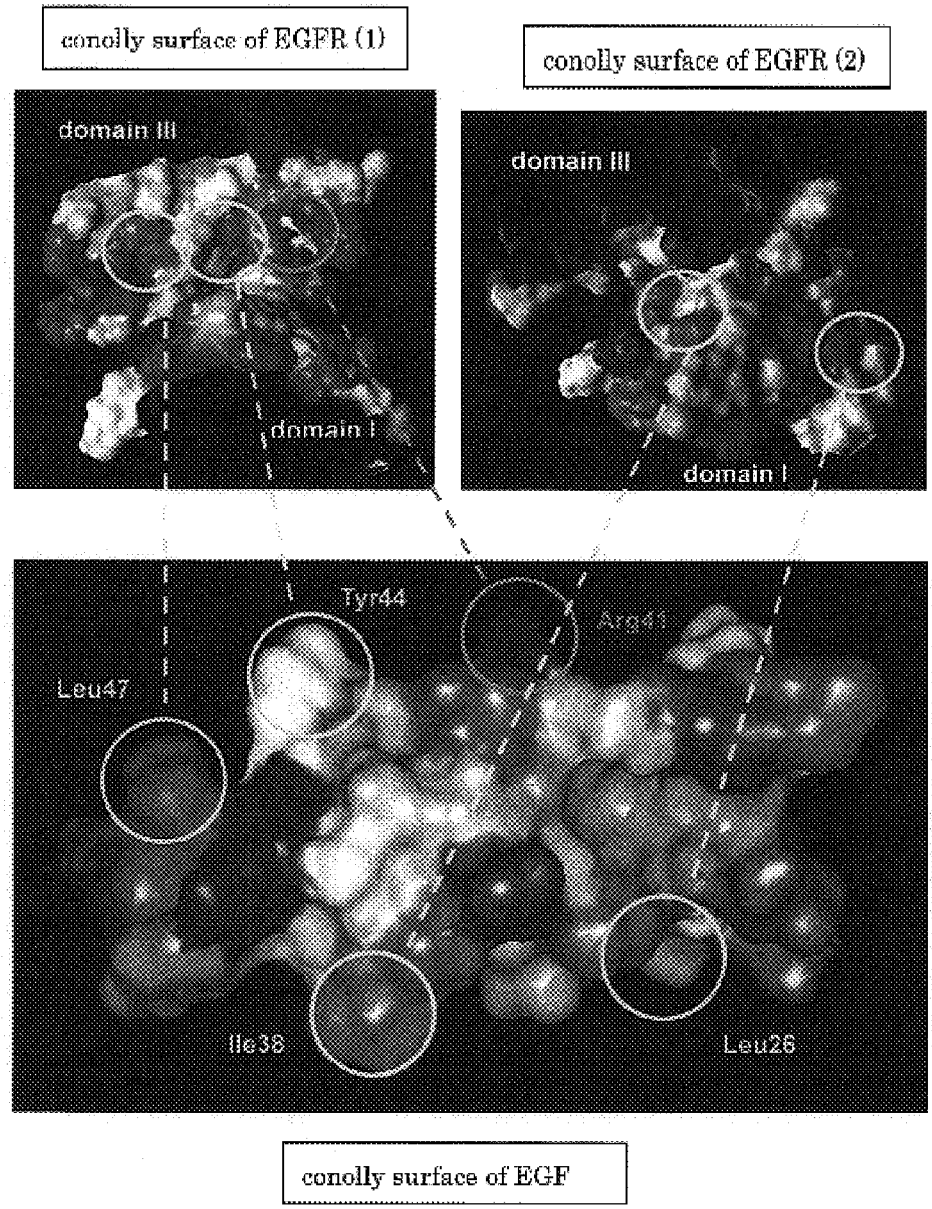

FIG. 14 shows photographs showing the conolly surface images of EGF and EGFR (receptor).

Figure 15:
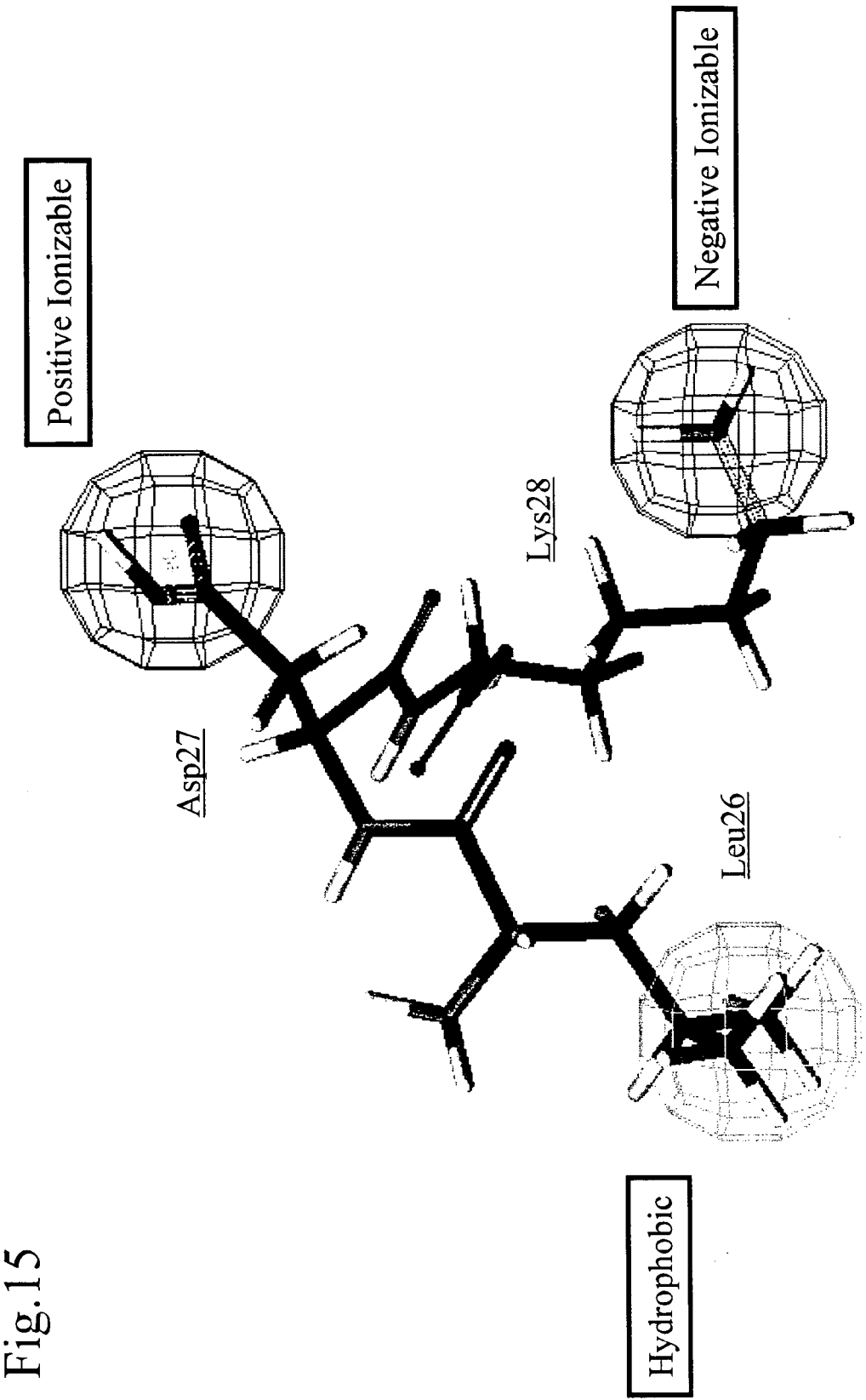

FIG. 15 shows a pharmacophore example (hypothesis "a") constructed using the structure coordinates of the EGF-EGFR complex.

Figure 16:
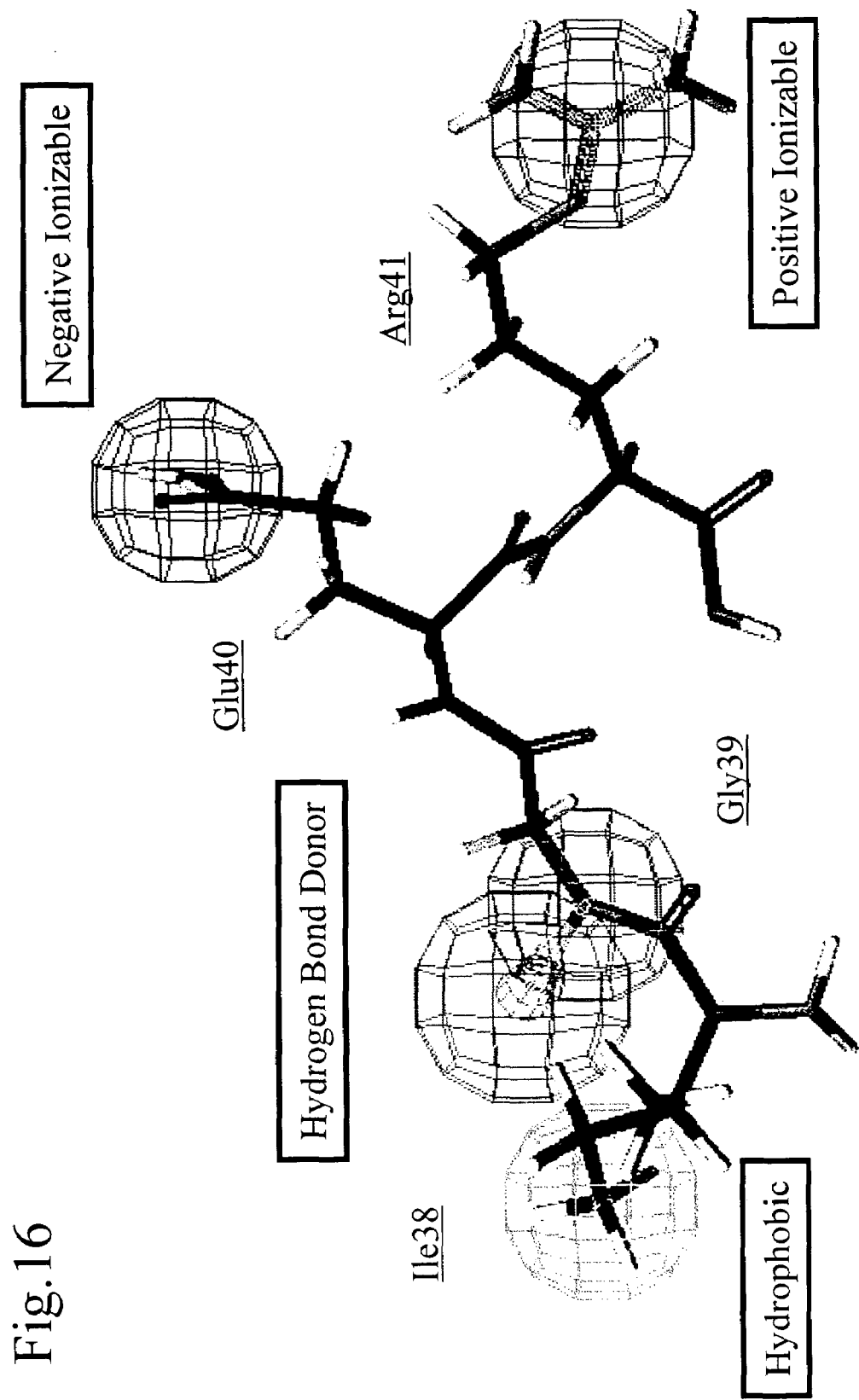

FIG. 16 shows a pharmacophore example (hypothesis "b") constructed using the structure coordinates of the EGF-EGFR complex.

Figure 17:
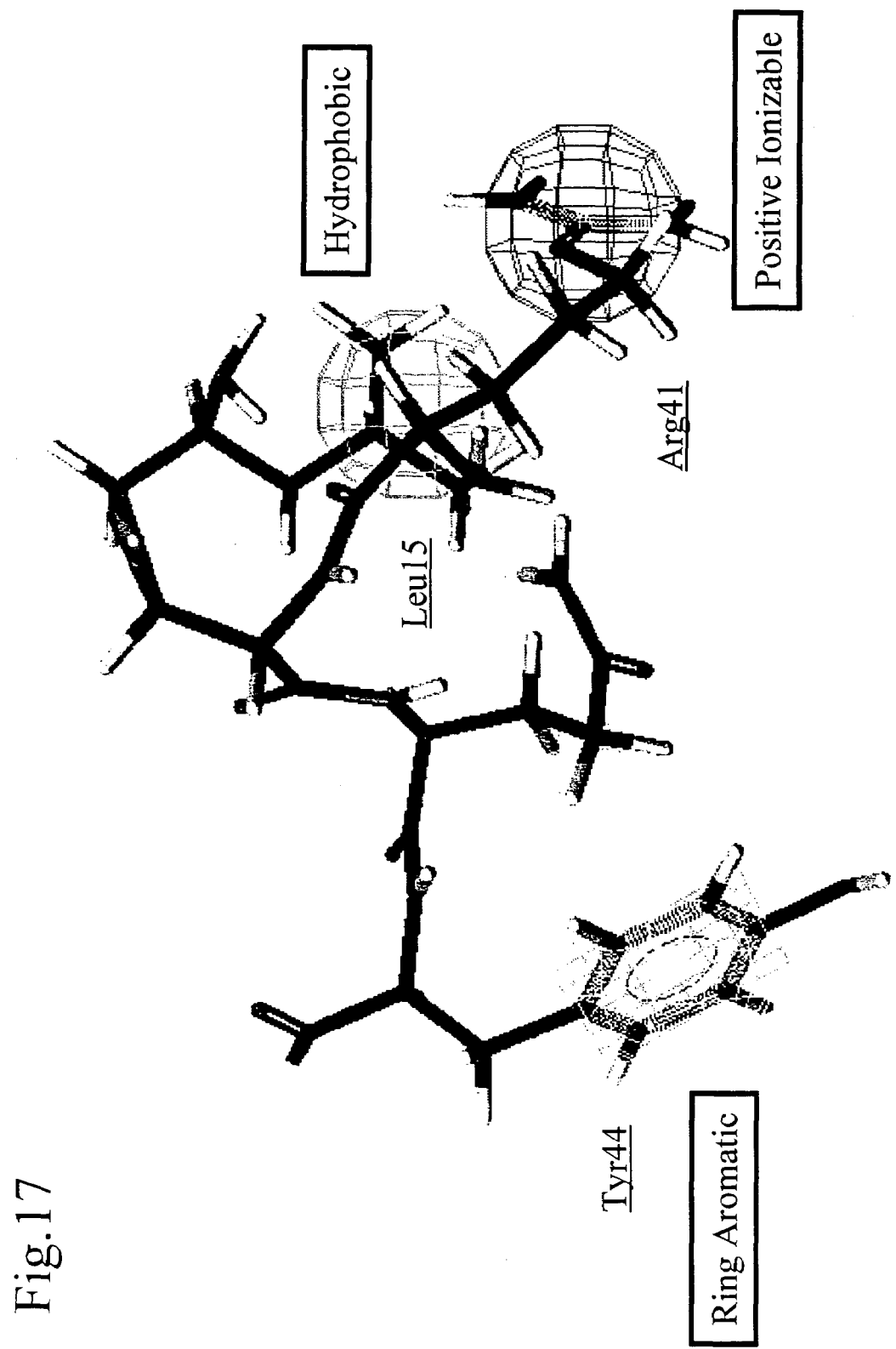

FIG. 17 shows a pharmacophore example (hypothesis "c") constructed using the structure coordinates of the EGF-EGFR complex.

Figure 18:
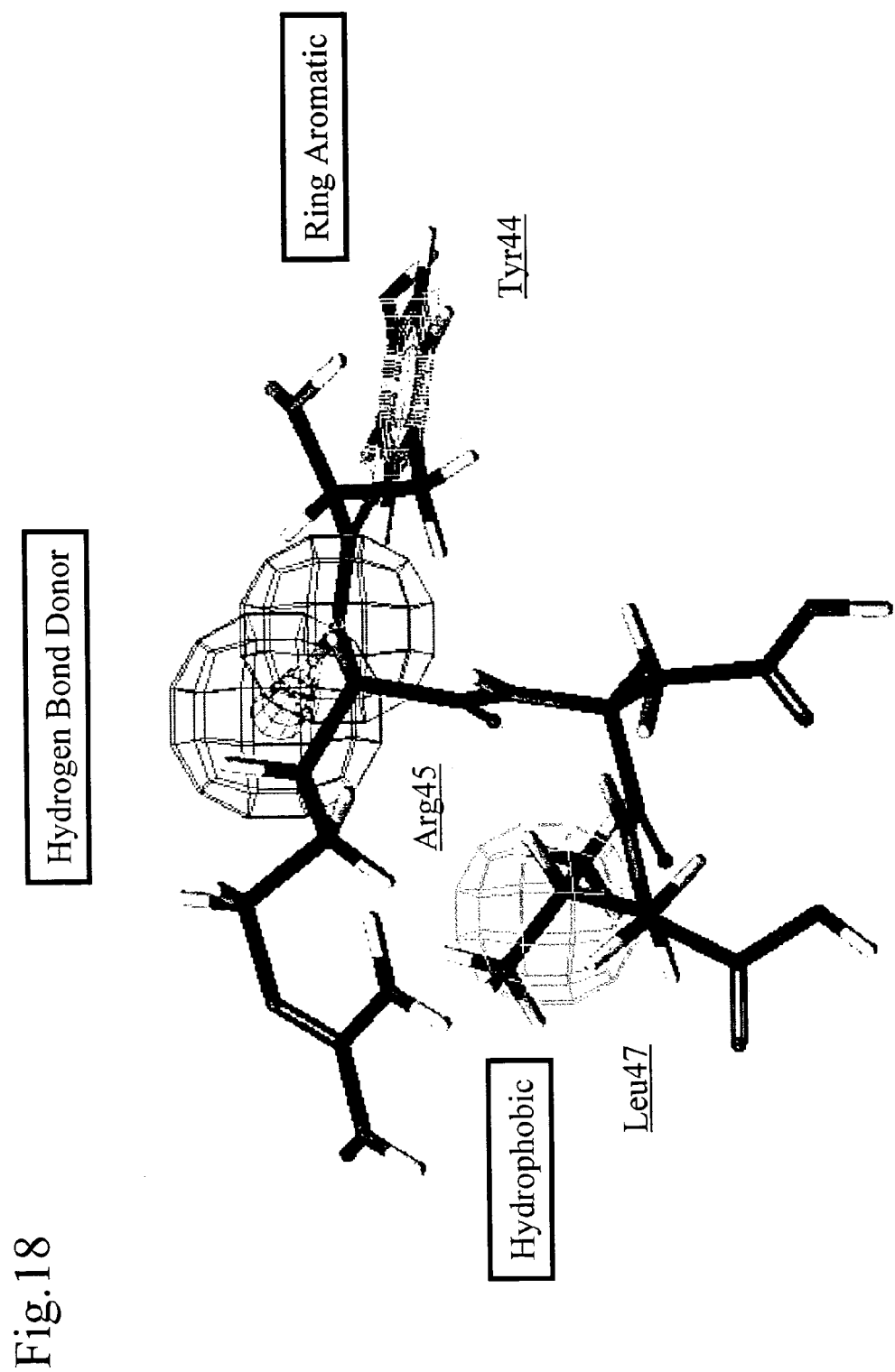

FIG. 18 shows a pharmacophore example (hypothesis "d") constructed using the structure coordinates of the EGF-EGFR complex.

Figure 19:
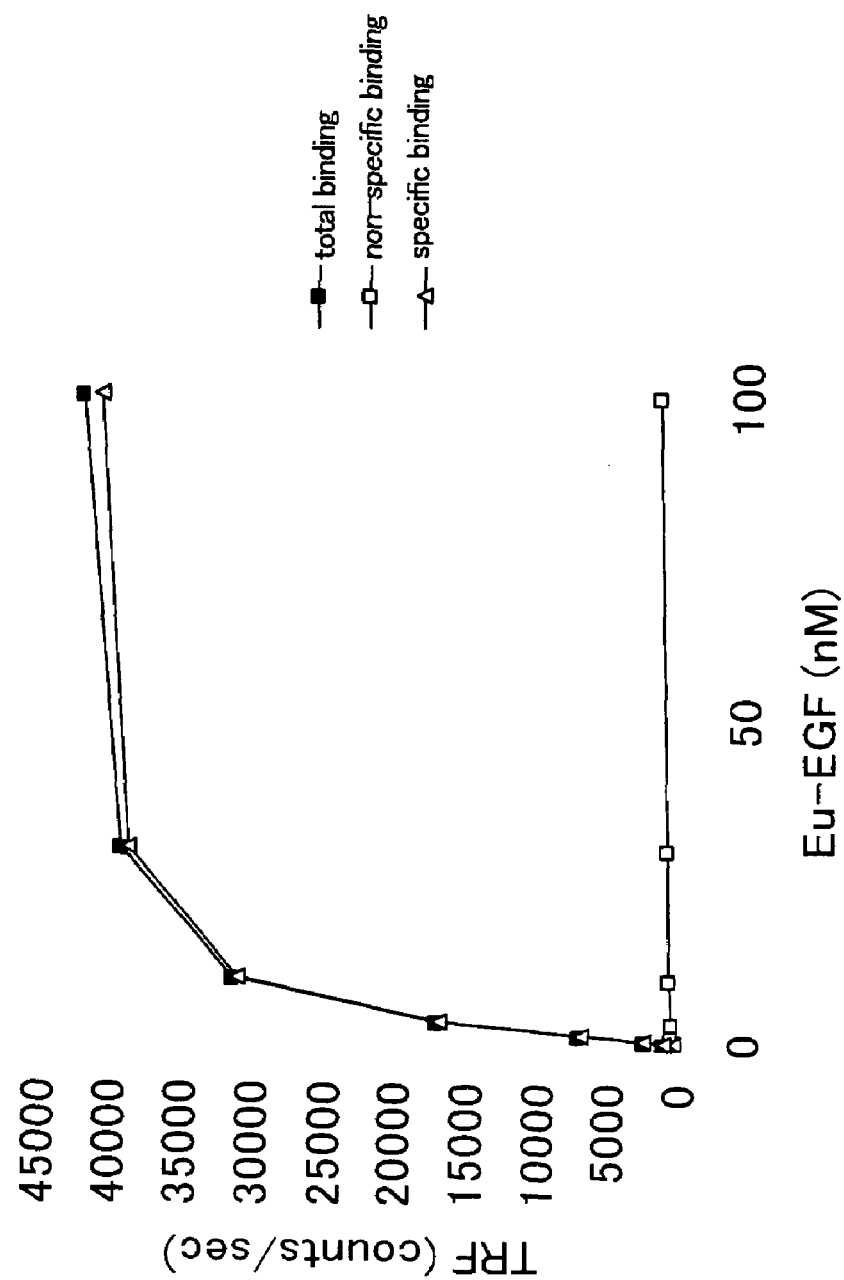

FIG. 19 shows saturation curves upon binding of europium-labeled EGF with EGFR on A431 cells.

Figure 20:
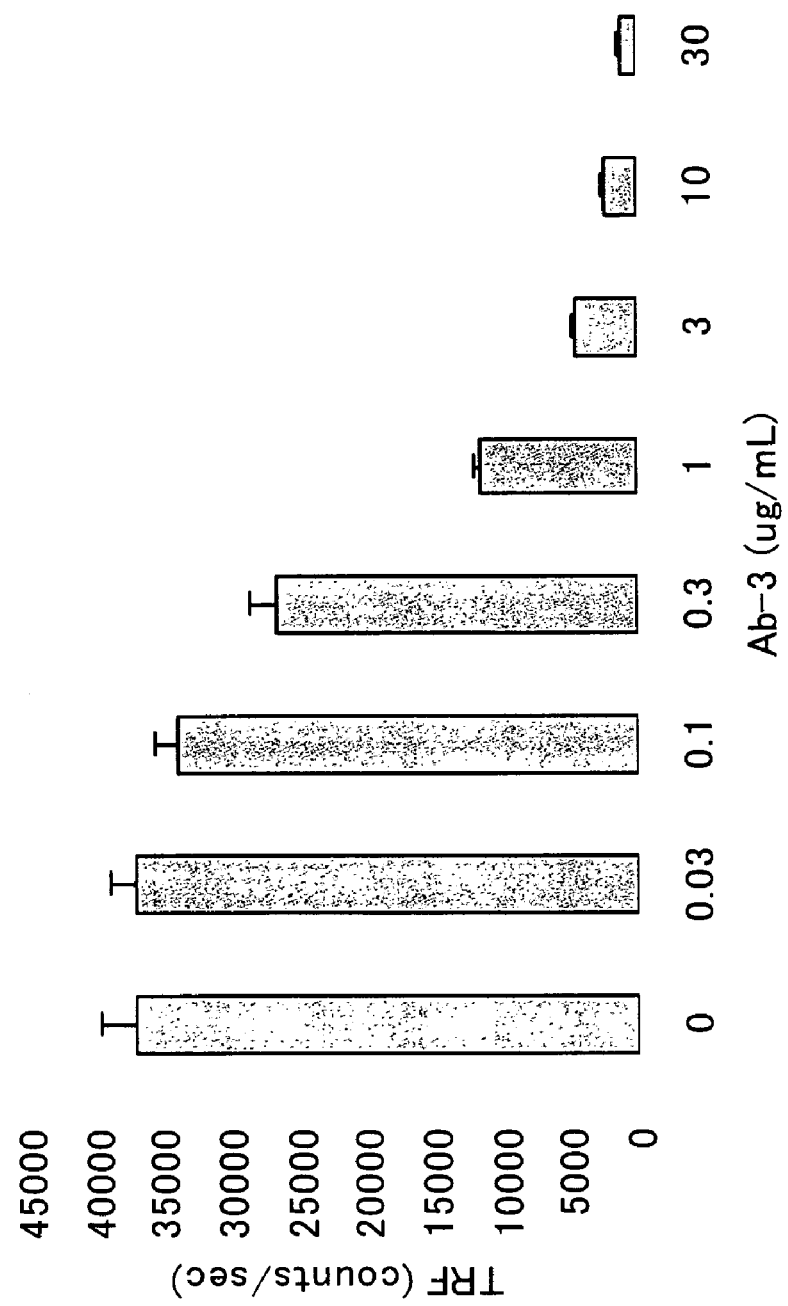

FIG. 20 shows binding inhibition by EGFR antibody (Ab-3) against binding of EGFR (A431 cell) with europium-labeled EGF (10 nM).

Figure 21:
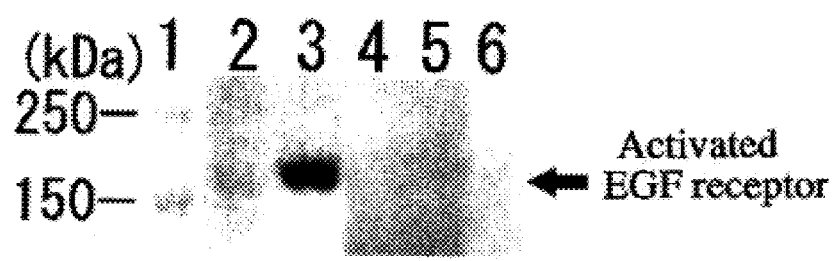

FIG. 21 shows a photograph showing inhibition activity of a test compound on EGFR phosphorylation. Lane 1 denotes a molecular-weight marker. Lane 2 denotes a sample to which no EGF has been added and then electrophoresed, lane 3 denotes a sample to which EGF has been added and then electrophoresed, lane 4 denotes a sample to which EGF and 2-[2-(3-ethyl-5,5,8,8-tetramethyl-5,6,7,8-tetrahydro-naphthalene-2-yl)-2-oxo-ethylsulfanyl]-nicotinic acid (100 μg/mL) have been added and then electrophoresed, lane 5 denotes a sample to which EGF and 10-[3-(4-methyl-piperazine-1-yl)-propyl]-2-trifluoromethyl-10H-phenothiazine dihydrochloride (10 μg/mL) have been added and then electrophoresed, and lane 6 denotes a sample to which EGF and 8-hexylsulfanyl-3-methyl-7-propyl-3,7-dihydro-purine-2,6-dione (10 μg/mL) have been added and then eletrophoresed.

Figure 22:
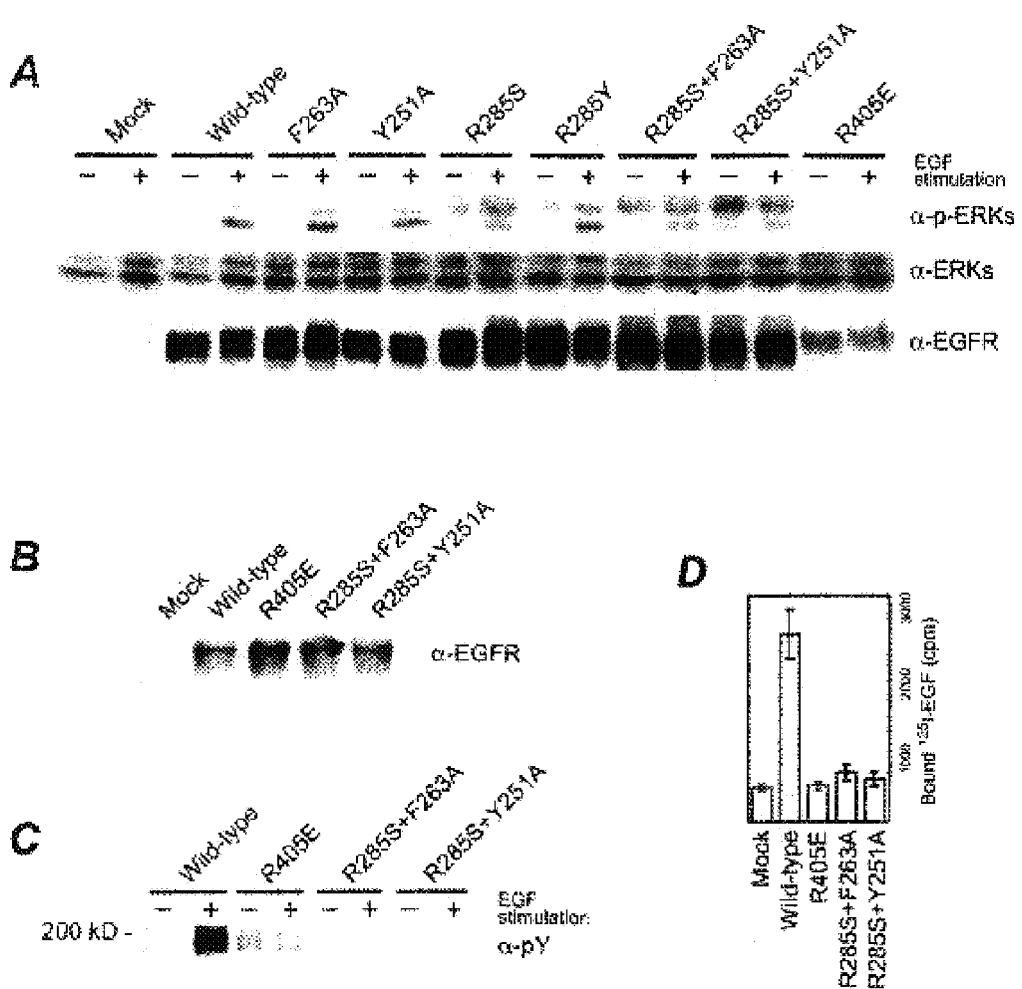

FIG. 22 shows photographs showing EGF-dependent EGFR activation in CHO cells expressing variant EGFR.

A: EGF-dependent ERK phosphorylation is shown.

B: Cell surface expression of variant EGFR is shown.

C: EGF-induced autophosphorylation of EGFR is shown.

D: Binding of $^{125}$I-labeled human EGF (2 nM) to cells expressing variant EGFR is shown. SD (n=3) is shown as an error bar.

BEST MODE OF CARRYING OUT THE INVENTION

The present invention will be hereafter described in detail by referring to examples, but the technical scope of the present invention is not limited by these examples.

EXAMPLE 1

Expression of EGF and EGFR (1) Expression of EGFR

Using a forward primer and a reverse primer shown below, the expression plasmid pcDNA-sEGFR (amino acids 1 to 619 of SEQ ID NO: 1) was prepared by standard PCR protocols.

Forward primer (including a restriction enzyme cleavage site and an ATG initiation codon)

Sequence: 5'-cgg gga gct agc atg cga ccc tcc ggg acg gcc ggg-3' (SEQ ID NO: 8)

Reverse primer (including a thrombin cleavage site, a FLAG epitope, a TAG stop codon)

Sequence: 5'-gcgc ctt aag cta ctt gtc atc gtc gtc ctt gta gtc gga tcc acg cgg aac cag gat ctt agg ccc att cgt tgg ac-3' (SEQ ID NO: 9)

PCR was conducted for 25 cycles of reaction (94° C. for 30 seconds, 55° C. for 15 seconds, and 75° C. for 1 minute) using pcDNA-EGFR containing DNA encoding full-length human EGFR as a template and PwoDNA polymerase (Roche).

The amplified DNA was cloned into the pcDNA3.1/Zeo(+) (Invitrogen), the plasmid for mammalian expression, thereby preparing the plasmid pcDNA-sEGFR. The vector plasmid was transfected to Lec8 cells (ATCC CRL-1737) by the Lipofectamine method according to instructions of the kit (Gibco-BRL). Here, the Lec8 cells produce a protein having terminal sialic acid and galactose residue-deficient N-linked oligosaccharides. Stable transfectants were selected using Zeocin (Invitrogen) at a concentration of 0.1 mg/ml, thereby isolating independent colonies. Subsequently, it was confirmed using the anti-FLAG M2 antibody (Sigma) that the thus obtained cells had expressed EGFR.

(2) Purification of EGFR

Using Dulbecco's modified Eagle's medium and Ham's F-12 medium (1:1) (DMEM/F12) supplemented with 10% calf serum (Gibco-BRL), 100 units/ml penicillin, 100 μg/ml streptomycin and 20 mg/l proline, the Lec8 transfectants were maintained (37° C., 5% $CO_2$ incubator). For large-scale EGFR production, the Lec8 transfectants were inoculated in the DMEM/F12 supplemented with 1% calf serum, 100 units/ml penicillin, 100 μg/ml streptomycin and 20 mg/l proline, followed by proliferation for 3 to 4 days. Subsequently, the culture supernatants were collected, and then centrifuged at 1500 rpm for 15 minutes. The cells were collected from the resulting flasks by scraping, and then transferred to other flasks to conduct expansion culture. The overall process was repeated while maintaining the cells for 3 months. The culture supernatants were collected, EDTA and PMSF were added at a final concentration of 0.4 mM, respectively. Serum globulin was removed by ammonium sulfate precipitation at 4° C. (280 g of ammonium sulfate was added per 1000 mL of a medium), and then 280 g of ammonium sulfate was further added per 1000 mL of a medium, thereby precipitating EGFR. The pellets were dissolved in 0.02 M phosphate buffer (pH7.1) (buffer A) and then dialyzed. The thus obtained EGFR-containing sample was stored at −80° C. The next step was conducted at 4° C. Next, the sample was loaded on tandemly connected, buffer A-equilibrated columns of DEAE-Toyopearl 650S (TOSOH CORPORATION), CM-Toyopearl 650S (TOSOH CORPORATION), and Affi-Gel Blue Gel (Bio-Rad). The protein was eluted from the disconnected Affi-Gel Blue column with a linear gradient of 0.02-0.6 M NaCl in buffer A. The eluate was applied to an anti-FLAG M2 affinity gel (Sigma) column equilibrated with buffer A with an additional 0.15M NaCl and circulated overnight. Proteins bound to the column were recovered with 0.1 M glycine-HCl buffer (pH3.5), and were neutralized immediately. The thus obtained sample was condensed with a UK-10 membrane (TOSOH CORPORATION), dialyzed against 0.02 M Tris-HCl (pH8.0) and 0.02 M NaCl (buffer B), and then loaded onto a Mono-Q column (Pharmacia) equilibrated with buffer B. Protein was eluted with a linear gradient of 0.02-0.2 M NaCl in buffer B. The thus obtained EGFR was condensed with Centricon-10 (Amicon), and the enzymatically deglycosylated as described below. Using 0.4 unit/ml endoglycosidase D (SEIKAGAKU CORPORATION) and 1 unit/ml endoglycosidase H (Roche) in a 0.1 M sodium acetate buffer (pH 5.3), 2 mg/ml EGFR, the concentration of which was determined using the extinction coefficient (0.65) at 280 nm, was incubated (under a nitrogen or an argon gas atmosphere at 37° C. for 50 hours). After the reaction mixture was diluted 10 fold with buffer B, deglycosylated EGFR (dEGFR) was purified on the Mono-Q column (purification was conducted similarly to the above procedure employed for the Mono-Q column).

For the expression of EGFR having selenomethionine instead of methionine, DMEM/F12 (SeMet medium) containing 50 ml of fresh selenomethionine instead of methionine, 1% dialyzed calf serum, 100 units/ml penicillin, 100 μg/ml streptomycin, and 40 mg/l proline was prepared. For the production of selenomethionyl EGFR, cells were grown to achieve a confluent culture in a manner similar to the above, followed by exchange of the medium to SeMet medium. After a 12 to 24 hour preincubation, the cells were cultured in fresh SeMet medium for 2 to 3 days, and then the medium was harvested. Selenomethionyl dEGFR was purified in the same way as for the native dEGFR as described above.

(3) Results

Extracellular domains of EGFR had already been purified with a conditioned medium from an A431 cancer cell line, a recombinant insect cell line expressing EGFR, or a recombinant Chinese hamster ovary cell expressing EGFR. For crystallization, we have developed a purification method for isolating extracellular domains of EGFR produced by recombinant Lec8 cells.

Figure 6:
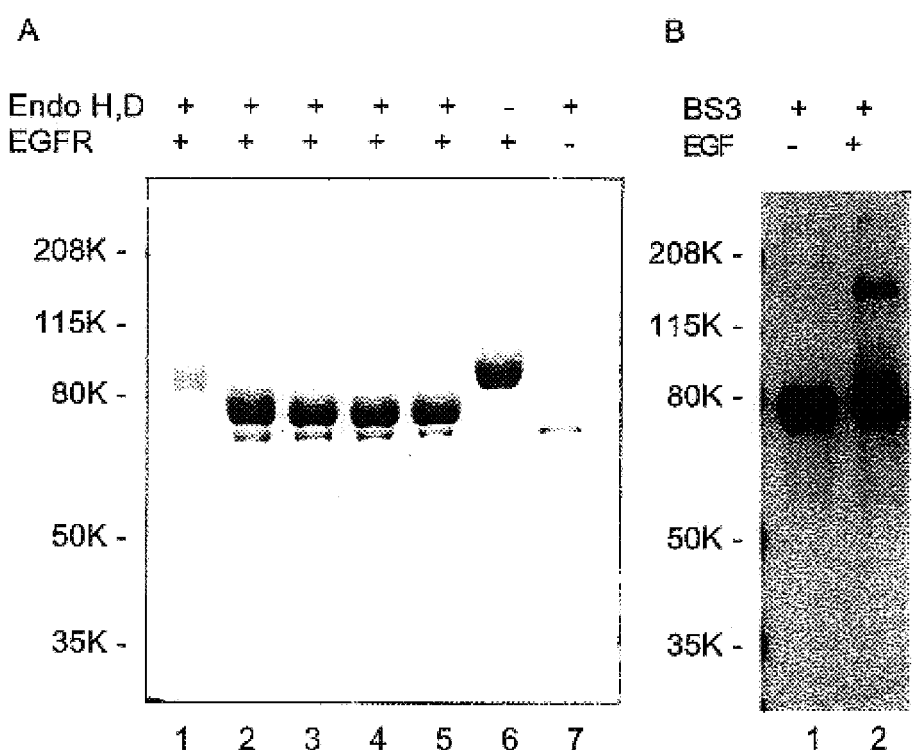
FIG. 6 shows photographs showing the result of SDS-PAGE analysis made for deglycosylated EGFR and the result of that for EGF-dependent dimerization by chemical cross-linking.

First, most of contaminants such as a serum protein were removed by ammonium sulfate fractionation. Next, the remaining contaminants were removed by affinity chromatography using FLAG tag. The heterogeneity of the sample was decreased by anion exchange chromatography. Using undeglycosylated purified protein, small crystals were grown, but no X-ray diffraction images were obtained. To further decrease the heterogeneity of the molecular surfaces, purified proteins were strongly deglycosylated using endoglycosidase H and endoglycosidase D. Anion exchange chromatography was then conducted to remove enzymes and digested glycan. As a result, when determined by SDS-PAGE, the deglycosylated protein had shifted to a size of approximately 74 kDa as expected (FIG. 6). Since it is unable to digest FLAG tag using thrombin, FLAG-tagged dEGFR was used for crystallization and other experiments. The yield of dEGFR was approximately 1 mg per 3.5 l of the collected medium.

EXAMPLE 2

Crystallization of Dimeric EGF-EGFR Complex (1) Crystallization

The dEGFR-EGF complex for crystallization was prepared as follows. The purified dEGFR solution was concentrated to 10 mg/ml, as determined using the extinction coefficient (0.79) at 280 nm, using Centricon-10. An equimolar amount of recombinant hEGF (Pepro-Tech) in an equimolar amount was purified by reverse phase HPLC, freeze-dried, and then dissolved in the dEGFR solution. Crystallization was initiated by the hanging-drop vapor diffusion method starting from 3 μl of 11 mg/ml complex solution and 3 μl of reservoir buffer (15% PEG4000, 1% PEG6000, 0.075 M Tris-HCl (pH 8.4), 0.075 M sodium acetate, and 0.2 M sodium chloride). Crystals were grown at 20° C. for 3 weeks. The macro seeding method was used to reproducibly grow the crystal to 1×0.2×0.2 mm or more. We measured XAFS spectra and collected diffraction data set using BL41XU at the large synchrotron radiation facility, SPring-8. In addition, measurement was conducted at 100 K in the presence of cryoprotectant (18% PEG4000, 1.2% PEG6000, 0.09 M Tris-HCl (pH 8.4), 0.09 M sodium acetate, 0.24 M sodium chloride, 16% trehalose and 11% PEG400).

(2) Experiment of Chemical Cross-Linking

To conduct an experiment on EGF-induced dEGFR dimerization similarly for the case of wild-type EGFR, we conducted analysis by chemical cross-linking (FIG. 6).

0.8 mg/ml dEGFR was incubated with 0.07 mg/ml hEGF dissolved in 0.05 M Hepes-NaOH (pH 7.5) and 1 mM bis (sulfosuccinimidyl) substrate (BS3, Pierce Chemical) cross-linking agent. The reaction mixture was allowed to stand for 60 minutes, and then cross-linking reaction was quenched using 0.01 mM glycine. The cross-linking product was analyzed by SDS-PAGE.

As a result, in the presence of EGF, a single species with high molecular weight (corresponding to a dimeric size of 150 kD) was formed. In the absence of EGF, species with high molecular weight as described above was not detected, suggesting that dEGFR had formed a dimer in response to EGF.

(3) Result (Crystallization of Native Crystal and Data Collection)

The sparse matrix method was applied for screening for crystallization conditions. Using receptors that had been caused to form complexes with 11 mg/ml hEGF in an equimolar amount by the hanging drop vapor diffusion method, Crystal Screen Kit I and II (Hampton Research) were used at 20° C. As a result, the most promising conditions (No. 22 of Screen Kit I) were improved as conditions for growing crystals having diffraction ability. As a result of refining crystallization conditions, the crystals generally grew to a final size within approximately 4 weeks (FIG. 7). The crystal diffracted to approximately 3.5 Å with a mosaicity as high as 1°. To improve the crystal quality, the crystal was immersed in cryoprotectant, cooled stepwise to 0° C., and then allowed to stand on ice. The mosaicity decreased to approximately 0.5°.

The solvent content of the native crystal is 75% and the native crystal belongs to the space group of P3₁21 with a=b=220.2 Å and c=113.1 Å.

EXAMPLE 3

Structure Analysis of Dimeric EGF-EGFR Complex (1) Method

A native crystal and a selenomethionyl crystal belong to the space group of P3₁21 with a=b=220.2 Å and c=113.1 Å and with a=b=221.2 Å and c=114.2 Å, respectively. The asymmetric unit contains one 2:2 complex with 75% solvent content. The crystals were cautiously transferred by many steps from a harvest buffer (1.2-fold concentration of reservoir buffer) to cryoprotectant prepared by adding 16% trehalose and 11% PEG400 to harvest buffer. Before cryopreservation with liquid nitrogen, the crystals were slowly cooled to 4° C., followed by placing the crystals on ice for 2 days. This treatment decreased the mosaicity of the crystals. Diffraction data sets were collected from the cryopreserved crystals at 100 K on beamline BL41XU at SPring-8. The program HKL was used for data processing.

The scaled data set of the selenomethionyl crystals at a peak wavelength was used to calculate the normalized structure factor with the program DREAR™, and the program SnB was used for locating the selenium atoms. Therefore, the 13 consistent peaks were picked out of the 20 atoms expected to be in the asymmetric unit. The program MLPHARE™ was used for the heavy atom refinement and the initial phase calculation, and the program RESOLVE™ was used for the solvent flattening. Moreover, the program DM™ was used for non-crystallographic averaging and further solvent flattening. At this time, we traced the backbone in the resulting electron density obtained at 4.0 Å resolution. The program O was used for model building. Next, phase extension was conducted at 3.5 Å. The molecular replacement analysis was conducted with the program AMORE™ using the model determined by the MAD method as a search model. Using data collected at 3.5 Å, the native crystal structure was determined. The structure is shown in Table 1. Furthermore, using the data at 3.3 Å, the native crystal structure at 3.3 Å resolution was determined. The structure is shown in Table 2. The above model was built based on the electron density, and then refined by rigid-body refinement, energy minimization, restrained β-factor refinement, and simulated annealing procedures with the program CNS™. Moreover, the programs SIGMAA™ and RESOLVE™ were used for further electron density modification to have less bias toward the model. Iterative model building and density modification enhanced the quality of the electron density map. After the final refinement, the Ramachandran plot analysis with the program PROCHECK™ showed that 95.9% of the residues in the crystal structure shown in Table 1 and 95.5% of the residues in the crystal structure shown in Table 2 are in the most favored and additionally allowed regions. The programs, SIGMAA™ and PROCHECK™, are supported by CCP4.

In the crystal structure shown in Table 1, amino acid residues 1 and 2 and 513 to C-terminus of one receptor molecule, and amino acid residues 1 to 4 and 513 to C-terminus of the other receptor molecule in the dimer are disordered, and these regions were poorly defined in the electron density map. The electron densities for residues 1 to 4 and 50 to 53 in both ligand molecules were diffused. The crystal structure shown in Table 1 contains 1108 amino acids and 11 hydrocarbon residues. In the crystal structure shown in Table 2, amino acid residues 1, 158 to 162, 169 and 170, 179 and 180, 302 to 308, and 513 to the C-terminus of one receptor molecule and amino acid residues 1 and 2, 158 to 160, 179, 305 to 309, and 513 to the C-terminus of the other receptor molecule in the dimer are disordered. The electron densities for residues 1 to 4 and 50 to 53 in both ligand molecules are diffused. The crystal structure in Table 2 contains 996 amino acids, 10 hydrocarbon residues, and 79 water molecules.

(2) Result (Selenomethionyl dEGFR)

Both screening for a heavy atom derivative from the native crystal by the immersion method, and a series of expression, purification, and crystallization of dEGFR having selenomethionine instead of methionine were examined. We could not identify any potential heavy atom derivatives by the immersion method, however, we obtained a selenomethionyl crystal in a manner same as that for the native crystal. The selenomethionyl crystal belonged to the space group of P3₁21 with a=b=221.2 Å and c=114.2 Å and 75% solvent content. The crystal diffracted to 4.0 Å.

EXAMPLE 4

Homology Modeling Using Structure Coordinates of EGF-EGFR Complex (1) Construction of Model Structure The model structure of ErbB2 was built by using FAMS (Full Automatic Modeling System)(Ogata, K. et. al., J. Mol. Graph. Model., Vol. 18, pp. 258-272 (2000)). The amino acid sequence information of ErbB2 (EBR2 HUMAN) registered with SWISS-PROT was used to construct the initial model. At this time, as three-dimensional structure coordinates used for building a backbone structure by FAMS, the structure coordinates obtained by the our crystal structure of the EGF-EGFR complex were used. Furthermore, as database used for building side chain structure, FAMS original database was used. As a result, structure coordinates of a portion of 24th to the 541st amino acid residues of an amino acid sequence shown in SEQ ID NO: 5 were obtained.

After the construction of the model structure, it was verified that there are no theoretical problems on the thus constructed coordinates using a program for evaluating protein three-dimensional structure such as Profiles-3D that is a module of InsightII (Accelrys Inc., San Diego, Calif.) molecular design-supporting software package. This model structure is shown in FIG. 12.

Modeling was conducted by same techniques also for ErbB3 (SEQ ID NO: 6), ErbB4 (SEQ ID NO: 7), the insulin-like growth factor-1 receptor (SEQ ID NO: 3), and the insulin receptor (SEQ ID NO: 4), thereby obtaining model structures.

(2) Prediction of Ligand-Binding Site

Structure conserved region (SCR) of a modeling structure was superimposed on that of the EGFR three-dimensional structure. While comparing with the alignment table used for the initial structure construction, amino acid residues in the modeling structure, which are present at positions almost the same in terms of three dimensional coordinates as those of amino acids in EGFR interacting with EGF were extracted. These amino acid residues were considered to interacting amino acid residues. The results are shown in FIG. 11.

EXAMPLE 5

Generation of Pharmacophores

An example of a pharmacophore can be specified as follows using the information on the amino acid residues extracted from the information on the complex structure. The following interaction is exemplified as interaction that is thought to be particularly useful for pharmacophore generation (Table 4).

TABLE 4

| EGF amino acid residue | EGFR amino acid residue | Binding type | Possibility of pharmacophore |
|---|---|---|---|
| Arg45 | Gln384 | Hydrogen bond formation between main chain and side chain | High |
| Asp46 | Agr29 | Salt linkage | Particularly high |
| Leu47 | Leu382 Ala415 Val417 | Hydrophobic interaction | Particularly high |

The interaction contains 3 interaction sites that are closely adjacent to each other and capable of interacting with both domains of domain I and domain III. Hence, it is likely to be specified as a pharmacophore capable of searching not only an EGFR antagonist, but also an EGFR agonist. A specific example of such a pharmacophore is specified by the active conformation of tripeptides, Arg45, Asp46, and Leu47, upon binding with EGFR.

Next, the EGF structure was read into a commercial software package for virtual screening, such as Catalyst, and then interacting atoms or functional groups were converted into appropriate spheres representing pharmacophoric features as shown in Table 5 below using the function-mapping function of Catalyst, thereby generating a pharmacophore.

TABLE 5

| Residues on EGF | Spheres representing pharmacophoric features |
|---|---|
| Arg45: NH group of main chain | Hydrogen Bond Donor (HBD) region |
| Asp46: carboxyl group of side chain | Negative Ionizable (NI) region |
| Leu47: side chain | Hydrophobic (HP) region |

The pharmacophore is specified by the coordinates of the following 3 spheres representing pharmacophoric features.

Sphere 1 representing pharmacophoric features; the negative ionizable region having a center represented by an X-coordinate of −5.623, a Y-coordinate of 6.259, and a Z-coordinate of 0.853, and a radius of 1.5 Å.

Sphere 2 representing pharmacophoric features; the hydrophobic region having a center represented by an X-coordinate of −12.656, a Y-coordinate of 3.363, and a Z-coordinate of −2.934, and a radius of 1.5 Å.

Sphere 3 representing pharmacophoric features; the hydrogen bond donor region which is defined by a vector represented by a hydrogen bond donor region R (route) as a start point having a center represented by an X-coordinate of −11.576, a Y-coordinate of 9.546, and a Z-coordinate of −2.135, and a radius of 1.5 Å, and a hydrogen bond donor region T (terminal) as an end point having a center represented by an X-coordinate of −13.86, a Y-coordinate of 8.532, and a Z-coordinate of −3.792, and a radius of 2.0 Å.

The pharmacophore is shown in FIG. 13.

Example 6

Screening Method Using Structure Coordinates and Pharmacophore of EGF-EGFR Complex (1) Virtual Screening Utilizing DOCK
(1-1) Specifying Search Site
The three dimensional structure of the structure coordinates in Table 1 obtained from the results of analysis made on the EGF-EGFR co-crystal structure was visually displayed using software InsightII (Accelrys Inc.,). Conolly surface views of EGF (ligand) and EGFR (receptor) are shown in FIG. 14.

When FIG. 14 was observed, among residues extruding convexly on EGF, residues shown with circular symbols in this figure were shown to correspond to the pockets on EGFR. These portions are thought to be promising ligand-binding site candidates.

Hence, based on the above information, three sites (site 1, site 2, and site 3) on EGFR were supposed to be ligand-binding sites, and DOCK spheres were set at positions of major atoms on EGF amino acid residues thought to interact with each site. The sites used for this docking study are shown in Table 6.

TABLE 6

| Site | Important residues (EGF side) | Type | Major interacting residues (EGFR side) |
|---|---|---|---|
| 1 | Leu26 | Hydrophobic | Ala68, Leu69, Leu98 |
|   | Lys28 | Basic | Glu35 |
| 2 | Leu15 | Hydrophobic | Leu325, Val350 |
|   | Cys31 | Hydrogen bonding | Gln16 |
|   | Asn32 | Hydrogen bonding | Gln16, Gly18 |
|   | Cys33 | Hydrogen bonding | Gly18 |
|   | Ile38 | Hydrophobic | Leu17, Thr10, Leu27 |
|   | Gly39 | Hydrogen bonding | Asn12 |
|   | Arg41 | Basic | Asp355 |
| 3 | Tyr44 | Hydrophobic | Leu382, His346, |
|   | Arg45 | Hydrogen bonding | Gln384 |
|   | Asp46 | Acidic | Arg29 |
|   | Leu47 | Hydrophobic | Ala415, Ile438, Phe412, Val417, Leu382, Gln408 |

(1-2) Construction of Compound Database
As a compound database to be searched, compound information registered with ACD (Available Chemicals Directory; MDL Information Systems, Inc.) was used. First, the ACD compound information was exported in the sd file format. Then data processings such as salt removal, generating three-dimensional data for compound structures by CORINA (Molecular Networks GmbH), file conversion to "mol2" file format using accessories attached to DOCK, and charge allocation were carried out, thereby generating a compound database for DOCK (170,855 compounds). Furthermore, data in the compound database constructed by the above techniques was divided into a compound group (acd_a: 19,270 compounds) containing acidic functional groups and a compound group (acd_b: 151,585 compounds) containing no such groups. These compound groups were analyzed separately.

(Note: DOCK tends to estimate scores of acidic functional groups unreasonably high. Thus, in this study, the above processings were carried out, and analyses were made separately.)

(1-3) Implementation of Docking Study
DOCK4.0.1 was conducted for each site on the compound database generated in (1-2). Docking was performed by a flexible docking method by which ligand conformation is generated upon calculation.

The obtained results were sorted in ascending order of docking scores (lower the docking score (the function for evaluating ligand-protein binding energy), the better fitting with the protein), thereby extracting top 5000 compounds. Of these compounds, compounds having conformation adjacent to the important residues were extracted ((1) in Table 7) with a self-made script (script for calculating the distance between an important EGFR residue and a ligand), and then compounds having conformation by which appropriate interaction with each important residue could take place were selected by visual observation ((2) in Table 7). Furthermore, compounds having structures unfavorable as drugs and compounds (e.g., pigments) likely to show false-positive results at the time of assaying activity were removed, thereby obtaining finally selected compounds ((3) in Table 7). (a) denotes acd_a, and (b) denotes acd_b.

TABLE 7

| Sites | Residues used for extraction | Number of selected compounds (a) (1)→(2)→(3) | Number of selected compounds (b) (1)→(2)→(3) |
|---|---|---|---|
| 1 | Leu26, Lys28 | 586→93→68 | 501→91→59 |
| 2 | Tyr44, Arg41 | 138→16→7 | 267→11→4 |
| 3 | Leu47 and Asp46 and Arg45 | 316→128→82 | 234→86→38 |

(1-4) Cluster Analysis of Hit Compounds in Docking Study

The hit compounds selected in (1-3) contain compound groups that are structurally (backbone) similar to each other. These compound groups are highly likely to be similar to each other in their docking scores and docking modes. Therefore, simply selecting assay candidate compounds in descending order from docking scores, the resulting set is likely to be poor in structural variety.

When structural variety is poor, the compound groups are likely to be similar to each other in safety and ADME (absorption, distribution, metabolism, and excretion) profiles. However, it is difficult to predict in silico safety and ADME profiles with current technology. When such a compound set is determined as an assay candidate compound set, these compounds are highly likely to be unable to cope with a risk of drop out due to an unexpected side effect, which often takes place during drug development.

Hence, cluster analysis made on each hit compound of (1-3) while focusing on structural similarity and classification of the compounds into several structurally similar groups make it possible to secure structural variety (see Tables 8 and 9 below). One representative compound selected from each group may be subjected to biochemical assay.

In addition, optclus (Barnard Chemical Information Ltd.) was used for determining the number of optimal division groups in each hit, and Daylight Clustering Package (Daylight Inc.) was used for cluster analysis.

TABLE 8

| acd_a | | |
|---|---|---|
| Site | Number of hit compounds in docking study | Number of groups |
| 1 | 68 | 25 |
| 2 | 7 | 6 |
| 3 | 82 | 55 |

TABLE 9

| acd_b | | |
|---|---|---|
| Site | Number of hit compounds in docking study | Number of groups |
| 1 | 59 | 13 |
| 2 | 4 | 3 |
| 3 | 38 | 4 |

(2) Virtual Screening Utilizing DOCK and AUTODOCK (2-1) Low Molecular Weight Compound Library A library was generated (307481 molecules in total) from the ACD low molecular weight compound database. At this time, when multiple molecules were contained in a single data entry, the data were divided into each data set for one molecule, so as to eliminate redundancy. Subsequently, the data were narrowed down based on "Lipinski's Rule of 5." Conditions for narrowing the data used herein are as follows.

1) Molecular weight: 100 or more and 500 or less
2) Calculation LOGP value (o/w) (XLOGP-1 algorithm was used) 5 or less
3) Number of acceptor atoms (the number of N and the number of O contained in a compound) 10 or less
4) Number of donor atoms (number of NH and number of OH contained in a compound) 5 or less Furthermore, molecules as shown below were excluded in order to appropriately conduct docking calculation.

1) Number of rotatable single bonds is 21 or more.
2) Radicals are contained.
3) Elements other than H, C, N, O, F, S, P, Cl, Br, and I are contained.

As a result of this narrowing-down procedure, a low molecular weight compound set consisting of 222096 molecules was obtained.

(2-2) Binding Site Prediction (2-2-1) Domain Definition

Chain A of EGFR was divided into 3 domains (domain I: Glu2-Lys165, domain II: Cys166-Val312, and domain III: Cys313-Val512). Domains I and III contain an interface between EGF and EGFR, and domain II contains an interface for EGFR dimerization.

(2-2-2) Site Definition

EGF and EGFR create intermolecular interaction at three sites. An interface created by Leu14, Gln16, Gly18, Tyr45, Leu69, Glu90, and Leu98 of EGFR and Met21, Ile23, Leu26, Lys28, Cys31, Asn32, and Cys33 of EGF is defined as site 1. An interface created by Val350, Asp355, and Phe357 of EGFR and Tyr13, Leu15, and Arg41 of EGF is defined as site 2. An interface created by Leu382, Gln384, Phe412, and Ile438 of EGFR and Gln43, Arg45, and Leu47 of EGF is defined as site 3. Site 1 is contained in domain I, and site 2 and site 3 are contained in domain III. Here, a low molecular weight compound inhibiting the intermolecular interaction was searched for each site by in silico screening.

(2-2-3) Prediction of Binding-Site

Binding sites were predicted for each of the above 3 sites using a program Sphgen contained in a docking program Suite Dock.

On molecular surface, Sphgen generates a sphere having a radius corresponding to geometrical shape of the molecule. Multiple overlapping spheres are collected as one cluster, and then finally multiple clusters that are independent to each other are generated. Regions occupied by these clusters are predicted binding sites. This calculation was conducted using predetermined default values of Sphgen.

For site 1, from among clusters adjacent to this site, a hydrophobic environment composed of Leu14, Tyr45, Leu69, and Leu98 of EGFR and Met21, Ile23, and Leu26 of EGF, and those adjacent to salt bridges linking Glu90 residue on the EGFR side and Lys28 residue on the EGF side were selected. Among spheres contained in these clusters, spheres subjected to shaping so that those arranged at the hydrophobic pockets and the peripheral portions thereof had been deleted were selected as putative binding sites for site 1.

For site 2, from among spheres contained in the clusters adjacent to site 2, spheres wherein the distance from each of Val350, Asp355, and Phe357 of EGFR and Tyr13, Leu15, and Arg41 of EGF creating intermolecular interaction to a center of each sphere was within 4 Å were selected.

Also for site 3, from among spheres contained in clusters adjacent to site 3, spheres where the distance from each of Gln384, Phe412, and Ile438 of EGFR and Gln43, Arg45, and Leu47 of EGF creating intermolecular interaction to a center of each sphere was within 4.4 Å were similarly selected.

(2-3) Docking Simulation Conditions

Docking simulation was conducted (primary screening) by docking all the 222096 molecules of the low molecular weight compounds contained in the library generated in (2-1) to each binding site defined in (2-2) using software Dock 4.0. To improve calculation accuracy, among parameters predetermined for DOCK, the following parameters were changed from their default values.

configurations_per_cycle=30 (default 25)
maximum_orientations=1000 (default 500)

More detailed docking was conducted (secondary screening) using AutoDock 3.0.5 for top 10347 molecules for site 1, top 16929 molecules for site 2, and top 10500 molecules for site 3. Here, the following parameters were also changed to improve calculation accuracy.

ga_num_evals=1500000 (default 250000)

(2-4) Docking Simulation Result

For the docking structures of the low molecular weight compounds obtained as a result of the secondary screening by AutoDock, the distance between each of Ile23, Leu26, and Lys28 of EGF for site 1, Tyr13, Leu15, and Arg41 of EGF for site 2, and Gln43, Arg45, and Leu47 of EGF for site 3 and a center of each sphere (as used in the primary screening) was calculated. Compounds in which the shortest distance was 4 Å or more were excluded, because they were predicted to bind at a position away from a target binding site. Subsequently, the low molecular weight compounds were sorted in order of AutoDock scores. Thus, top 2500 molecules for site 1, top 808 molecules for site 2, and top 879 molecules for site 3 were determined to be ligand candidate compounds that bind to a protein. Subsequently, these compounds were classified based on interaction manners with the protein. Here, the distance between the protein and a heavy atom (atoms other than hydrogen) of each compound was calculated. Among residues being in contact with each compound at a distance within 4 Å, residues electrostatically interacting with each compound were determined to be "important interacting residues," and residues other than such residues were determined to be "interacting residues." Compounds that were analogous to the "interacting residues" and "important interacting residues" in appearance pattern on the primary sequence of the protein were classified into one cluster. It is expected that a compound interacting with EGFR residues that interact with EGF has higher inhibition activity. Hence, it was considered that compounds contained in cluster 2 (319 compounds) for site 1, those contained in cluster 2 (188 compounds) for site 2, and those contained in clusters other than clusters 5, 6, and 12 (871 compounds) for site 3 had high inhibition activity.

(2-5) Cluster Analysis of Hit Compounds in Docking Study

Cluster analysis was conducted for the hit compounds in (2-4) by the method according to (1-4). Results are shown in Table 10.

TABLE 10

| Site | Number of hit compounds in docking study | Number of groups |
| --- | --- | --- |
| 1 | 319 | 33 |
| 2 | 188 | 33 |
| 3 | 871 | 33 |

(3) Virtual Screening Utilizing Catalyst (3-1) Specification of Search Site (Generation of Catalyst Hypothesis)

The three-dimensional structure of the structure coordinates in Table 1 obtained from analytical results for the co-crystal structure was visually displayed using software InsightII™ (Accelrys Inc., San Diego, Calif.), and then the EGF-EGFR interaction sites were visually observed. As a result, pharmacophoric patterns thought to be important were extracted from EGF (ligand). The pharmacophoric hypotheses extracted and utilized for search are as shown below. In addition, since a Catalyst™ hypothesis with shape taken into consideration requires at least 3 pharmacophores, a hypothesis was generated from a pharmacophoric pattern wherein a pharmacophore is located at a hydrophobic pocket and contains 2 or more interaction sites. Spheres representing pharmacophoric features were determined by reading extracted partial structures into a commercial software package for virtual screening such as Catalyst™, and then converting data of interacting atoms or functional groups into appropriate spheres representing pharmacophoric features using the function-mapping function of Catalyst™. Thus, pharmacophores were generated. Furthermore, the EGF partial structures utilized for extracting the pharmacophores were caused to fit corresponding pharmacophores, and then the EGF partial structures were converted to hypothetical molecular shapes using the "Convert Molecule to Shape" function of Catalyst™. By linking the hypotheses and original pharmacophores, pharmacophoric hypotheses taking similarity in three-dimensional molecular shape into consideration were constructed.

In addition, molecular shapes were generated by a default method. Furthermore, when residues corresponding to each other are distant from each other in terms of primary structure (e.g., Leu15 and Arg41), their binding was simulated at a portion closest to each residue, and then shape construction was conducted.

(a) Leu26, Asp27, and Lys28 (Site 1)

Sphere 1 representing pharmacophoric features (Leu26 side chain), the hydrophobic region having a center represented by an X-coordinate of −5.669, a Y-coordinate of −1.630, and a Z-coordinate of −1.200, and a radius of 1.5 Å.

Sphere 2 representing pharmacophoric features (carboxyl group of Asp27 side chain), the negative ionizable region having a center represented by an X-coordinate of −4.547, a Y-coordinate of 6.304, and a Z-coordinate of 4.060, and a radius of 1.5 Å.

Sphere 3 representing pharmacophoric features (amino group of Lys28 side chain), the positive ionizable region having a center represented by an X-coordinate of −0.842, a Y-coordinate of 2.938, and a Z-coordinate of 0.169, and a radius of 1.5 Å.

(b) Ile38, Gly39, Glu40, and Arg41 (Site 2)

Sphere 1 representing pharmacophoric features (guanidyl group of Arg41 side chain), the positive ionizable region having a center represented by an X-coordinate of 4.527, a Y-coordinate of 6.119, and a Z-coordinate of −0.725, and having a radius of 1.5 Å.

Sphere 2 representing pharmacophoric features (carboxyl group of Glu40 side chain), the negative ionizable region having a center represented by an X-coordinate of 0.459, a Y-coordinate of −1.861, and a Z-coordinate of 1.410, and a radius of 1.5 Å.

Sphere 3 representing pharmacophoric features (NH group of Gly39 backbone), the hydrogen bond donor region of which is defined by a vector represented by a hydrogen bond donor region R (route) as a start point having a center represented by an X-coordinate of −6.534, a Y-coordinate of 3.496, and a Z-coordinate of −0.247, and a radius of 1.5 Å, and a hydrogen bond donor region T (terminal) as an end point having a center represented by an X-coordinate of −8.045, a Y-coordinate of 1.617, and a Z-coordinate of 1.538, and a radius of 1.7 Å.

Sphere 4 representing pharmacophoric features (Ile38 side chain), the hydrophobic region having a center represented by an X-coordinate of −11.024, a Y-coordinate of 2.667, and a Z-coordinate of 0.128, and a radius of 1.5 Å.

(c) Leu 15, Arg41, and Tyr44 (Site 2)

Sphere 1 representing pharmacophoric features (Tyr44 side chain), the ring aromatic region of which is defined by a vector represented by a ring aromatic region R (route) as a start point having a center represented by an X-coordinate of −5.416, a Y-coordinate of 7.542, and a Z-coordinate of −2.184, and a radius of 1.5 Å, and a ring aromatic region T (terminal) as an end point having a center represented by an X-coordinate of −8.185, a Y-coordinate of 6.587, and a Z-coordinate of −2.827, and a radius of 1.5 Å.

Sphere 2 representing pharmacophoric features (guanidyl group of Arg41 side chain), the positive ionizable region having a center represented by an X-coordinate of −16.119, a Y-coordinate of 9.326, a Z-coordinate of −0.341, and a radius of 1.5 Å.

Sphere 3 representing pharmacophoric features (Leu15 side chain), the hydrophobic region having a center represented by an X-coordinate of −14.846, a Y-coordinate of 5.806, and a Z-coordinate of −1.676, and a radius of 1.5 Å.

(d) Tyr44, Arg45, and Leu47 (Site 3)

Sphere 1 representing pharmacophoric features (Tyr44 side chain), the ring aromatic region of which is defined by a vector represented by a ring aromatic region R (route) as a start point having a center represented by an X-coordinate of 6.595, a Y-coordinate of −0.996, and a Z-coordinate of −1.663, and a radius of 1.5 Å, and a ring aromatic region T (terminal) as an end point having a center represented by an X-coordinate of 7.625, a Y-coordinate of 1.482, and a Z-coordinate of −0.322, and a radius of 1.5 Å.

Sphere 2 representing pharmacophoric features (NH of Arg45 backbone), the hydrogen bond donor region of which is defined by a vector represented by a hydrogen bond donor region R (route) as a start point having a center represented by an X-coordinate of 1.858, a Y-coordinate of 1.046, and a Z-coordinate of 1.370, and a radius of 1.5 Å, and a hydrogen bond donor region T (terminal) as an end point having a center represented by an X-coordinate of 2.051, a Y-coordinate of 2.626, and a Z-coordinate of −1.172, and a radius of 1.7 Å.

Sphere 3 representing pharmacophoric features (Leu47 side chain), the hydrophobic region having a center represented by an X-coordinate of −1.936, a Y-coordinate of 0.021, and a Z-coordinate of −3.278, and a radius of 1.5 Å.

Here, a root is defined by a start point of a vector and a terminal is defined by an end point of the vector, respectively. The ring plane in a ring aromatic region is defined as a plane having an R-to-T vector as a perpendicular. Each arrangement of the spheres representing pharmacophoric features shown in (a) to (d) is graphically expressed as shown in FIGS. 15 to 18.

(3-2) Construction of Compound Database

As a compound database to be searched, compound information registered with the ACD (Available Chemicals Directory; MDL Information Systems, Inc.) was used. First, the ACD compound information was exported in the sd file format, and then converted into an exclusive database format (catDB module, Accelrys Inc.), thereby constructing a database (231,777 compounds) for Catalyst.

(3-3) Implementation of Catalyst

The compound database constructed in (3-2) was searched for compounds fitting 4 ((a) to (d)) pharmacophores shown in (3-1) and the pharmacophore (referred to as "e") generated in Example 5 using Catalyst4.6 (Accelrys Inc.) ((1) in Table 11). As a result of this search, compounds matching all hypothetical spheres contained in each pharmacophore were selected. Furthermore, compounds having structures unfavorable as drugs and compounds that were likely to show pseudo-positiveness when assayed (e.g., pigments) for activity were eliminated, thereby finally selecting compounds ((2) in Table 11).

TABLE 11

| Hypothesis | Pharmacophore | Number of hit compounds (1)→(2) |
| --- | --- | --- |
| a | Leu26, Asp27, Lys28 (site 1) | 13→13 |
| b | Ile38, Gly39, Glu40, Arg41 (site 2) | 2→2 |
| c | Leu15, Arg41, Tyr44 (site 2) | 0 |
| d | Tyr44, Arg45, Leu47 (site 3) | 68→57 |
| e | Arg45, Asp46, Leu47 (site 3) | 16→12 |

EXAMPLE 7

EGF-EGFR Binding Inhibition Assay (1) Production of Europium-Labeled Ligand

When the crystal structure of an EGF-EGFR complex was analyzed, it was determined that Asn, the N-terminal site of a ligand (EGF), does not significantly participate in direct interaction with EGFR. Thus, the N-terminus was chemically modified with an europium chelate compound (DELFIA Eu-N1, PerkinElmer life sciences). Synthesis of europium-labeled EGF was consigned to PerkinElmer life sciences, so that 1.5 mg of europium-labeled EGF (hereinafter denoted as Eu-EGF) dissolved in 50 mmol/L Tris-HCl bufferd saline (pH 7.8) at a concentration of 48 µmol/L was obtained.

(2) EGF-Binding Experiment Using A431 Cells and Binding Inhibition by Antibody

A431 cells (human squamous cell carcinoma cells, purchased from ATCC) for use in this experiment were subcultured using a medium (hereinafter denoted as a medium) prepared by adding inactivated FBS (JRH), Penicillin-streptmycin (GIBCO), and Amphotelicin B (Sigma) at final concentrations of 10 vol %, 50 U/mL-50 µg/mL, and 1 µg/mL, respectively, to DMEM (Sigma). A431 cells suspended in the medium were inoculated into a 96-well microtiter plate (black, COSTAR) at 10,000 cells/100 µL/well, and then pre-cultured overnight in a $CO_2$ incubator (37° C., 5% $CO_2$). After the media within the wells had been completely removed, the wells were washed once in 50 mmol/L HEPES-HCl (pH 7.8, hereinafter denoted as a Buffer) containing 138 mmol/L NaCl, 5 mmol/L KCl, 1.2 mmol/L $MgSO_4$, 1.2 mmol/L $CaCl_2$, 75 µmol/L EDTA and 0.2 vol % BSA, and then a Buffer was added at 49 µL/well. Subsequently, DMSO was added at 1 µL/well, and then Eu-EGF that had been diluted with a Buffer at various concentrations were added at 50 µL/well. The plate was incubated at room temperature for 1 hour, washed 5 times with an ice-cold buffer (200 µL/well), and then a DELFIA enhancement reagent (PerkinElmer life sciences) was added at 100 µL/well. After further 30 minutes of incubation at room temperature, time-resolved fluorescence was measured using a plate reader (ARVO-sx, PerkinElmer life sciences). Excitation wavelength and emission wavelength used herein were 340 nm and 615 nm, respectively.

As a result of this experiment, increased fluorescence was observed in an Eu-EGF concentration-dependent manner, and saturation of binding was almost observed at a final concentration of 30 nmol/L of Eu-EGF or more (FIG. 19). In addition, non-specific binding was expressed as a fluorescence value measured for a well to which unlabeled EGF had been added at a final concentration of 50 µmol/L before the addition of Eu-EGF. A value of specific binding was calculated by subtracting a measured value of non-specific binding from a value measured at each ligand concentration. Furthermore, when Scatchard plot was generated based on free ligand concentrations and values of specific binding, Kd=2.2 nmol/L was obtained by calculation from the slope of an approximate straight line. Furthermore, when anti-EGFR monoclonal antibodies (Ab-3, Oncogene) prepared at various concentrations were added, subsequently Eu-EGF was added at a final concentration of 10 nmol/L in the above experiment system, fluorescence decreased in an antibody concentration-dependent manner, so that the inhibition of EGF binding by the antibodies was confirmed (FIG. 20). Based on the above results, it was concluded that screening of compounds inhibiting EGF-EGFR binding is possible using this assay system.

(3) Screening for Compounds Selected by Computer Screening

A representative compounds for site 1 of 2) in Example 6, a representative compounds for site 2 of 2) in Example 6, and a representative compounds for site 3 of 1) in Example 6 were subjected to this assay. A431 cells that had been suspended in a medium were inoculated into a 96-well microtiter plate (black, COSTAR) at 10,000 cells/100 µL/well, and then pre-cultured overnight in a $CO_2$ incubator (37° C., 5% $CO_2$). Media within the wells were completely removed, and then the wells were washed once with a Buffer. Subsequently, a Buffer was added at 49 µL/well. Samples were prepared by weighing 3 to 8 mg of test compounds and dissolving them in DMSO at a concentration of 10 mg/mL. The sample was added at 1 µL/well, incubated at room temperature for 5 minutes, and then to which Eu-EGF that had been diluted with a Buffer to a final concentration of 5 nmol/L was added at 50 µL/well. The plate was incubated at room temperature for 1 hour, washed 5 times with an ice-cold Buffer (200 µL/well), and then to which a DELFIA enhancement agent (PerkinElmer life sciences) was added at 100 µL/well. After 30 minutes of incubation at room temperature, time-resolved fluorescence was measured using a plate reader (ARVO-sx, PerkinElmer life sciences). Excitation wavelength and emission wavelength used herein were 340 nm, and 615 nm, respectively. Assay was run in duplicate, and then data were processed using each average measured value. In data processing, the inhibition activity (%) was calculated by subtracting a measured value of non-specific binding from a measured value of each group to which DMSO and samples had been added, calculating a specific ligand binding ratio (%) in a group to which samples had been added when the specific ligand binding ratio of a group to which DMSO had been added was determined to be 100% and the non-specific binding ratio was determined to be 0%, and then subtracting the thus calculated specific ligand binding ratio from 100%. Furthermore, pseudo-positive samples were eliminated by the following method. Specifically, DMSO and each sample were diluted with a Buffer, and then incubated with A431 cells at room temperature for 1 hour, followed by 5 times of washing. Eu-EGF and a DELFIA enhancement reagent (PerkinElmer life sciences) were added, incubation was conducted at room temperature for 30 minutes, and then time-resolved fluorescence was measured using a plate reader (ARVO-sx, PerkinElmer life sciences). Compounds with clearly decreased fluorescence compared with that for the measured value of the group to which DMSO had been added were eliminated as pseudo-positive. Compounds other than these compounds were determined to be active. The active compounds were added at final concentrations of 1, 3, 10, and 30 µg/mL, inhibition activities were calculated, and then $IC_{50}$ values were calculated by the nonlinear least square fitting.

(4) Result

From the representative compounds for site 1, a compound showing $IC_{50}$=8.0 µg/mL: 10-[3-(4-methyl-piperazine-1-yl)-propyl]-2-trifluoromethyl-10H-phenothiazine dihydrochloride (purchased from Sigma, catalog number: T8516) was obtained. From the representative compounds for site 2, a compound showing $IC_{50}$=13.0 µg/mL: 8-hexylsulfanyl-3-methyl-7-propyl-3,7-dihydro-purine-2,6-dione (purchased from SALOR, catalog number: R33,683-1) was obtained. From the representative compounds for site 3, a compound showing $IC_{50}$=23.8 µg/mL: 2-[2-(3-ethyl-5,5,8,8-tetramethyl-5,6,7,8-tetrahydro-naphthalene-2-yl)-2-oxo-ethylsulfanyl]-nicotinic acid (purchased from MAYBRIDGE, catalog number: RH00866) was obtained.

EXAMPLE 8

Evaluation of EGFR Agonist Activity and EGFR Antagonist Activity Using EGFR Phosphorylation as an Index When EGFR is activated by binding of a ligand, intracellular regions are phosphorylated. This phosphorylation is detectable using a phosphorylated receptor-specific antibody. A431 cells were cultured (BNR-110M, ESPEC CORP.) using Dulbecco's Modified Eagle's Medium (Sigma) containing 10% fetal calf serum (JRH Bioscience) under an environment of 5% $CO_2$ at 37° C. for 1 day. The cells were then cultured in a serum-free medium for 1 day. When agonist activity was assayed, a medium containing a sample at a concentration of 10 µg/mL was added, and then the resultant was allowed to stand for 10 minutes. Furthermore, when antagonist activity was assayed, a medium containing a sample at a concentration of 10 µg/mL or 100 µg/mL was added, and then the resultant was allowed to stand for 20 minutes. Subsequently, EGF (Pepro Tech, Inc.) was added to a final concentration of 100 ng/mL, and then the resultant was further allowed to stand for 10 minutes. In addition, cells that had been treated with EGF only and untreated cells were prepared as controls.

The media were removed, the cells were washed with cooled phosphate buffered saline (PBS, Sigma), and then a heated cell lysis buffer (125 mmol/L Tris (Wako Pure Chemical Industries, Ltd.)-hydrochloric acid (Wako Pure Chemical Industries, Ltd.) buffer (pH 6.8) containing 20% glycerol (Wako Pure Chemical Industries, Ltd.), 2% SDS (Sigma), 5% 2-Mercaptoethanol (Sigma), and 0.025 mg/mL Bromo Phenol Blue (Sigma)) was added, thereby obtaining a cell lysate solution. The obtained cell lysate was applied to 7.5% polyacrylamide gel (e-PAGEL, ATTO Corporation), and then subjected to separation by electrophoresis (AE-6400, ATTO Corporation) under a condition of 30 mA per sheet of gel using Tris/glycine/SDS buffer (Bio-Rad Laboratories, Inc.). The resultant was transferred to a polyvinylidene difluoride (PVDF) membrane (clear blot membrane-P, ATTO Corporation) under conditions of 200 mA for 1 hour using semi-dry blotting system (AE-6675, ATTO Corporation). The PVDF membrane was blocked using PBS containing 5% skim milk (Wako Pure Chemical Industries, Ltd.) at room temperature for 1 hour. After blocking, the membrane was incubated with a primary antibody against an activated EGF receptor (anti-human activated EGFR antibody•mouse IgG1: BD Transduction Laboratories) diluted 1:1000 with PBS containing 0.1% Tween-20 (Bio-Rad Laboratories, Inc.), and then with a secondary antibody labeled with horseradish peroxidase (anti-mouse immunoglobulin•rabbit polyclonal antibody/peroxidase label: DAKO Corporation) at 37° C. for 1 hour. Subsequently, the EGF receptor activated by the action of EGF was detected by a chemiluminescence method (ECL western blotting detection system, Amersham Biosciences) using a system for photographing luminescence and fluorescence and outputting the data (AE-6962N, ATTO Corporation). 10 μg/mL 10-[3-(4-methyl-piperazine-1-yl)-propyl]-2-trifluoromethyl-10H-phenothiazine dihydrochloride, 10 μg/mL 8-hexylsulfanyl-3-methyl-7-propyl-3,7-dihydro-purine-2,6-dione, and 100 μg/mL 2-[2-(3-ethyl-5,5,8,8-tetramethyl-5,6,7,8-tetrahydro-naphthalene-2-yl)-2-oxo-ethylsulfanyl]-nicotinic acid inhibited activation of the EGF receptor of A431 cells due to EGF (FIG. 21).

EXAMPLE 9

Production of EGFR Variant (1) Method

The site-directed mutagenesis method was performed using the QuickChange® site-directed mutagenesis kit according to the instructions of the manufacturer (Stratagene). The mutation in the EGFR sequence was confirmed by DNA sequence analysis. CHO cells were cultured in Minimum Essential Medium α supplemented with 10% calf serum. By using the FuGENE6 method according to the manufacturer's recommendation (Roche), the cells were transfected with an expression vector carrying the wild type or variant receptor. The transiently transfected CHO cells were cultured for 24 hours, unless otherwise described, and were used for the next analyse with and without a 24 hour starvation, followed by stimulation with human EGF for 5 minutes.

The expression of EGFR and the downstream ERKs activation in the transiently transfected CHO cells were determined according to Kim et al (Kim, J.-H. et al., Eur. J. Biochem. 269: 2323-2329, 2002). Moreover, immunoblot analyse were performed using an anti-EGFR polyclonal antibody (Upstate Biotechnology), an anti-phosphorus-p44/42 MAP kinase E10 monoclonal antibody, and an anti-MAP kinase polyclonal antibody (Cell Signaling Technology).

Next, for the wild type and ERK activation-deficient mutants, the EGFR expression on the surface of the transiently transfected CHO cells was confirmed by the 2 different methods shown below. In the $1^{st}$ method, the cell surface proteins were biotinylated, and then the biotinylated EGFR was detected according to the method described by Muthuswamy et al (Muthuswamy, S. K. et al., Mol Cell Biol. 19: 6845-6857, 1999). In the $2^{nd}$ method, the cell surface EGFR of the transiently transfected CHO cells was labeled with the anti-EGFR 528 monoclonal antibody (Santa Cruz), and then was analyzed using a FACS Vantage SE system (Becton Dickinson) according to the instructions of the manufacturer.

To detect autophosphorylation induced by EGF, the transiently transfected cells were cultured for 12 hours, and then starved in serum-free medium for 3 hours. EGFR autophosphorylation was determined by the method previously reported by Sato et al (Sato, C. et al., J. Biochem (Tokyo) 127: 65-72, 2000). As for the EGF-binding assay, the transiently transfected cells were maintained for 24 hours in a 24-well plate coated with fibronectin, and then starved for 24 hours in serum-free medium. These cells were incubated for 1 hour with 2 nM $^{125}$I-labeled EGF in phosphate buffered saline (PBS) containing 1 mg/ml BSA. The free $^{125}$I-labeled EGF was removed by 3 times of washing using ice-cold PBS containing 1 mg/ml BSA. Subsequently, the cells were lysed in 0.5 ml of 0.5 M NaOH, and then radioactivity was measured using a γ counter.

(2) Result

Mutagenesis was conducted for the interface residues of EGFR, and then the effect on the activation of full-length EGFR was examined. First, to examine the downstream signal transduction pathway of EGFR expressed in CHO cells, EGF-dependent phosphorylation of the extracellular signal-regulated protein kinases (ERK) was assayed (FIG. 22A). In the hydrophobic receptor-dimerization interface, Tyr251 of one receptor interacts with Arg285 by hydrogen bond, and hydrophobically interacts with Phe263 of the other receptor. The substitution of Arg285 with Tyr (R285Y) had a negligible effect, but the substitution of Arg285 with Ser (R285S) reduced the biological activity (FIG. 22A).

Substitution of Tyr251 or Phe263 with Ala had negligible effects. However, the combination of R285S mutation with either Y251A or F263A resulted in almost complete loss of the activity. It was confirmed that a variant generated by a combination of R285S mutation with either Y251A or F263A was expressed on the cell surface at a level almost the same as that of wild type EGFR by both biotinylation analysis (FIG. 22B) and FACS analysis (data not shown). These nonsignaling forms were also incapable of EGFR autophosphorylation (FIG. 22C). As a result, the interface for receptor dimerization found in the crystal structure was verified by the site-directed mutagenesis. The two dimerization interface mutants showed much lower affinity for EGF in $^{125}$I EGF-binding assay (FIG. 22D). This suggests that the high-affinity of EGF binding is related to the EGFR dimerization.

Furthermore, an intracellular interaction between domain II and domain III of EGFR was also tested utilizing the site-directed mutagenesis method. At the domain-domain interface, Glu293 of domain II and Arg405 of domain III form salt bridge with each other. It was revealed that the substitution of Arg405 with Glu abolished the EGF binding due to EGF-dependent ERK phosphorylation, autophosphorylation, and high affinity EGF-binding (FIG. 22). Hence, the domain-domain interaction is important for the receptor activation.

INDUSTRIAL APPLICABILITY

The present invention provides the crystal structure and the three-dimensional structure of a dimeric EGF-EGFR complex. The structure coordinates provided by the co-crystal structure of the complex of the present invention are useful in extraction of a pharmacophore of an EGFR agonist or an EGFR antagonist, computer screening using all or some of the structure coordinates of the complex, molecular design (e.g., increased activity and provision of selectivity) of an EGFR agonist or an EGFR antagonist, design of an industrially useful EGF or EGFR variant, production of an EGF neutralization antibody or an EGF agonist antibody, a molecular replacement method utilizing the EGF-EGFR crystal structure, modeling of proteins thought to have folds similar to those of EGFR such as an insulin receptor and use of the structure thereof (e.g., computer screening, molecular design, antibody design, design of altered proteins, and the molecular replacement method) and the like.

---

LENGTHY TABLES

The patent contains a lengthy table section. A copy of the table is available in electronic form from the USPTO web site (http://seqdata.uspto.gov/?pageRequest=docDetail&DocID=US07514240B2). An electronic copy of the table will also be available from the USPTO upon request and payment of the fee set forth in 37 CFR 1.19(b)(3).

---

The invention claimed is:

1. A crystal of a complex of epidermal growth factor (EGF) comprising: the amino acid sequence of SEQ ID NO:2 and epidermal growth factor receptor (EGFR) having amino acids 1-619 of SEQ ID NO:1 capable of diffracting X-ray at a resolution of 3.3 Å, wherein the crystal has the following characteristics (A), (B), and (C):

(A) EGF binds to EGFR at a 1:1 ratio;
   (B) the EGF-bound EGFRs form a dimer; and
   (C) the crystal has the space group $P3_121$, the unit cell parameters: a=220.2±1.5 Å, b=220.2±1.5 Å, and c=113.1±1.5 Å, and the bond angles: $\alpha=90°$, $\beta=90°$, and $\gamma=120°$.

2. A method for producing a crystal of EGF-EGFR complex as defined in claim 1, comprising the following steps of:

(A) producing crystallizable EGFR by genetic engineering techniques using Lec8 cells (ATCC CRL-1737) transformed with DNA encoding the EGFR;

(B) deglycosylating the EGFR using a glycosidase, followed by purification of the resulting EGFR to obtain crystallizable EGFR:
(C) bringing the crystallizable EGFR into contact with EGF; and
(D) obtaining a crystal of EGF-EGFR complex from a solution containing the EGF-EGFR complex using a precipitating agent.

3. A method for determining the structure coordinates of an epidermal growth factor (EGR)-epidermal growth factor receptor (EGFR) complex (EGF-EGFR complex) comprising the following steps of:
(A) producing a crystal of the EGF-EGFR complex by;
1) producing crystallizable EGFR by genetic engineering techniques using Lec8 cells (ATCC CRL-1737) transformed with DNA encoding the EGFR;
2) deglycosylating the EGFR using a glycosidase, followed by purification of the resulting EGFR to obtain crystallizable EGFR;
3) bringing the crystallizable EGFR into contact with EGF; and
4) obtaining a crystal of EGF-EGFR complex from a solution containing the EGF-EGFR complex using a precipitating agent; and wherein the crystal of the EFG-EGFR complex comprises: the EGF having the amino acid sequence of SEQ ID NO:2 and the EGFR having amino acids 1-619 of SEQ ID NO:1, the crystal being capable of diffracting X-ray at a resolution of 3.3 Å, wherein the crystal has the following characteristics a), b), and c):
a) EGF binds to EGFR at a 1:1 ratio;
b) the EGF-bound EGFRs form a dimer; and
c) the crystal has the space group $P3_121$, the unit cell parameters: a=220.2±1.5 Å, b=220.2±1 5 Å, and c=113.1±1.5 Å, and the bond angles: $\alpha$=90°, $\beta$=90°, and $\gamma$=120°,
(B) subjecting the crystal to x-ray diffraction, and determining the structure coordinates of the crystal by X-ray crystal structure analysis.

4. The method of claim 2, wherein in step (D) the precipitating agent is polyethylene glycol, and wherein the crystal is obtained using a vapor diffusion method under conditions of a pH of 7.0 to 9.0, a protein concentration of between 3 and 15 mg/ml inclusive, and a temperature of 20° C.

5. The method of claim 2, wherein the purification comprises a salting out step.

6. The method of claim 2, wherein the glycosidase is endoglycosidase D or endoglycosidase H, or a mixture thereof.

7. A method for determining the structure coordinates of an epidermal growth factor (EGF)-epidermal growth factor receptor (EGFR) complex (EGF-EGFR complex) comprising the following steps of:
(A) producing a crystal of the EGF-EGFR complex by:
1) producing crystallizable EGFR by genetic engineering techniques using Lec8 cells (ATCC CRL-1737) transformed with DNA encoding the EGFR;
2) deglycosylating the EGFR using a glycosidase, followed by purification of the resulting EGFR to obtain crystallizable EGFR:
3) bringing the crystallizable EGFR into contact with EGF; and
4) obtaining a crystal of EGF-EGFR complex from a solution containing the EGF-EGFR complex using a precipitating agent, wherein the crystal of said EFG-EGFR complex comprises: the EGF having the amino acid sequence of SEQ ID NO:2 and the EGFR having amino acids 1-619 of SEQ ID NO:1, the crystal being capable of diffracting X-ray at a resolution of 3.3 Å, wherein said crystal has the following characteristics a), b), and c):
a) EGF binds to EGFR at a 1:1 ratio;
b) the EGF-bound EGFRs form a dimer; and
c) the crystal has the space group $P3_121$, the unit cell parameters: a=220.2 ±1.5 Å, b=220.2±1 5 Å, and c=113.1±1.5 Å, and the bond angles: $\alpha$=90°, $\beta$=90°, and $\gamma$=120°, wherein said precipitating agent is polyethylene glycol, and wherein the crystal is obtained using a vapor diffusion method under conditions of a pH of 7.0 to 9.0, a protein concentration of between 3 and 15 mg/ml inclusive, and a temperature of 20° C.; and
(B) subjecting the crystal to X-ray diffraction, and determining the structure coordinates of the crystal by X-ray crystal structure analysis.

* * * * *

UNITED STATES PATENT AND TRADEMARK OFFICE
CERTIFICATE OF CORRECTION

PATENT NO. : 7,514,240 B2 Page 1 of 1
APPLICATION NO. : 10/503486
DATED : April 7, 2009
INVENTOR(S) : Shigeyuki Yokoyama et al.

It is certified that error appears in the above-identified patent and that said Letters Patent is hereby corrected as shown below:

On the Title page:

Item (54) should read ~~EGR/EGFR~~ EGF/EGFR COMPLEX

Signed and Sealed this

Sixth Day of October, 2009

David J. Kappos
*Director of the United States Patent and Trademark Office*

UNITED STATES PATENT AND TRADEMARK OFFICE
CERTIFICATE OF CORRECTION

PATENT NO.         : 7,514,240 B2　　　　　　　　　　　　　　　　　　　　　　Page 1 of 1
APPLICATION NO.    : 10/503486
DATED              : April 7, 2009
INVENTOR(S)        : Shigeyuki Yokoyama et al.

It is certified that error appears in the above-identified patent and that said Letters Patent is hereby corrected as shown below:

Title Page, Item (54) and Column 1, line 1, title should read
~~EGR/EGFR~~ EGF/EGFR COMPLEX This certificate supersedes the Certificate of Correction issued October 6, 2009.

Signed and Sealed this

Twenty-seventh Day of October, 2009

David J. Kappos
*Director of the United States Patent and Trademark Office*

SEQUENCE LISTING

```
<160> NUMBER OF SEQ ID NOS: 15

<210> SEQ ID NO 1
<211> LENGTH: 633
<212> TYPE: PRT
<213> ORGANISM: Artificial Sequence
<220> FEATURE:
<223> OTHER INFORMATION: Description of Artificial Sequence: synthetic
      peptide

<400> SEQUENCE: 1

Leu Glu Glu Lys Lys Val Cys Gln Gly Thr Ser Asn Lys Leu Thr Gln
  1               5                  10                  15

Leu Gly Thr Phe Glu Asp His Phe Leu Ser Leu Gln Arg Met Phe Asn
             20                  25                  30

Asn Cys Glu Val Val Leu Gly Asn Leu Glu Ile Thr Tyr Val Gln Arg
         35                  40                  45

Asn Tyr Asp Leu Ser Phe Leu Lys Thr Ile Gln Glu Val Ala Gly Tyr
     50                  55                  60

Val Leu Ile Ala Leu Asn Thr Val Glu Arg Ile Pro Leu Glu Asn Leu
 65                  70                  75                  80

Gln Ile Ile Arg Gly Asn Met Tyr Tyr Glu Asn Ser Tyr Ala Leu Ala
                 85                  90                  95

Val Leu Ser Asn Tyr Asp Ala Asn Lys Thr Gly Leu Lys Glu Leu Pro
            100                 105                 110

Met Arg Asn Leu Gln Glu Ile Leu His Gly Ala Val Arg Phe Ser Asn
        115                 120                 125

Asn Pro Ala Leu Cys Asn Val Glu Ser Ile Gln Trp Arg Asp Ile Val
    130                 135                 140

Ser Ser Asp Phe Leu Ser Asn Met Ser Met Asp Phe Gln Asn His Leu
145                 150                 155                 160

Gly Ser Cys Gln Lys Cys Asp Pro Ser Cys Pro Asn Gly Ser Cys Trp
                165                 170                 175

Gly Ala Gly Glu Glu Asn Cys Gln Lys Leu Thr Lys Ile Ile Cys Ala
            180                 185                 190

Gln Gln Cys Ser Gly Arg Cys Arg Gly Lys Ser Pro Ser Asp Cys Cys
```

-continued

```
            195                 200                 205
His Asn Gln Cys Ala Ala Gly Cys Thr Gly Pro Arg Glu Ser Asp Cys
    210                 215                 220

Leu Val Cys Arg Lys Phe Arg Asp Glu Ala Thr Cys Lys Asp Thr Cys
225                 230                 235                 240

Pro Pro Leu Met Leu Tyr Asn Pro Thr Thr Tyr Gln Met Asp Val Asn
                245                 250                 255

Pro Glu Gly Lys Tyr Ser Phe Gly Ala Thr Cys Val Lys Lys Cys Pro
                260                 265                 270

Arg Asn Tyr Val Val Thr Asp His Gly Ser Cys Val Arg Ala Cys Gly
            275                 280                 285

Ala Asp Ser Tyr Glu Met Glu Glu Asp Gly Val Arg Lys Cys Lys Lys
        290                 295                 300

Cys Glu Gly Pro Cys Arg Lys Val Cys Asn Gly Ile Gly Ile Gly Glu
305                 310                 315                 320

Phe Lys Asp Ser Leu Ser Ile Asn Ala Thr Asn Ile Lys His Phe Lys
                325                 330                 335

Asn Cys Thr Ser Ile Ser Gly Asp Leu His Ile Leu Pro Val Ala Phe
                340                 345                 350

Arg Gly Asp Ser Phe Thr His Thr Pro Pro Leu Asp Pro Gln Glu Leu
                355                 360                 365

Asp Ile Leu Lys Thr Val Lys Glu Ile Thr Gly Phe Leu Leu Ile Gln
        370                 375                 380

Ala Trp Pro Glu Asn Arg Thr Asp Leu His Ala Phe Glu Asn Leu Glu
385                 390                 395                 400

Ile Ile Arg Gly Arg Thr Lys Gln His Gly Gln Phe Ser Leu Ala Val
                405                 410                 415

Val Ser Leu Asn Ile Thr Ser Leu Gly Leu Arg Ser Leu Lys Glu Ile
            420                 425                 430

Ser Asp Gly Asp Val Ile Ile Ser Gly Asn Lys Asn Leu Cys Tyr Ala
        435                 440                 445

Asn Thr Ile Asn Trp Lys Lys Leu Phe Gly Thr Ser Gly Gln Lys Thr
450                 455                 460

Lys Ile Ile Ser Asn Arg Gly Glu Asn Ser Cys Lys Ala Thr Gly Gln
465                 470                 475                 480

Val Cys His Ala Leu Cys Ser Pro Glu Gly Cys Trp Gly Pro Glu Pro
                485                 490                 495

Arg Asp Cys Val Ser Cys Arg Asn Val Ser Arg Gly Arg Glu Cys Val
                500                 505                 510

Asp Lys Cys Asn Leu Leu Glu Gly Glu Pro Arg Glu Phe Val Glu Asn
            515                 520                 525

Ser Glu Cys Ile Gln Cys His Pro Glu Cys Leu Pro Gln Ala Met Asn
        530                 535                 540

Ile Thr Cys Thr Gly Arg Gly Pro Asp Asn Cys Ile Gln Cys Ala His
545                 550                 555                 560

Tyr Ile Asp Gly Pro His Cys Val Lys Thr Cys Pro Ala Gly Val Met
                565                 570                 575

Gly Glu Asn Asn Thr Leu Val Trp Lys Tyr Ala Asp Ala Gly His Val
                580                 585                 590

Cys His Leu Cys His Pro Asn Cys Thr Tyr Gly Cys Thr Gly Pro Gly
            595                 600                 605

Leu Glu Gly Cys Pro Thr Asn Gly Pro Lys Ile Leu Val Pro Arg Gly
        610                 615                 620
```

```
Ser Asp Tyr Lys Asp Asp Asp Lys
625             630

<210> SEQ ID NO 2
<211> LENGTH: 53
<212> TYPE: PRT
<213> ORGANISM: Homo sapiens

<400> SEQUENCE: 2

Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 3
<211> LENGTH: 478
<212> TYPE: PRT
<213> ORGANISM: Homo sapiens

<400> SEQUENCE: 3

Glu Ile Cys Gly Pro Gly Ile Asp Ile Arg Asn Asp Tyr Gln Gln Leu
 1               5                  10                  15

Lys Arg Leu Glu Asn Cys Thr Val Ile Glu Gly Tyr Leu His Ile Leu
            20                  25                  30

Leu Ile Ser Lys Ala Glu Asp Tyr Arg Ser Tyr Arg Phe Pro Lys Leu
        35                  40                  45

Thr Val Ile Thr Glu Tyr Leu Leu Leu Phe Arg Val Ala Gly Leu Glu
    50                  55                  60

Ser Leu Gly Asp Leu Phe Pro Asn Leu Thr Val Ile Arg Gly Trp Lys
65                  70                  75                  80

Leu Phe Tyr Asn Tyr Ala Leu Val Ile Phe Glu Met Thr Asn Leu Lys
                85                  90                  95

Asp Ile Gly Leu Tyr Asn Leu Arg Asn Ile Thr Arg Gly Ala Ile Arg
            100                 105                 110

Ile Glu Lys Asn Ala Asp Leu Cys Tyr Leu Ser Thr Val Asp Trp Ser
        115                 120                 125

Leu Ile Leu Asp Ala Val Ser Asn Asn Tyr Ile Val Gly Asn Lys Pro
    130                 135                 140

Pro Lys Glu Cys Gly Asp Leu Cys Pro Gly Thr Met Glu Glu Lys Pro
145                 150                 155                 160

Met Cys Glu Lys Thr Thr Ile Asn Asn Glu Tyr Asn Tyr Arg Cys Trp
                165                 170                 175

Thr Thr Asn Arg Cys Gln Lys Met Cys Pro Ser Thr Cys Gly Lys Arg
            180                 185                 190

Ala Cys Thr Glu Asn Asn Glu Cys Cys His Pro Glu Cys Leu Gly Ser
        195                 200                 205

Cys Ser Ala Pro Asp Asn Asp Thr Ala Cys Val Ala Cys Arg His Tyr
    210                 215                 220

Tyr Tyr Ala Gly Val Cys Val Pro Ala Cys Pro Pro Asn Thr Tyr Arg
225                 230                 235                 240

Phe Glu Gly Trp Arg Cys Val Asp Arg Asp Phe Cys Ala Asn Ile Leu
                245                 250                 255
```

```
Ser Ala Glu Ser Ser Asp Ser Glu Gly Phe Val Ile His Asp Gly Glu
        260                 265                 270

Cys Met Gln Glu Cys Pro Ser Gly Phe Ile Arg Asn Gly Ser Gln Ser
        275                 280                 285

Met Tyr Cys Ile Pro Cys Glu Gly Pro Cys Pro Lys Val Cys Glu Glu
        290                 295                 300

Glu Lys Lys Thr Lys Thr Ile Asp Ser Val Thr Ser Ala Gln Met Leu
305                 310                 315                 320

Gln Gly Cys Thr Ile Phe Lys Gly Asn Leu Leu Ile Asn Ile Arg Arg
                325                 330                 335

Gly Asn Asn Ile Ala Ser Glu Leu Glu Asn Phe Met Gly Leu Ile Glu
                340                 345                 350

Val Val Thr Gly Tyr Val Lys Ile Arg His Ser His Ala Leu Val Ser
                355                 360                 365

Leu Ser Phe Leu Lys Asn Leu Arg Leu Ile Leu Gly Glu Glu Gln Leu
        370                 375                 380

Glu Gly Asn Tyr Ser Phe Tyr Val Leu Asp Asn Gln Asn Leu Gln Gln
385                 390                 395                 400

Leu Trp Asp Trp Asp His Arg Asn Leu Thr Ile Lys Ala Gly Lys Met
                405                 410                 415

Tyr Phe Ala Phe Asn Pro Lys Leu Cys Val Ser Glu Ile Tyr Arg Met
                420                 425                 430

Glu Glu Val Thr Gly Thr Lys Gly Arg Gln Ser Lys Gly Asp Ile Asn
                435                 440                 445

Thr Arg Asn Asn Gly Glu Arg Ala Ser Cys Glu Ser Asp Val Asp Asp
        450                 455                 460

Asp Asp Lys Glu Gln Lys Leu Ile Ser Glu Glu Asp Leu Asn
465                 470                 475

<210> SEQ ID NO 4
<211> LENGTH: 1382
<212> TYPE: PRT
<213> ORGANISM: Homo sapiens

<400> SEQUENCE: 4

Met Gly Thr Gly Gly Arg Arg Gly Ala Ala Ala Ala Pro Leu Leu Val
 1               5                  10                  15

Ala Val Ala Ala Leu Leu Leu Gly Ala Ala Gly His Leu Tyr Pro Gly
                20                  25                  30

Glu Val Cys Pro Gly Met Asp Ile Arg Asn Asn Leu Thr Arg Leu His
            35                  40                  45

Glu Leu Glu Asn Cys Ser Val Ile Glu Gly His Leu Gln Ile Leu Leu
        50                  55                  60

Met Phe Lys Thr Arg Pro Glu Asp Phe Arg Asp Leu Ser Phe Pro Lys
65                  70                  75                  80

Leu Ile Met Ile Thr Asp Tyr Leu Leu Leu Phe Arg Val Tyr Gly Leu
                85                  90                  95

Glu Ser Leu Lys Asp Leu Phe Pro Asn Leu Thr Val Ile Arg Gly Ser
            100                 105                 110

Arg Leu Phe Phe Asn Tyr Ala Leu Val Ile Phe Glu Met Val His Leu
        115                 120                 125

Lys Glu Leu Gly Leu Tyr Asn Leu Met Asn Ile Thr Arg Gly Ser Val
    130                 135                 140

Arg Ile Glu Lys Asn Asn Glu Leu Cys Tyr Leu Ala Thr Ile Asp Trp
```

-continued

```
            145                 150                 155                 160
Ser Arg Ile Leu Asp Ser Val Glu Asp Asn His Ile Val Leu Asn Lys
                165                 170                 175
Asp Asp Asn Glu Glu Cys Gly Asp Ile Cys Pro Gly Thr Ala Lys Gly
            180                 185                 190
Lys Thr Asn Cys Pro Ala Thr Val Ile Asn Gly Gln Phe Val Glu Arg
            195                 200                 205
Cys Trp Thr His Ser His Cys Gln Lys Val Cys Pro Thr Ile Cys Lys
            210                 215                 220
Ser His Gly Cys Thr Ala Glu Gly Leu Cys Cys His Ser Glu Cys Leu
225                 230                 235                 240
Gly Asn Cys Ser Gln Pro Asp Asp Pro Thr Lys Cys Val Ala Cys Arg
                245                 250                 255
Asn Phe Tyr Leu Asp Gly Arg Cys Val Glu Thr Cys Pro Pro Pro Tyr
            260                 265                 270
Tyr His Phe Gln Asp Trp Arg Cys Val Asn Phe Ser Phe Cys Gln Asp
            275                 280                 285
Leu His His Lys Cys Lys Asn Ser Arg Arg Gln Gly Cys His Gln Tyr
            290                 295                 300
Val Ile His Asn Asn Lys Cys Ile Pro Glu Cys Pro Ser Gly Tyr Thr
305                 310                 315                 320
Met Asn Ser Ser Asn Leu Leu Cys Thr Pro Cys Leu Gly Pro Cys Pro
                325                 330                 335
Lys Val Cys His Leu Leu Glu Gly Glu Lys Thr Ile Asp Ser Val Thr
            340                 345                 350
Ser Ala Gln Glu Leu Arg Gly Cys Thr Val Ile Asn Gly Ser Leu Ile
            355                 360                 365
Ile Asn Ile Arg Gly Gly Asn Asn Leu Ala Ala Glu Leu Glu Ala Asn
            370                 375                 380
Leu Gly Leu Ile Glu Glu Ile Ser Gly Tyr Leu Lys Ile Arg Arg Ser
385                 390                 395                 400
Tyr Ala Leu Val Ser Leu Ser Phe Phe Arg Lys Leu Arg Leu Ile Arg
                405                 410                 415
Gly Glu Thr Leu Glu Ile Gly Asn Tyr Ser Phe Tyr Ala Leu Asp Asn
            420                 425                 430
Gln Asn Leu Arg Gln Leu Trp Asp Trp Ser Lys His Asn Leu Thr Thr
            435                 440                 445
Thr Gln Gly Lys Leu Phe Phe His Tyr Asn Pro Lys Leu Cys Leu Ser
            450                 455                 460
Glu Ile His Lys Met Glu Glu Val Ser Gly Thr Lys Gly Arg Gln Glu
465                 470                 475                 480
Arg Asn Asp Ile Ala Leu Lys Thr Asn Gly Asp Lys Ala Ser Cys Glu
                485                 490                 495
Asn Glu Leu Leu Lys Phe Ser Tyr Ile Arg Thr Ser Phe Asp Lys Ile
            500                 505                 510
Leu Leu Arg Trp Glu Pro Tyr Trp Pro Pro Asp Phe Arg Asp Leu Leu
            515                 520                 525
Gly Phe Met Leu Phe Tyr Lys Glu Ala Pro Tyr Gln Asn Val Thr Glu
            530                 535                 540
Phe Asp Gly Gln Asp Ala Cys Gly Ser Asn Ser Trp Thr Val Val Asp
545                 550                 555                 560
Ile Asp Pro Pro Leu Arg Ser Asn Asp Pro Lys Ser Gln Asn His Pro
                565                 570                 575
```

```
Gly Trp Leu Met Arg Gly Leu Lys Pro Trp Thr Gln Tyr Ala Ile Phe
            580                 585                 590

Val Lys Thr Leu Val Thr Phe Ser Asp Glu Arg Arg Thr Tyr Gly Ala
            595                 600                 605

Lys Ser Asp Ile Ile Tyr Val Gln Thr Asp Ala Thr Asn Pro Ser Val
            610                 615                 620

Pro Leu Asp Pro Ile Ser Val Ser Asn Ser Ser Gln Ile Ile Leu
625                 630                 635                 640

Lys Trp Lys Pro Pro Ser Asp Pro Asn Gly Asn Ile Thr His Tyr Leu
                645                 650                 655

Val Phe Trp Glu Arg Gln Ala Glu Asp Ser Glu Leu Phe Glu Leu Asp
            660                 665                 670

Tyr Cys Leu Lys Gly Leu Lys Leu Pro Ser Arg Thr Trp Ser Pro Pro
            675                 680                 685

Phe Glu Ser Glu Asp Ser Gln Lys His Asn Gln Ser Glu Tyr Glu Asp
            690                 695                 700

Ser Ala Gly Glu Cys Cys Ser Cys Pro Lys Thr Asp Ser Gln Ile Leu
705                 710                 715                 720

Lys Glu Leu Glu Glu Ser Ser Phe Arg Lys Thr Phe Glu Asp Tyr Leu
                725                 730                 735

His Asn Val Val Phe Val Pro Arg Lys Thr Ser Ser Gly Thr Gly Ala
            740                 745                 750

Glu Asp Pro Arg Pro Ser Arg Lys Arg Arg Ser Leu Gly Asp Val Gly
            755                 760                 765

Asn Val Thr Val Ala Val Pro Thr Val Ala Ala Phe Pro Asn Thr Ser
            770                 775                 780

Ser Thr Ser Val Pro Thr Ser Pro Glu Glu His Arg Pro Phe Glu Lys
785                 790                 795                 800

Val Val Asn Lys Glu Ser Leu Val Ile Ser Gly Leu Arg His Phe Thr
                805                 810                 815

Gly Tyr Arg Ile Glu Leu Gln Ala Cys Asn Gln Asp Thr Pro Glu Glu
            820                 825                 830

Arg Cys Ser Val Ala Ala Tyr Val Ser Ala Arg Thr Met Pro Glu Ala
            835                 840                 845

Lys Ala Asp Asp Ile Val Gly Pro Val Thr His Glu Ile Phe Glu Asn
            850                 855                 860

Asn Val Val His Leu Met Trp Gln Glu Pro Lys Glu Pro Asn Gly Leu
865                 870                 875                 880

Ile Val Leu Tyr Glu Val Ser Tyr Arg Arg Tyr Gly Asp Glu Glu Leu
                885                 890                 895

His Leu Cys Val Ser Arg Lys His Phe Ala Leu Glu Arg Gly Cys Arg
            900                 905                 910

Leu Arg Gly Leu Ser Pro Gly Asn Tyr Ser Val Arg Ile Arg Ala Thr
            915                 920                 925

Ser Leu Ala Gly Asn Gly Ser Trp Thr Glu Pro Thr Tyr Phe Tyr Val
            930                 935                 940

Thr Asp Tyr Leu Asp Val Pro Ser Asn Ile Ala Lys Ile Ile Ile Gly
945                 950                 955                 960

Pro Leu Ile Phe Val Phe Leu Phe Ser Val Val Ile Gly Ser Ile Tyr
                965                 970                 975

Leu Phe Leu Arg Lys Arg Gln Pro Asp Gly Pro Leu Gly Pro Leu Tyr
            980                 985                 990
```

-continued

Ala Ser Ser Asn Pro Glu Tyr Leu Ser Ala Ser Asp Val Phe Pro Cys
        995                 1000                1005

Ser Val Tyr Val Pro Asp Glu Trp Glu Val Ser Arg Glu Lys Ile Thr
1010                1015                1020

Leu Leu Arg Glu Leu Gly Gln Gly Ser Phe Gly Met Val Tyr Glu Gly
1025                1030                1035                1040

Asn Ala Arg Asp Ile Ile Lys Gly Glu Ala Glu Thr Arg Val Ala Val
            1045                1050                1055

Lys Thr Val Asn Glu Ser Ala Ser Leu Arg Glu Arg Ile Glu Phe Leu
        1060                1065                1070

Asn Glu Ala Ser Val Met Lys Gly Phe Thr Cys His His Val Val Arg
    1075                1080                1085

Leu Leu Gly Val Val Ser Lys Gly Gln Pro Thr Leu Val Val Met Glu
1090                1095                1100

Leu Met Ala His Gly Asp Leu Lys Ser Tyr Leu Arg Ser Leu Arg Pro
1105                1110                1115                1120

Glu Ala Glu Asn Asn Pro Gly Arg Pro Pro Thr Leu Gln Glu Met
            1125                1130                1135

Ile Gln Met Ala Ala Glu Ile Ala Asp Gly Met Ala Tyr Leu Asn Ala
            1140                1145                1150

Lys Lys Phe Val His Arg Asp Leu Ala Ala Arg Asn Cys Met Val Ala
        1155                1160                1165

His Asp Phe Thr Val Lys Ile Gly Asp Phe Gly Met Thr Arg Asp Ile
    1170                1175                1180

Tyr Glu Thr Asp Tyr Tyr Arg Lys Gly Gly Lys Gly Leu Leu Pro Val
1185                1190                1195                1200

Arg Trp Met Ala Pro Glu Ser Leu Lys Asp Gly Val Phe Thr Thr Ser
            1205                1210                1215

Ser Asp Met Trp Ser Phe Gly Val Val Leu Trp Glu Ile Thr Ser Leu
        1220                1225                1230

Ala Glu Gln Pro Tyr Gln Gly Leu Ser Asn Glu Gln Val Leu Lys Phe
    1235                1240                1245

Val Met Asp Gly Gly Tyr Leu Asp Gln Pro Asp Asn Cys Pro Glu Arg
1250                1255                1260

Val Thr Asp Leu Met Arg Met Cys Trp Gln Phe Asn Pro Lys Met Arg
1265                1270                1275                1280

Pro Thr Phe Leu Glu Ile Val Asn Leu Leu Lys Asp Asp Leu His Pro
            1285                1290                1295

Ser Phe Pro Glu Val Ser Phe Phe His Ser Glu Glu Asn Lys Ala Pro
        1300                1305                1310

Glu Ser Glu Glu Leu Glu Met Glu Phe Glu Asp Met Glu Asn Val Pro
    1315                1320                1325

Leu Asp Arg Ser Ser His Cys Gln Arg Glu Glu Ala Gly Gly Arg Asp
1330                1335                1340

Gly Gly Ser Ser Leu Gly Phe Lys Arg Ser Tyr Glu Glu His Ile Pro
1345                1350                1355                1360

Tyr Thr His Met Asn Gly Gly Lys Lys Asn Gly Arg Ile Leu Thr Leu
            1365                1370                1375

Pro Arg Ser Asn Pro Ser
            1380

<210> SEQ ID NO 5
<211> LENGTH: 1255
<212> TYPE: PRT

<213> ORGANISM: Homo sapiens

<400> SEQUENCE: 5

| | | | | | | | | | | | | | | |
|---|---|---|---|---|---|---|---|---|---|---|---|---|---|---|
| Met | Glu | Leu | Ala | Ala | Leu | Cys | Arg | Trp | Gly | Leu | Leu | Ala | Leu | Leu |
| 1 | | | | 5 | | | | | 10 | | | | | 15 |
| Pro | Pro | Gly | Ala | Ala | Ser | Thr | Gln | Val | Cys | Thr | Gly | Thr | Asp | Met | Lys |
| | | | 20 | | | | | 25 | | | | | 30 | | |
| Leu | Arg | Leu | Pro | Ala | Ser | Pro | Glu | Thr | His | Leu | Asp | Met | Leu | Arg | His |
| | 35 | | | | | 40 | | | | | 45 | | | | |
| Leu | Tyr | Gln | Gly | Cys | Gln | Val | Val | Gln | Gly | Asn | Leu | Glu | Leu | Thr | Tyr |
| 50 | | | | | 55 | | | | | 60 | | | | | |
| Leu | Pro | Thr | Asn | Ala | Ser | Leu | Ser | Phe | Leu | Gln | Asp | Ile | Gln | Glu | Val |
| 65 | | | | 70 | | | | | 75 | | | | | 80 | |
| Gln | Gly | Tyr | Val | Leu | Ile | Ala | His | Asn | Gln | Val | Arg | Gln | Val | Pro | Leu |
| | | | | 85 | | | | | 90 | | | | | 95 | |
| Gln | Arg | Leu | Arg | Ile | Val | Arg | Gly | Thr | Gln | Leu | Phe | Glu | Asp | Asn | Tyr |
| | | | 100 | | | | | 105 | | | | | 110 | | |
| Ala | Leu | Ala | Val | Leu | Asp | Asn | Gly | Asp | Pro | Leu | Asn | Asn | Thr | Thr | Pro |
| | | 115 | | | | | 120 | | | | | 125 | | | |
| Val | Thr | Gly | Ala | Ser | Pro | Gly | Gly | Leu | Arg | Glu | Leu | Gln | Leu | Arg | Ser |
| 130 | | | | | 135 | | | | | 140 | | | | | |
| Leu | Thr | Glu | Ile | Leu | Lys | Gly | Gly | Val | Leu | Ile | Gln | Arg | Asn | Pro | Gln |
| 145 | | | | | 150 | | | | | 155 | | | | | 160 |
| Leu | Cys | Tyr | Gln | Asp | Thr | Ile | Leu | Trp | Lys | Asp | Ile | Phe | His | Lys | Asn |
| | | | | 165 | | | | | 170 | | | | | 175 | |
| Asn | Gln | Leu | Ala | Leu | Thr | Leu | Ile | Asp | Thr | Asn | Arg | Ser | Arg | Ala | Cys |
| | | | 180 | | | | | 185 | | | | | 190 | | |
| His | Pro | Cys | Ser | Pro | Met | Cys | Lys | Gly | Ser | Arg | Cys | Trp | Gly | Glu | Ser |
| | | 195 | | | | | 200 | | | | | 205 | | | |
| Ser | Glu | Asp | Cys | Gln | Ser | Leu | Thr | Arg | Thr | Val | Cys | Ala | Gly | Gly | Cys |
| | 210 | | | | | 215 | | | | | 220 | | | | |
| Ala | Arg | Cys | Lys | Gly | Pro | Leu | Pro | Thr | Asp | Cys | Cys | His | Glu | Gln | Cys |
| 225 | | | | | 230 | | | | | 235 | | | | | 240 |
| Ala | Ala | Gly | Cys | Thr | Gly | Pro | Lys | His | Ser | Asp | Cys | Leu | Ala | Cys | Leu |
| | | | | 245 | | | | | 250 | | | | | 255 | |
| His | Phe | Asn | His | Ser | Gly | Ile | Cys | Glu | Leu | His | Cys | Pro | Ala | Leu | Val |
| | | | 260 | | | | | 265 | | | | | 270 | | |
| Thr | Tyr | Asn | Thr | Asp | Thr | Phe | Glu | Ser | Met | Pro | Asn | Pro | Glu | Gly | Arg |
| | | 275 | | | | | 280 | | | | | 285 | | | |
| Tyr | Thr | Phe | Gly | Ala | Ser | Cys | Val | Thr | Ala | Cys | Pro | Tyr | Asn | Tyr | Leu |
| | 290 | | | | | 295 | | | | | 300 | | | | |
| Ser | Thr | Asp | Val | Gly | Ser | Cys | Thr | Leu | Val | Cys | Pro | Leu | His | Asn | Gln |
| 305 | | | | | 310 | | | | | 315 | | | | | 320 |
| Glu | Val | Thr | Ala | Glu | Asp | Gly | Thr | Gln | Arg | Cys | Glu | Lys | Cys | Ser | Lys |
| | | | | 325 | | | | | 330 | | | | | 335 | |
| Pro | Cys | Ala | Arg | Val | Cys | Tyr | Gly | Leu | Gly | Met | Glu | His | Leu | Arg | Glu |
| | | | 340 | | | | | 345 | | | | | 350 | | |
| Val | Arg | Ala | Val | Thr | Ser | Ala | Asn | Ile | Gln | Glu | Phe | Ala | Gly | Cys | Lys |
| | | 355 | | | | | 360 | | | | | 365 | | | |
| Lys | Ile | Phe | Gly | Ser | Leu | Ala | Phe | Leu | Pro | Glu | Ser | Phe | Asp | Gly | Asp |
| | 370 | | | | | 375 | | | | | 380 | | | | |
| Pro | Ala | Ser | Asn | Thr | Ala | Pro | Leu | Gln | Pro | Glu | Gln | Leu | Gln | Val | Phe |
| 385 | | | | | 390 | | | | | 395 | | | | | 400 |

-continued

```
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Val Ser
                645                 650                 655
Ala Val Val Gly Ile Leu Leu Val Val Leu Gly Val Val Phe Gly
            660                 665                 670
Ile Leu Ile Lys Arg Arg Gln Gln Lys Ile Arg Lys Tyr Thr Met Arg
        675                 680                 685
Arg Leu Leu Gln Glu Thr Glu Leu Val Glu Pro Leu Thr Pro Ser Gly
    690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
        755                 760                 765
Asp Glu Ala Tyr Val Met Ala Gly Val Gly Ser Pro Tyr Val Ser Arg
    770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                805                 810                 815
Leu Gly Ser Gln Asp Leu Leu Asn Trp Cys Met Gln Ile Ala Lys Gly
```

-continued

```
                820                 825                 830
Met Ser Tyr Leu Glu Asp Val Arg Leu Val His Arg Asp Leu Ala Ala
            835                 840                 845
Arg Asn Val Leu Val Lys Ser Pro Asn His Val Lys Ile Thr Asp Phe
        850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Val Trp Ser Tyr Gly Val Thr Val
            900                 905                 910
Trp Glu Leu Met Thr Phe Gly Ala Lys Pro Tyr Asp Gly Ile Pro Ala
        915                 920                 925
Arg Glu Ile Pro Asp Leu Leu Glu Lys Gly Glu Arg Leu Pro Gln Pro
    930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
            980                 985                 990
Asp Leu Gly Pro Ala Ser Pro Leu Asp Ser Thr Phe Tyr Arg Ser Leu
        995                 1000                1005
Leu Glu Asp Asp Asp Met Gly Asp Leu Val Asp Ala Glu Glu Tyr Leu
    1010                1015                1020
Val Pro Gln Gln Gly Phe Phe Cys Pro Asp Pro Ala Pro Gly Ala Gly
1025                1030                1035                1040
Gly Met Val His His Arg His Arg Ser Ser Ser Thr Arg Ser Gly Gly
                1045                1050                1055
Gly Asp Leu Thr Leu Gly Leu Glu Pro Ser Glu Glu Ala Pro Arg
            1060                1065                1070
Ser Pro Leu Ala Pro Ser Glu Gly Ala Gly Ser Asp Val Phe Asp Gly
        1075                1080                1085
Asp Leu Gly Met Gly Ala Ala Lys Gly Leu Gln Ser Leu Pro Thr His
    1090                1095                1100
Asp Pro Ser Pro Leu Gln Arg Tyr Ser Glu Asp Pro Thr Val Pro Leu
1105                1110                1115                1120
Pro Ser Glu Thr Asp Gly Tyr Val Ala Pro Leu Thr Cys Ser Pro Gln
                1125                1130                1135
Pro Glu Tyr Val Asn Gln Pro Asp Val Arg Pro Gln Pro Pro Ser Pro
            1140                1145                1150
Arg Glu Gly Pro Leu Pro Ala Ala Arg Pro Ala Gly Ala Thr Leu Glu
        1155                1160                1165
Arg Ala Lys Thr Leu Ser Pro Gly Lys Asn Gly Val Val Lys Asp Val
    1170                1175                1180
Phe Ala Phe Gly Gly Ala Val Glu Asn Pro Glu Tyr Leu Thr Pro Gln
1185                1190                1195                1200
Gly Gly Ala Ala Pro Gln Pro His Pro Pro Ala Phe Ser Pro Ala
                1205                1210                1215
Phe Asp Asn Leu Tyr Tyr Trp Asp Gln Asp Pro Pro Glu Arg Gly Ala
            1220                1225                1230
Pro Pro Ser Thr Phe Lys Gly Thr Pro Thr Ala Glu Asn Pro Glu Tyr
        1235                1240                1245
```

Leu Gly Leu Asp Val Pro Val
    1250            1255

<210> SEQ ID NO 6
<211> LENGTH: 1342
<212> TYPE: PRT
<213> ORGANISM: Homo sapiens

<400> SEQUENCE: 6

Met Arg Ala Asn Asp Ala Leu Gln Val Leu Gly Leu Phe Ser Leu
  1               5                  10                  15

Ala Arg Gly Ser Glu Val Gly Asn Ser Gln Ala Val Cys Pro Gly Thr
                 20                  25                  30

Leu Asn Gly Leu Ser Val Thr Gly Asp Ala Glu Asn Gln Tyr Gln Thr
             35                  40                  45

Leu Tyr Lys Leu Tyr Glu Arg Cys Glu Val Val Met Gly Asn Leu Glu
 50                  55                  60

Ile Val Leu Thr Gly His Asn Ala Asp Leu Ser Phe Leu Gln Trp Ile
 65                  70                  75                  80

Arg Glu Val Thr Gly Tyr Val Leu Val Ala Met Asn Glu Phe Ser Thr
                 85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
                165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
        195                 200                 205

Ile Cys Ala Pro Gln Cys Asn Gly His Cys Phe Gly Pro Asn Pro Asn
210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
                245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
                325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu

-continued

```
              355                 360                 365
Asn Gly Asp Pro Trp His Lys Ile Pro Ala Leu Asp Pro Glu Lys Leu
        370                 375                 380
Asn Val Phe Arg Thr Val Arg Glu Ile Thr Gly Tyr Leu Asn Ile Gln
385                 390                 395                 400
Ser Trp Pro Pro His Met His Asn Phe Ser Val Phe Ser Asn Leu Thr
                405                 410                 415
Thr Ile Gly Gly Arg Ser Leu Tyr Asn Arg Gly Phe Ser Leu Leu Ile
                420                 425                 430
Met Lys Asn Leu Asn Val Thr Ser Leu Gly Phe Arg Ser Leu Lys Glu
            435                 440                 445
Ile Ser Ala Gly Arg Ile Tyr Ile Ser Ala Asn Arg Gln Leu Cys Tyr
        450                 455                 460
His His Ser Leu Asn Trp Thr Lys Val Leu Arg Gly Pro Thr Glu Glu
465                 470                 475                 480
Arg Leu Asp Ile Lys His Asn Arg Pro Arg Arg Asp Cys Val Ala Glu
                485                 490                 495
Gly Lys Val Cys Asp Pro Leu Cys Ser Ser Gly Gly Cys Trp Gly Pro
                500                 505                 510
Gly Pro Gly Gln Cys Leu Ser Cys Arg Asn Tyr Ser Arg Gly Gly Val
            515                 520                 525
Cys Val Thr His Cys Asn Phe Leu Asn Gly Glu Pro Arg Glu Phe Ala
        530                 535                 540
His Glu Ala Glu Cys Phe Ser Cys His Pro Glu Cys Gln Pro Met Glu
545                 550                 555                 560
Gly Thr Ala Thr Cys Asn Gly Ser Gly Ser Asp Thr Cys Ala Gln Cys
                565                 570                 575
Ala His Phe Arg Asp Gly Pro His Cys Val Ser Ser Cys Pro His Gly
                580                 585                 590
Val Leu Gly Ala Lys Gly Pro Ile Tyr Lys Tyr Pro Asp Val Gln Asn
            595                 600                 605
Glu Cys Arg Pro Cys His Glu Asn Cys Thr Gln Gly Cys Lys Gly Pro
        610                 615                 620
Glu Leu Gln Asp Cys Leu Gly Gln Thr Leu Val Leu Ile Gly Lys Thr
625                 630                 635                 640
His Leu Thr Met Ala Leu Thr Val Ile Ala Gly Leu Val Val Ile Phe
                645                 650                 655
Met Met Leu Gly Gly Thr Phe Leu Tyr Trp Arg Gly Arg Arg Ile Gln
                660                 665                 670
Asn Lys Arg Ala Met Arg Arg Tyr Leu Glu Arg Gly Glu Ser Ile Glu
            675                 680                 685
Pro Leu Asp Pro Ser Glu Lys Ala Asn Lys Val Leu Ala Arg Ile Phe
        690                 695                 700
Lys Glu Thr Glu Leu Arg Lys Leu Lys Val Leu Gly Ser Gly Val Phe
705                 710                 715                 720
Gly Thr Val His Lys Gly Val Trp Ile Pro Glu Gly Glu Ser Ile Lys
                725                 730                 735
Ile Pro Val Cys Ile Lys Val Ile Glu Asp Lys Ser Gly Arg Gln Ser
                740                 745                 750
Phe Gln Ala Val Thr Asp His Met Leu Ala Ile Gly Ser Leu Asp His
            755                 760                 765
Ala His Ile Val Arg Leu Leu Gly Leu Cys Pro Gly Ser Ser Leu Gln
        770                 775                 780
```

-continued

```
Leu Val Thr Gln Tyr Leu Pro Leu Gly Ser Leu Leu Asp His Val Arg
785                 790                 795                 800

Gln His Arg Gly Ala Leu Gly Pro Gln Leu Leu Leu Asn Trp Gly Val
                805                 810                 815

Gln Ile Ala Lys Gly Met Tyr Tyr Leu Glu Glu His Gly Met Val His
                820                 825                 830

Arg Asn Leu Ala Ala Arg Asn Val Leu Leu Lys Ser Pro Ser Gln Val
                835                 840                 845

Gln Val Ala Asp Phe Gly Val Ala Asp Leu Leu Pro Pro Asp Asp Lys
            850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
            915                 920                 925

Arg Leu Ala Gln Pro Gln Ile Cys Thr Ile Asp Val Tyr Met Val Met
930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu Glu Glu Val Glu Leu Glu Pro Glu
            995                 1000                1005

Leu Asp Leu Asp Leu Asp Leu Glu Ala Glu Glu Asp Asn Leu Ala Thr
    1010                1015                1020

Thr Thr Leu Gly Ser Ala Leu Ser Leu Pro Val Gly Thr Leu Asn Arg
1025                1030                1035                1040

Pro Arg Gly Ser Gln Ser Leu Leu Ser Pro Ser Ser Gly Tyr Met Pro
                1045                1050                1055

Met Asn Gln Gly Asn Leu Gly Glu Ser Cys Gln Glu Ser Ala Val Ser
            1060                1065                1070

Gly Ser Ser Glu Arg Cys Pro Arg Pro Val Ser Leu His Pro Met Pro
        1075                1080                1085

Arg Gly Cys Leu Ala Ser Glu Ser Ser Glu Gly His Val Thr Gly Ser
    1090                1095                1100

Glu Ala Glu Leu Gln Glu Lys Val Ser Met Cys Arg Ser Arg Ser Arg
1105                1110                1115                1120

Ser Arg Ser Pro Arg Pro Arg Gly Asp Ser Ala Tyr His Ser Gln Arg
                1125                1130                1135

His Ser Leu Leu Thr Pro Val Thr Pro Leu Ser Pro Pro Gly Leu Glu
            1140                1145                1150

Glu Glu Asp Val Asn Gly Tyr Val Met Pro Asp Thr His Leu Lys Gly
        1155                1160                1165

Thr Pro Ser Ser Arg Glu Gly Thr Leu Ser Ser Val Gly Leu Ser Ser
    1170                1175                1180

Val Leu Gly Thr Glu Glu Glu Asp Glu Asp Glu Glu Tyr Glu Tyr Met
1185                1190                1195                1200
```

-continued

```
Asn Arg Arg Arg Arg His Ser Pro Pro His Pro Pro Arg Pro Ser Ser
            1205                1210                1215

Leu Glu Glu Leu Gly Tyr Glu Tyr Met Asp Val Gly Ser Asp Leu Ser
        1220                1225                1230

Ala Ser Leu Gly Ser Thr Gln Ser Cys Pro Leu His Pro Val Pro Ile
    1235                1240                1245

Met Pro Thr Ala Gly Thr Thr Pro Asp Glu Asp Tyr Glu Tyr Met Asn
1250                1255                1260

Arg Gln Arg Asp Gly Gly Pro Gly Gly Asp Tyr Ala Ala Met Gly
1265                1270                1275                1280

Ala Cys Pro Ala Ser Glu Gln Gly Tyr Glu Glu Met Arg Ala Phe Gln
            1285                1290                1295

Gly Pro Gly His Gln Ala Pro His Val His Tyr Ala Arg Leu Lys Thr
        1300                1305                1310

Leu Arg Ser Leu Glu Ala Thr Asp Ser Ala Phe Asp Asn Pro Asp Tyr
    1315                1320                1325

Trp His Ser Arg Leu Phe Pro Lys Ala Asn Ala Gln Arg Thr
1330                1335                1340

<210> SEQ ID NO 7
<211> LENGTH: 1308
<212> TYPE: PRT
<213> ORGANISM: Homo sapiens

<400> SEQUENCE: 7

Met Lys Pro Ala Thr Gly Leu Trp Val Trp Val Ser Leu Leu Val Ala
1               5                   10                  15

Ala Gly Thr Val Gln Pro Ser Asp Ser Gln Ser Val Cys Ala Gly Thr
            20                  25                  30

Glu Asn Lys Leu Ser Ser Leu Ser Asp Leu Glu Gln Gln Tyr Arg Ala
        35                  40                  45

Leu Arg Lys Tyr Tyr Glu Asn Cys Glu Val Val Met Gly Asn Leu Glu
    50                  55                  60

Ile Thr Ser Ile Glu His Asn Arg Asp Leu Ser Phe Leu Arg Ser Val
65                  70                  75                  80

Arg Glu Val Thr Gly Tyr Val Leu Val Ala Leu Asn Gln Phe Arg Tyr
                85                  90                  95

Leu Pro Leu Glu Asn Leu Arg Ile Ile Arg Gly Thr Lys Leu Tyr Glu
            100                 105                 110

Asp Arg Tyr Ala Leu Ala Ile Phe Leu Asn Tyr Arg Lys Asp Gly Asn
        115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240
```

-continued

```
Pro Lys Asp Thr Asp Cys Phe Ala Cys Met Asn Phe Asn Asp Ser Gly
            245                 250                 255

Ala Cys Val Thr Gln Cys Pro Gln Thr Phe Val Tyr Asn Pro Thr Thr
        260                 265                 270

Phe Gln Leu Glu His Asn Phe Asn Ala Lys Tyr Thr Tyr Gly Ala Phe
    275                 280                 285

Cys Val Lys Lys Cys Pro His Asn Phe Val Val Asp Ser Ser Ser Cys
290                 295                 300

Val Arg Ala Cys Pro Ser Ser Lys Met Glu Val Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
            340                 345                 350

Ile Asp Lys Phe Ile Asn Cys Thr Lys Ile Asn Gly Asn Leu Ile Phe
        355                 360                 365

Leu Val Thr Gly Ile His Gly Asp Pro Tyr Asn Ala Ile Glu Ala Ile
    370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
            420                 425                 430

Ser Leu Leu Ile Leu Lys Gln Gln Gly Ile Thr Ser Leu Gln Phe Gln
        435                 440                 445

Ser Leu Lys Glu Ile Ser Ala Gly Asn Ile Tyr Ile Thr Asp Asn Ser
    450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
            500                 505                 510

Trp Gly Pro Gly Pro Asp Gln Cys Leu Ser Cys Arg Arg Phe Ser Arg
        515                 520                 525

Gly Arg Ile Cys Ile Glu Ser Cys Asn Leu Tyr Asp Gly Glu Phe Arg
    530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
                565                 570                 575

Cys Thr Lys Cys Ser His Phe Lys Asp Gly Pro Asn Cys Val Glu Lys
            580                 585                 590

Cys Pro Asp Gly Leu Gln Gly Ala Asn Ser Phe Ile Phe Lys Tyr Ala
        595                 600                 605

Asp Pro Asp Arg Glu Cys His Pro Cys His Pro Asn Cys Thr Gln Gly
    610                 615                 620

Cys Asn Gly Pro Thr Ser His Asp Cys Ile Tyr Tyr Pro Trp Thr Gly
625                 630                 635                 640

His Ser Thr Leu Pro Gln His Ala Arg Thr Pro Leu Ile Ala Ala Gly
                645                 650                 655
```

```
Val Ile Gly Gly Leu Phe Ile Leu Val Ile Gly Leu Thr Phe Ala
            660                 665                 670

Val Tyr Val Arg Arg Lys Ser Ile Lys Lys Arg Ala Leu Arg Arg
            675                 680                 685

Phe Leu Glu Thr Glu Leu Val Glu Pro Leu Thr Pro Ser Gly Thr Ala
            690                 695                 700

Pro Asn Gln Ala Gln Leu Arg Ile Leu Lys Glu Thr Glu Leu Lys Arg
705                 710                 715                 720

Val Lys Val Leu Gly Ser Gly Ala Phe Gly Thr Val Tyr Lys Gly Ile
                    725                 730                 735

Trp Val Pro Glu Gly Glu Thr Val Lys Ile Pro Val Ala Ile Lys Ile
                    740                 745                 750

Leu Asn Glu Thr Thr Gly Pro Lys Ala Asn Val Glu Phe Met Asp Glu
                    755                 760                 765

Ala Leu Ile Met Ala Ser Met Asp His Pro His Leu Val Arg Leu Leu
770                 775                 780

Gly Val Cys Leu Ser Pro Thr Ile Gln Leu Val Thr Gln Leu Met Pro
785                 790                 795                 800

His Gly Cys Leu Leu Glu Tyr Val His Glu His Lys Asp Asn Ile Gly
                    805                 810                 815

Ser Gln Leu Leu Leu Asn Trp Cys Val Gln Ile Ala Lys Gly Met Met
                    820                 825                 830

Tyr Leu Glu Glu Arg Arg Leu Val His Arg Asp Leu Ala Ala Arg Asn
                    835                 840                 845

Val Leu Val Lys Ser Pro Asn His Val Lys Ile Thr Asp Phe Gly Leu
850                 855                 860

Ala Arg Leu Leu Glu Gly Asp Glu Lys Glu Tyr Asn Ala Asp Gly Gly
865                 870                 875                 880

Lys Met Pro Ile Lys Trp Met Ala Leu Glu Cys Ile His Tyr Arg Lys
                    885                 890                 895

Phe Thr His Gln Ser Asp Val Trp Ser Tyr Gly Val Thr Ile Trp Glu
                    900                 905                 910

Leu Met Thr Phe Gly Gly Lys Pro Tyr Asp Gly Ile Pro Thr Arg Glu
                    915                 920                 925

Ile Pro Asp Leu Leu Glu Lys Gly Glu Arg Leu Pro Gln Pro Pro Ile
930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
                    965                 970                 975

Met Ala Arg Asp Pro Gln Arg Tyr Leu Val Ile Gln Gly Asp Asp Arg
                    980                 985                 990

Met Lys Leu Pro Ser Pro Asn Asp Ser Lys Phe Phe Gln Asn Leu Leu
                    995                 1000                1005

Asp Glu Glu Asp Leu Glu Asp Met Met Asp Ala Glu Glu Tyr Leu Val
    1010                1015                1020

Pro Gln Ala Phe Asn Ile Pro Pro Pro Ile Tyr Thr Ser Arg Ala Arg
1025                1030                1035                1040

Ile Asp Ser Asn Arg Ser Glu Ile Gly His Ser Pro Pro Pro Ala Tyr
                    1045                1050                1055

Thr Pro Met Ser Gly Asn Gln Phe Val Tyr Arg Asp Gly Gly Phe Ala
                    1060                1065                1070

Ala Glu Gln Gly Val Ser Val Pro Tyr Arg Ala Pro Thr Ser Thr Ile
```

-continued

```
                1075                1080                1085
Pro Glu Ala Pro Val Ala Gln Gly Ala Thr Ala Glu Ile Phe Asp Asp
   1090                1095                1100
Ser Cys Cys Asn Gly Thr Leu Arg Lys Pro Val Ala Pro His Val Gln
1105                1110                1115                1120
Glu Asp Ser Ser Thr Gln Arg Tyr Ser Ala Asp Pro Thr Val Phe Ala
                1125                1130                1135
Pro Glu Arg Ser Pro Arg Gly Glu Leu Asp Glu Gly Tyr Met Thr
            1140                1145                1150
Pro Met Arg Asp Lys Pro Lys Gln Glu Tyr Leu Asn Pro Val Glu Glu
   1155                1160                1165
Asn Pro Phe Val Ser Arg Arg Lys Asn Gly Asp Leu Gln Ala Leu Asp
   1170                1175                1180
Asn Pro Glu Tyr His Asn Ala Ser Asn Gly Pro Pro Lys Ala Glu Asp
1185                1190                1195                1200
Glu Tyr Val Asn Glu Pro Leu Tyr Leu Asn Thr Phe Ala Asn Thr Leu
                1205                1210                1215
Gly Lys Ala Glu Tyr Leu Lys Asn Asn Ile Leu Ser Met Pro Glu Lys
            1220                1225                1230
Ala Lys Lys Ala Phe Asp Asn Pro Asp Tyr Trp Asn His Ser Leu Pro
   1235                1240                1245
Pro Arg Ser Thr Leu Gln His Pro Asp Tyr Leu Gln Glu Tyr Ser Thr
1250                1255                1260
Lys Tyr Phe Tyr Lys Gln Asn Gly Arg Ile Arg Pro Ile Val Ala Glu
1265                1270                1275                1280
Asn Pro Glu Tyr Leu Ser Glu Phe Ser Leu Lys Pro Gly Thr Val Leu
            1285                1290                1295
Pro Pro Pro Pro Tyr Arg His Arg Asn Thr Val Val
         1300                1305
```

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 8
cggggagcta gcatgcgacc ctccgggacg gccggg         36

<210> SEQ ID NO 9
<211> LENGTH: 78
<212> TYPE: DNA
<213> ORGANISM: Artificial Sequence
<220> FEATURE:
<223> OTHER INFORMATION: Description of Artificial Sequence: primer

<400> SEQUENCE: 9
gcgccttaag ctacttgtca tcgtcgtcct tgtagtcgga tccacgcgga accaggatct    60
taggcccatt cgttggac                                                 78

<210> SEQ ID NO 10
<211> LENGTH: 17
<212> TYPE: PRT
<213> ORGANISM: Homo sapiens

<400> SEQUENCE: 10

Cys Val Val Gly Tyr Ile Gly Glu Arg Cys Gln Tyr Arg Asp Leu Lys

```
              1               5                  10                 15
Trp

<210> SEQ ID NO 11
<211> LENGTH: 22
<212> TYPE: PRT
<213> ORGANISM: Homo sapiens

<400> SEQUENCE: 11

Ser Asn Lys Leu Thr Gln Leu Gly Thr Phe Glu Asp His Phe Leu Ser
  1               5                  10                 15

Leu Gln Arg Met Phe Asn
             20

<210> SEQ ID NO 12
<211> LENGTH: 26
<212> TYPE: PRT
<213> ORGANISM: Homo sapiens

<400> SEQUENCE: 12

Pro Pro Leu Met Leu Tyr Asn Pro Thr Thr Tyr Gln Met Asp Val Asn
  1               5                  10                 15

Pro Glu Gly Lys Tyr Ser Phe Gly Ala Thr
             20                  25

<210> SEQ ID NO 13
<211> LENGTH: 19
<212> TYPE: PRT
<213> ORGANISM: Homo sapiens

<400> SEQUENCE: 13

Leu His Ile Leu Pro Val Ala Phe Arg Gly Asp Ser Phe Thr His Thr
  1               5                  10                 15

Pro Pro Leu

<210> SEQ ID NO 14
<211> LENGTH: 28
<212> TYPE: PRT
<213> ORGANISM: Homo sapiens

<400> SEQUENCE: 14

Cys Pro Pro Leu Met Leu Tyr Asn Pro Thr Thr Tyr Gln Met Asp Val
  1               5                  10                 15

Asn Pro Glu Gly Lys Tyr Ser Phe Gly Ala Thr Cys
             20                  25

<210> SEQ ID NO 15
<211> LENGTH: 1210
<212> TYPE: PRT
<213> ORGANISM: Homo sapiens
<220> FEATURE:
<221> NAME/KEY: SIGNAL
<222> LOCATION: (1)..(24)

<400> SEQUENCE: 15

Met Arg Pro Ser Gly Thr Ala Gly Ala Ala Leu Leu Ala Leu Leu Ala
  1               5                  10                 15

Ala Leu Cys Pro Ala Ser Arg Ala Leu Glu Glu Lys Lys Val Cys Gln
             20                  25                  30

Gly Thr Ser Asn Lys Leu Thr Gln Leu Gly Thr Phe Glu Asp His Phe
         35                  40                  45
```

-continued

```
Leu Ser Leu Gln Arg Met Phe Asn Asn Cys Glu Val Val Leu Gly Asn
     50                  55                  60

Leu Glu Ile Thr Tyr Val Gln Arg Asn Tyr Asp Leu Ser Phe Leu Lys
 65                  70                  75                  80

Thr Ile Gln Glu Val Ala Gly Tyr Val Leu Ile Ala Leu Asn Thr Val
                 85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
             115                 120                 125

Lys Thr Gly Leu Lys Glu Leu Pro Met Arg Asn Leu Gln Glu Ile Leu
130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
210                 215                 220

Gly Lys Ser Pro Ser Asp Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
```

-continued

```
            465                 470                 475                 480
        Phe Gly Thr Ser Gly Gln Lys Thr Lys Ile Ile Ser Asn Arg Gly Glu
                        485                 490                 495
        Asn Ser Cys Lys Ala Thr Gly Gln Val Cys His Ala Leu Cys Ser Pro
                        500                 505                 510
        Glu Gly Cys Trp Gly Pro Glu Pro Arg Asp Cys Val Ser Cys Arg Asn
                        515                 520                 525
        Val Ser Arg Gly Arg Glu Cys Val Asp Lys Cys Lys Leu Leu Glu Gly
                        530                 535                 540
        Glu Pro Arg Glu Phe Val Glu Asn Ser Glu Cys Ile Gln Cys His Pro
        545                 550                 555                 560
        Glu Cys Leu Pro Gln Ala Met Asn Ile Thr Cys Thr Gly Arg Gly Pro
                        565                 570                 575
        Asp Asn Cys Ile Gln Cys Ala His Tyr Ile Asp Gly Pro His Cys Val
                        580                 585                 590
        Lys Thr Cys Pro Ala Gly Val Met Gly Glu Asn Asn Thr Leu Val Trp
                        595                 600                 605
        Lys Tyr Ala Asp Ala Gly His Val Cys His Leu Cys His Pro Asn Cys
                        610                 615                 620
        Thr Tyr Gly Cys Thr Gly Pro Gly Leu Glu Gly Cys Pro Thr Asn Gly
        625                 630                 635                 640
        Pro Lys Ile Pro Ser Ile Ala Thr Gly Met Val Gly Ala Leu Leu Leu
                        645                 650                 655
        Leu Leu Val Val Ala Leu Gly Ile Gly Leu Phe Met Arg Arg Arg His
                        660                 665                 670
        Ile Val Arg Lys Arg Thr Leu Arg Arg Leu Leu Gln Glu Arg Glu Leu
                        675                 680                 685
        Val Glu Pro Leu Thr Pro Ser Gly Glu Ala Pro Asn Gln Ala Leu Leu
                        690                 695                 700
        Arg Ile Leu Lys Glu Thr Glu Phe Lys Lys Ile Lys Val Leu Gly Ser
        705                 710                 715                 720
        Gly Ala Phe Gly Thr Val Tyr Lys Gly Leu Trp Ile Pro Glu Gly Glu
                        725                 730                 735
        Lys Val Lys Ile Pro Val Ala Ile Lys Glu Leu Arg Glu Ala Thr Ser
                        740                 745                 750
        Pro Lys Ala Asn Lys Glu Ile Leu Asp Glu Ala Tyr Val Met Ala Ser
                        755                 760                 765
        Val Asp Asn Pro His Val Cys Arg Leu Leu Gly Ile Cys Leu Thr Ser
                        770                 775                 780
        Thr Val Gln Leu Ile Thr Gln Leu Met Pro Phe Gly Cys Leu Leu Asp
        785                 790                 795                 800
        Tyr Val Arg Glu His Lys Asp Asn Ile Gly Ser Gln Tyr Leu Leu Asn
                        805                 810                 815
        Trp Cys Val Gln Ile Ala Lys Gly Met Asn Tyr Leu Glu Asp Arg Arg
                        820                 825                 830
        Leu Val His Arg Asp Leu Ala Ala Arg Asn Val Leu Val Lys Thr Pro
                        835                 840                 845
        Gln His Val Lys Ile Thr Asp Phe Gly Leu Ala Lys Leu Leu Gly Ala
                        850                 855                 860
        Glu Glu Lys Glu Tyr His Ala Glu Gly Gly Lys Val Pro Ile Lys Trp
        865                 870                 875                 880
        Met Ala Leu Glu Ser Ile Leu His Arg Ile Tyr Thr His Gln Ser Asp
                        885                 890                 895
```

-continued

```
Val Trp Ser Tyr Gly Val Thr Val Trp Glu Leu Met Thr Phe Gly Ser
                900             905                 910

Lys Pro Tyr Asp Gly Ile Pro Ala Ser Glu Ile Ser Ser Ile Leu Glu
        915             920             925

Lys Gly Glu Arg Leu Pro Gln Pro Pro Ile Cys Thr Ile Asp Val Tyr
    930             935                 940

Met Ile Met Val Lys Cys Trp Met Ile Asp Ala Asp Ser Arg Pro Lys
945             950             955                 960

Phe Arg Glu Leu Ile Ile Glu Phe Ser Lys Met Ala Arg Asp Pro Gln
                965             970                 975

Arg Tyr Leu Val Ile Gln Gly Asp Glu Arg Met His Leu Pro Ser Pro
            980             985                 990

Thr Asp Ser Asn Phe Tyr Arg Ala Leu Met Asp Glu Glu Asp Met Asp
            995                 1000                1005

Asp Val Val Asp Ala Asp Glu Tyr Leu Ile Pro Gln Gln Gly Phe Phe
    1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
                1045                1050                1055

Ser Cys Pro Ile Lys Glu Asp Ser Phe Leu Gln Arg Tyr Ser Ser Asp
            1060                1065                1070

Pro Thr Gly Ala Leu Thr Glu Asp Ser Ile Asp Asp Thr Phe Leu Pro
        1075                1080                1085

Val Pro Glu Tyr Ile Asn Gln Ser Val Pro Lys Arg Pro Ala Gly Ser
    1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
            1125                1130                1135

Glu Tyr Leu Asn Thr Val Gln Pro Thr Cys Val Asn Ser Thr Phe Asp
        1140                1145                1150

Ser Pro Ala His Trp Ala Gln Lys Gly Ser His Gln Ile Ser Leu Asp
    1155                1160                1165

Asn Pro Asp Tyr Gln Gln Asp Phe Phe Pro Lys Glu Ala Lys Pro Asn
    1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
                1205                1210
```